(12) United States Patent
Ren et al.

(10) Patent No.: US 7,527,926 B2
(45) Date of Patent: May 5, 2009

(54) OLIGONUCLEOTIDES, REAGENTS AND AMPLIFICATION METHODS FOR DETECTING SEVERE ACUTE RESPIRATORY SYNDROME CORONAVIRUS

(75) Inventors: Ee Chee Ren, Singapore (SG); Martin L. Hibberd, Willynville (SG); Lisa Fong Poh Ng, Braddell View (SG)

(73) Assignee: Genome Institute of Singapore, Singapore (SG)

( * ) Notice: Subject to any disclaimer, the term of this patent is extended or adjusted under 35 U.S.C. 154(b) by 515 days.

(21) Appl. No.: 10/552,327

(22) PCT Filed: Apr. 21, 2004

(86) PCT No.: PCT/SG2004/000103

§ 371 (c)(1),
(2), (4) Date: Oct. 7, 2005

(87) PCT Pub. No.: WO2004/094667

PCT Pub. Date: Nov. 4, 2004

(65) Prior Publication Data

US 2008/0044814 A1 Feb. 21, 2008

Related U.S. Application Data

(60) Provisional application No. 60/464,115, filed on Apr. 21, 2003, provisional application No. 60/464,345, filed on Apr. 22, 2003, provisional application No. 60/464,643, filed on Apr. 23, 2003, provisional application No. 60/464,965, filed on Apr. 24, 2003, provisional application No. 60/496,016, filed on Aug. 19, 2003.

(51) Int. Cl.
*C12Q 1/70* (2006.01)
*C12P 19/34* (2006.01)
*C07H 21/04* (2006.01)

(52) U.S. Cl. ........................ 435/5; 435/91.2; 536/24.32; 536/24.33

(58) Field of Classification Search .................. 435/5, 435/91.2; 536/24.32, 24.33
See application file for complete search history.

(56) References Cited

U.S. PATENT DOCUMENTS

| | | | | |
|---|---|---|---|---|
| 7,255,986 | B2 * | 8/2007 | Maes et al. | 435/5 |
| 7,267,942 | B2 * | 9/2007 | Peiris et al. | 435/5 |
| 7,339,051 | B2 * | 3/2008 | Crooke et al. | 536/24.5 |
| 7,375,202 | B2 * | 5/2008 | Peiris et al. | 536/23.1 |
| 2004/0265796 | A1 * | 12/2004 | Briese et al. | 435/5 |
| 2006/0134609 | A1 * | 6/2006 | Linnen et al. | 435/5 |

FOREIGN PATENT DOCUMENTS

WO  02/08410  *  1/2002

OTHER PUBLICATIONS

Database Accession No. AY269391, Apr. 16, 2003.*
Buck et al., BioTechniques 27(3), 528-536 (1999).*
Poutanen et al., New England J. Med. 348, 1995-2005 (Mar. 31, 2003).*

* cited by examiner

*Primary Examiner*—Kenneth R. Horlick
(74) *Attorney, Agent, or Firm*—Rhea C. Nersesian

(57) ABSTRACT

This invention provides oligonucleotides, reagents and amplification methods for detecting the severe acute respiratory syndrome coronavirus (SARS CoV). This invention also provides related compositions, kits, systems, and computers.

16 Claims, 18 Drawing Sheets

The entire nucleotide sequence of SARS-CoV (Urbani strain).
The genome is 29, 727 nucleotides in length from 5' leader to 3'end.

```
   1 TTATTAGGTT TTTACCTACC CAGGAAAAGC CAACCAACCT CGATCTCTTG
  51 TAGATCTGTT CTCTAAACGA ACTTTAAAAT CTGTGTAGCT GTCGCTCGGC
 101 TGCATGCCTA GTGCACCTAC GCAGTATAAA CAATAATAAA TTTTACTGTC
 151 GTTGACAAGA AACGAGTAAC TCGTCCCTCT TCTGCAGACT GCTTACGGTT
 201 TCGTCCGTGT TGCAGTCGAT CATCAGCATA CCTAGGTTTC GTCCGGGTGT
 251 GACCGAAAGG TAAGATGGAG AGCCTTGTTC TTGGTGTCAA CGAGAAAACA
 301 CACGTCCAAC TCAGTTTGCC TGTCCTTCAG GTTAGAGACG TGCTAGTGCG
 351 TGGCTTCGGG GACTCTGTGG AAGAGGCCCT ATCGGAGGCA CGTGAACACC
 401 TCAAAAATGG CACTTGTGGT CTAGTAGAGC TGGAAAAGG CGTACTGCCC
 451 CAGCTTGAAC AGCCCTATGT GTTCATTAAA CGTTCTGATG CCTTAAGCAC
 501 CAATCACGGC CACAAGGTCG TTGAGCTGGT TGCAGAAATG GACGGCATTC
 551 AGTACGGTCG TAGCGGTATA ACACTGGGAG TACTCGTGCC ACATGTGGGC
 601 GAAACCCCAA TTGCATACCG CAATGTTCTT CTTCGTAAGA ACGGTAATAA
 651 GGGAGCCGGT GGTCATAGCT ATGGCATCGA TCTAAAGTCT TATGACTTAG
 701 GTGACGAGCT TGGCACTGAT CCCATTGAAG ATTATGAACA AAACTGGAAC
 751 ACTAAGCATG GCAGTGGTGC ACTCCGTGAA CTCACTCGTG AGCTCAATGG
 801 AGGTGCAGTC ACTCGCTATG TCGACAACAA TTTCTGTGGC CAGATGGGT
 851 ACCCTCTTGA TTGCATCAAA GATTTTCTCG CACGCGCGGG CAAGTCAATG
 901 TGCACTCTTT CCGAACAACT TGATTACATC GAGTCGAAGA GAGGTGTCTA
 951 CTGCTGCCGT GACCATGAGC ATGAAATTGC CTGGTTCACT GAGCGCTCTG
1001 ATAAGAGCTA CGAGCACCAG ACACCCTTCG AAATTAAGAG TGCCAAGAAA
1051 TTTGACACTT TCAAAGGGGA ATGCCCAAAG TTTGTGTTTC CTCTTAACTC
1101 AAAAGTCAAA GTCATTAAC CACGTGTTGA AAGAAAAAG ACTGAGGGTT
1151 TCATGGGGCG TATACGCTCT GTGTACCCTG TTGCATCTCC ACAGGAGTGT
1201 AACAATATGC ACTTGTCTAC CTTGATGAAA TGTAATCATT GCGATGAAGT
1251 TTCATGGCAG ACGTGCGACT TTCTGAAAGC CACTTGTGAA CATTGTGGCA
1301 CTGAAAATTT AGTTATTGAA GGACCTACTA CATGTGGGTA CCTACCTACT
1351 AATGCTGTAG TGAAAATGCC ATGTCCTGCC TGTCAAGACC CAGAGATTGG
1401 ACCTGAGCAT AGTGTTGCAG ATTATCACAA CCACTCAAAC ATTGAAACTC
1451 GACTCCGCAA GGGAGGTAGG ACTAGATGTT TTGGAGGCTG TGTGTTTGCC
1501 TATGTTGGCT GCTATAATAA GCGTGCCTAC TGGGTTCCTC GTGCTAGTGC
1551 TGATATTGGC TCAGGCCATA CTGGCATTAC TGGTGACAAT GTGGAGACCT
1601 TGAATGAGGA TCTCCTTGAG ATACTGAGTC GTGAACGTGT TAACATTAAC
1651 ATTGTTGGCG ATTTTCATTT GAATGAAGAG TTGCCATCA TTTTGGCATC
1701 TTTCTCTGCT TCTACAAGTG CCTTTATTGA CACTATAAAG AGTCTTGATT
1751 ACAAGTCTTT CAAAACCATT GTTGAGTCCT GCGGTAACTA TAAAGTTACC
1801 AAGGGAAAGC CCGTAAAAGG TGCTTGGAAC ATTGGACAAC AGAGATCAGT
1851 TTTAACACCA CTGTGTGGTT TTCCCTCACA GGCTGCTGGT GTTATCAGAT
1901 CAATTTTTGC GCGCACACTT GATGCAGCAA CCACTCAAT TCCTGATTTG
1951 CAAAGAGCAG CTGTCACCAT ACTTGATGGT ATTTCTGAAC AGTCATTACG
2001 TCTTGTCGAC GCCATGGTTT ATACTTCAGA CCTGCTCACC AACAGTGTCA
2051 TTATTATGGC ATATGTAACT GGTGGTCTTG TACAACAGAC TTCTCAGTGG
2101 TTGTCTAATC TTTTGGGCAC TACTGTTGAA AAACTCAGGC CTATCTTTGA
2151 ATGGATTGAG GCGAAACTTA GTGCAGGAGT TGAATTTCTC AAGGATGCTT
2201 GGGAGATTCT CAAATTTCTC ATTACAGGTG TTTTTGACAT CGTCAAGGGT
2251 CAAATACAGG TTGCTTCAGA TAACATCAAG GATTGTGTAA AATGCTTCAT
2301 TGATGTTGTT AACAAGGCAC TCGAAATGTG CATTGATCAA GTCACTATCG
2351 CTGGCGCAAA GTTGCGATCA CTCAACTTAG GTGAAGTCTT CATCGCTCAA
2401 AGCAAGGGAC TTTACCGTCA GTGTATACGT GGCAAGGAGC AGCTGCAACT
2451 ACTCATGCCT CTTAAGGCAC CAAAAGAAGT AACCTTTCTT GAAGGTGATT
```

Fig. 1

```
2501 CACATGACAC AGTACTTACC TCTGAGGAGG TTGTTCTCAA GAACGGTGAA
2551 CTCGAAGCAC TCGAGACGCC CGTTGATAGC TTCACAAATG GAGCTATCGT
2601 TGGCACACCA GTCTGTGTAA ATGGCCTCAT GCTCTTAGAG ATTAAGGACA
2651 AAGAACAATA CTGCGCATTG TCTCCTGGTT TACTGGCTAC AAACAATGTC
2701 TTTCGCTTAA AAGGGGGTGC ACCAATTAAA GGTGTAACCT TTGGAGAAGA
2751 TACTGTTTGG GAAGTTCAAG GTTACAAGAA TGTGAGAATC ACATTTGAGC
2801 TTGATGAACG TGTTGACAAA GTGCTTAATG AAAAGTGCTC TGTCTACACT
2851 GTTGAATCCG GTACCGAAGT TACTGAGTTT GCATGTGTTG TAGCAGAGGC
2901 TGTTGTGAAG ACTTTACAAC CAGTTTCTGA TCTCCTTACC AACATGGGTA
2951 TTGATCTTGA TGAGTGGAGT GTAGCTACAT TCTACTTATT TGATGATGCT
3001 GGTGAAGAAA ACTTTTCATC ACGTATGTAT TGTTCCTTTT ACCCTCCAGA
3051 TGAGGAAGAA GAGGACGATG CAGAGTGTGA GGAAGAAGAA ATTGATGAAA
3101 CCTGTGAACA TGAGTACGGT ACAGAGGATG ATTATCAAGG TCTCCCTCTG
3151 GAATTTGGTG CCTCAGCTGA ACAGTTCGA GTTGAGGAAG AAGAAGAGGA
3201 AGACTGGCTG ATGATACTA CTGAGCAATC AGAGATTGAG CCAGAACCAG
3251 AACCTACACC TGAAGAACCA GTTAATCAGT TTACTGGTTA TTTAAAACTT
3301 ACTGACAATG TTGCCATTAA ATGTGTTGAC ATCGTTAAGG AGGCACAAAG
3351 TGCTAATCCT ATGGTGATTG TAAATGCTGC TAACATACAC CTGAAACATG
3401 GTGGTGGTGT AGCAGGTGCA CTCAACAAGG CAACCAATGG TGCCATGCAA
3451 AAGGAGAGTG ATGATTACAT TAAGCTAAAT GGCCCTCTTA CAGTAGGAGG
3501 GTCTTGTTTG CTTTCTGGAC ATAATCTTGC TAAGAAGTGT CTGCATGTTG
3551 TTGGACCTAA CCTAAATGCA GGTGAGGACA TCCAGCTTCT TAAGGCAGCA
3601 TATGAAAATT TCAATTCACA GGACATCTTA CTTGCACCAT GTTGTCAGC
3651 AGGCATATTT GGTGCTAAAC CACTTCAGTC TTTACAAGTG TGCGTGCAGA
3701 CGGTTCGTAC ACAGGTTTAT ATTGCAGTCA ATGACAAAGC TCTTTATGAG
3751 CAGGTTGTCA TGGATTATCT TGATAACCTG AAGCCTAGAG TGGAAGCACC
3801 TAAACAAGAG GAGCCACCAA ACACAGAAGA TTCCAAAACT GAGGAGAAAT
3851 CTGTCGTACA GAAGCCTGTC GATGTGAAGC CAAAAATTAA GGCCTGCATT
3901 GATGAGGTTA CCACAACACT GGAAGAAACT AAGTTTCTTA CCAATAAGTT
3951 ACTCTTGTTT GCTGATATCA ATGGTAAGCT TTACCATGAT TCTCAGAACA
4001 TGCTTAGAGG TGAAGATATG TCTTTCCTTG AGAAGGATGC ACCTTACATG
4051 GTAGGTGATG TTATCACTAG TGGTGATATC ACTTGTGTTG TAATACCCTC
4101 CAAAAAGGCT GGTGGCACTA CTGAGATGCT CTCAAGAGCT TTGAAGAAAG
4151 TGCCAGTTGA TGAGTATATA ACCACGTACC CTGGACAAGG ATGTGCTGGT
4201 TATACACTTG AGGAAGCTAA GACTGCTCTT AAGAAATGCA AATCTGCATT
4251 TTATGTACTA CCTTCAGAAG CACCTAATGC TAAGGAAGAG ATTCTAGGAA
4301 CTGTATCCTG GAATTTGAGA GAAATGCTTG CTCATGCTGA AGAGACAAGA
4351 AAATTAATGC CTATATGCAT GGATGTTAGA GCCATAATGG CAACCATCCA
4401 ACGTAAGTAT AAAGGAATTA AAATTCAAGA GGGCATCGTT GACTATGGTG
4451 TCCGATTCTT CTTTTATACT AGTAAAGAGC CTGTAGCTTC TATTATTACG
4501 AAGCTGAACT CTCTAAATGA GCCGCTTGTC ACAATGCCAA TTGGTTATGT
4551 GACACATGGT TTTAATCTTG AAGAGGCTGC GCGCTGTATG CGTTCTCTTA
4601 AAGCTCCTGC CGTAGTGTCA GTATCATCAC CAGATGCTGT TACTACATAT
4651 AATGGATACC TCACTTCGTC ATCAAAGACA TCTGAGGAGC ACTTTGTAGA
4701 AACAGTTTCT TTGGCTGGCT CTTACAGAGA TTGGTCCTAT TCAGGACAGC
4751 GTACAGAGTT AGGTGTTGAA TTTCTTAAGC GTGGTGACAA AATTGTGTAC
4801 CACACTCTGG AGAGCCCCGT CGAGTTTCAT CTTGACGGTG AGGTTCTTTC
4851 ACTTGACAAA CTAAAGAGTC TCTTATCCCT GCGGGAGGTT AAGACTATAA
4901 AAGTGTTCAC AACTGTGGAC AACACTAATC TCCACACACA GCTTGTGGAT
4951 ATGTCTATGA CATATGGACA GCAGTTTGGT CCAACATACT GGATGGTGC
5001 TGATGTTACA AAAATTAAAC CTCATGTAAA TCATGAGGGT AAGACTTTCT
5051 TTGTACTACC TAGTGATGAC ACACTACGTA GTGAAGCTTT CGAGTACTAC
5101 CATACTCTTG ATGAGAGTTT TCTTGGTAGG TACATGTCTG CTTTAAACCA
```

Fig. 1 (cont.)

```
5151 CACAAAGAAA TGGAAATTTC CTCAAGTTGG TGGTTTAACT TCAATTAAAT
5201 GGGCTGATAA CAATTGTTAT TTGTCTAGTG TTTTATTAGC ACTTCAACAG
5251 CTTGAAGTCA AATTCAATGC ACCAGCACTT CAAGAGGCTT ATTATAGAGC
5301 CCGTGCTGGT GATGCTGCTA ACTTTTGTGC ACTCATACTC GCTTACAGTA
5351 ATAAAACTGT TGGCGAGCTT GGTGATGTCA GAGAAACTAT GACCCATCTT
5401 CTACAGCATG CTAATTTGGA ATCTGCAAAG CGAGTTCTTA ATGTGGTGTG
5451 TAAACATTGT GGTCAGAAAA CTACTACCTT AACGGGTGTA GAAGCTGTGA
5501 TGTATATGGG TACTCTATCT TATGATAATC TTAAGACAGG TGTTTCCATT
5551 CCATGTGTGT GTGGTCGTGA TGCTACACAA TATCTAGTAC AACAAGAGTC
5601 TTCTTTTGTT ATGATGTCTG CACCACCTGC TGAGTATAAA TTACAGCAAG
5651 GTACATTCTT ATGTGCGAAT GAGTACACTG GTAACTATCA GTGTGGTCAT
5701 TACACTCATA TAACTGCTAA GGAGACCCTC TATCGTATTG ACGGAGCTCA
5751 CCTTACAAAG ATGTCAGAGT ACAAAGGACC AGTGACTGAT GTTTTCTACA
5801 AGGAAACATC TTACACTACA ACCATCAAGC CTGTGTCGTA TAAACTCGAT
5851 GGAGTTACTT ACACAGAGAT TGAACCAAAA TTGGATGGGT ATTATAAAAA
5901 GGATAATGCT TACTATACAG AGCAGCCTAT AGACCTTGTA CCAACTCAAC
5951 CATTACCAAA TGCGAGTTTT GATAATTTCA AACTCACATG TTCTAACACA
6001 AAATTTGCTG ATGATTTAAA TCAAATGACA GGCTTCACAA AGCCAGCTTC
6051 ACGAGAGCTA TCTGTCACAT TCTTCCCAGA CTTGAATGGC GATGTAGTGG
6101 CTATTGACTA TAGACACTAT TCAGCGAGTT TCAAGAAAGG TGCTAAATTA
6151 CTGCATAAGC CAATTGTTTG GCACATTAAC CAGGCTACAA CCAAGACAAC
6201 GTTCAAACCA AACACTTGGT GTTTACGTTG TCTTTGGAGT ACAAAGCCAG
6251 TAGATACTTC AAATTCATTT GAAGTTCTGG CAGTAGAAGA CACACAAGGA
6301 ATGGACAATC TTGCTTGTGA AAGTCAACAA CCCACCTCTG AAGAAGTAGT
6351 GGAAAATCCT ACCATACAGA AGGAAGTCAT AGAGTGTGAC GTGAAAACTA
6401 CCGAAGTTGT AGGCAATGTC ATACTTAAAC CATCAGATGA AGGTGTTAAA
6451 GTAACACAAG AGTTAGGTCA TGAGGATCTT ATGGCTGCTT ATGTGGAAAA
6501 CACAAGCATT ACCATTAAGA AACCTAATGA GCTTTCACTA GCCTTAGGTT
6551 TAAAAACAAT TGCCACTCAT GGTATTGCTG CAATTAATAG TGTTCCTTGG
6601 AGTAAAATTT TGGCTTATGT CAAACCATTC TTAGGACAAG CAGCAATTAC
6651 AACATCAAAT TGCGCTAAGA GATTAGCACA ACGTGTGTTT AACAATTATA
6701 TGCCTTATGT GTTTACATTA TTGTTCCAAT TGTGTACTTT TACTAAAAGT
6751 ACCAATTCTA GAATTAGAGC TTCACTACCT ACAACTATTG CTAAAAATAG
6801 TGTTAAGAGT GTTGCTAAAT TATGTTTGGA TGCCGGCATT AATTATGTGA
6851 AGTCACCCAA ATTTTCTAAA TTGTTCACAA TCGCTATGTG CTATTGTTG
6901 TTAAGTATTT GCTTAGGTTC TCTAATCTGT GTAACTGCTG CTTTTGGTGT
6951 ACTCTTATCT AATTTTGGTG CTCCTTCTTA TTGTAATGGC GTTAGAGAAT
7001 TGTATCTTAA TTCGTCTAAC GTTACTACTA TGGATTTCTG TGAAGGTTCT
7051 TTTCCTTGCA GCATTTGTTT AAGTGGATTA GACTCCCTTG ATTCTTATCC
7101 AGCTCTTGAA ACCATTCAGG TGACGATTTC ATCGTACAAG CTAGACTTGA
7151 CAATTTTAGG TCTGGCCGCT GAGTGGGTTT TGGCATATAT GTTGTTCACA
7201 AAATTCTTTT ATTTATTAGG TCTTTCAGCT ATAATGCAGG TGTTCTTTGG
7251 CTATTTTGCT AGTCATTTCA TCAGCAATTC TTGGCTCATG TGGTTTATCA
7301 TTAGTATTGT ACAAATGGCA CCCGTTTCTG CAATGGTTAG GATGTACATC
7351 TTCTTTGCTT CTTTCTACTA CATATGGAAG AGCTATGTTC ATATCATGGA
7401 TGGTTGCACC TCTTCGACTT GCATGATGTG CTATAAGCGC AATCGTGCCA
7451 CACGCGTTGA GTGTACAACT ATTGTTAATG CATGAAGAG ATCTTTCTAT
7501 GTCTATGCAA ATGGAGGCCG TGGCTTCTGC AAGACTCACA ATTGGAATTG
7551 TCTCAATTGT GACACATTTT GCACTGGTAG TACATTCATT AGTGATGAAG
7601 TTGCTCGTGA TTTGTCACTC CAGTTTAAAA GACCAATCAA CCCTACTGAC
7651 CAGTCATCGT ATATTGTTGA TAGTGTTGCT GTGAAAAATG GCGCGCTTCA
7701 CCTCTACTTT GACAAGGCTG GTCAAAAGAC CTATGAGAGA CATCCGCTCT
7751 CCCATTTTGT CAATTTAGAC AATTTGAGAG CTAACAACAC TAAAGGTTCA
```

```
7801 CTGCCTATTA ATGTCATAGT TTTTGATGGC AAGTCCAAAT GCGACGAGTC
7851 TGCTTCTAAG TCTGCTTCTG TGTACTACAG TCAGCTGATG TGCCAACCTA
7901 TTCTGTTGCT TGACCAAGTT CTTGTATCAG ACGTTGGAGA TAGTACTGAA
7951 GTTTCCGTTA AGATGTTTGA TGCTTATGTC GACACCTTTT CAGCAACTTT
8001 TAGTGTTCCT ATGGAAAAAC TTAAGGCACT TGTTGCTACA GCTCACAGCG
8051 AGTTAGCAAA GGGTGTAGCT TTAGATGGTG TCCTTTCTAC ATTCGTGTCA
8101 GCTGCCCGAC AAGGTGTTGT TGATACCGAT GTTGACACAA GGATGTTAT
8151 TGAATGTCTC AAACTTTCAC ATCACTCTGA CTTAGAAGTG ACAGGTGACA
8201 GTTGTAACAA TTTCATGCTC ACCTATAATA AGGTTGAAAA CATGACGCCC
8251 AGAGATCTTG GCGCATGTAT TGACTGTAAT GCAAGGCATA TCAATGCCCA
8301 AGTAGCAAAA AGTCACAATG TTTCACTCAT CTGGAATGTA AAAGACTACA
8351 TGTCTTTATC TGAACAGCTG CGTAAACAAA TTCGTAGTGC TGCCAAGAAG
8401 AACAACATAC CTTTTAGACT AACTTGTGCT ACAACTAGAC AGGTTGTCAA
8451 TGTCATAACT ACTAAAATCT CACTCAAGGG TGGTAAGATT GTTAGTACTT
8501 GTTTTAAACT TATGCTTAAG GCCACATTAT TGTGCGTTCT TGCTGCATTG
8551 GTTTGTTATA TCGTTATGCC AGTACATACA TTGTCAATCC ATGATGGTTA
8601 CACAAATGAA ATCATTGGTT ACAAAGCCAT TCAGGATGGT GTCACTCGTG
8651 ACATCATTTC TACTGATGAT TGTTTTGCAA ATAAACATGC TGGTTTTGAC
8701 GCATGGTTTA GCCAGCGTGG TGGTTCATAC AAAAATGACA AAAGCTGCCC
8751 TGTAGTAGCT GCTATCATTA CAAGAGAGAT TGGTTTCATA GTGCCTGGCT
8801 TACCGGGTAC TGTGCTGAGA GCAATCAATG GTGACTTCTT GCATTTTCTA
8851 CCTCGTGTTT TTAGTGCTGT TGGCAACATT TGCTACACAC CTTCCAAACT
8901 CATTGAGTAT AGTGATTTTG CTACCTCTGC TTGCGTTCTT GCTGCTGAGT
8951 GTACAATTTT TAAGGATGCT ATGGGCAAAC CTGTGCCATA TTGTTATGAC
9001 ACTAATTTGC TAGAGGGTTC TATTTCTTAT AGTGAGCTTC GTCCAGACAC
9051 TCGTTATGTG CTTATGGATG GTTCCATCAT ACAGTTTCCT AACACTTACC
9101 TGGAGGGTTC TGTTAGAGTA GTAACAACTT TTGATGCTGA GTACTGTAGA
9151 CATGGTACAT GCGAAAGGTC AGAAGTAGGT ATTTGCCTAT CTACCAGTGG
9201 TAGATGGGTT CTTAATAATG AGCATTACAG AGCTCTATCA GGAGTTTTCT
9251 GTGGTGTTGA TGCGATGAAT CTCATAGCTA ACATCTTTAC TCCTCTTGTG
9301 CAACCTGTGG GTGCTTTAGA TGTGTCTGCT TCAGTAGTGG CTGGTGGTAT
9351 TATTGCCATA TTGGTGACTT GTGCTGCCTA CTACTTTATG AAATTCAGAC
9401 GTGTTTTTGG TGAGTACAAC CATGTTGTTG CTGCTAATGC ACTTTTGTTT
9451 TTGATGTCTT TCACTATACT CTGTCTGGTA CCAGCTTACA GCTTTCTGCC
9501 GGGAGTCTAC TCAGTCTTTT ACTTGTACTT GACATTCTAT TTCACCAATG
9551 ATGTTTCATT CTTGGCTCAC CTTCAATGGT TTGCCATGTT TTCTCCTATT
9601 GTGCCTTTTT GGATAACAGC AATCTATGTA TTCTGTATTT CTCTGAAGCA
9651 CTGCCATTGG TTCTTTAACA ACTATCTTAG GAAAAGAGTC ATGTTTAATG
9701 GAGTTACATT TAGTACCTTC GAGGAGGCTG CTTTGTGTAC CTTTTTGCTC
9751 AACAAGGAAA TGTACCTAAA ATTGCGTAGC GAGACACTGT TGCCACTTAC
9801 ACAGTATAAC AGGTATCTTG CTCTATATAA CAAGTACAAG TATTTCAGTG
9851 GAGCCTTAGA TACTACCAGC TATCGTGAAG CAGCTTGCTG CCACTTAGCA
9901 AAGGCTCTAA ATGACTTTAG CAACTCAGGT GCTGATGTTC TCTACCAACC
9951 ACCACAGACA TCAATCACTT CTGCTGTTCT GCAGAGTGGT TTTAGGAAAA
10001 TGGCATTCCC GTCAGGCAAA GTTGAAGGGT GCATGGTACA AGTAACCTGT
10051 GGAACTACAA CTCTTAATGG ATTGTGGTTG GATGACACAG TATACTGTCC
10101 AAGACATGTC ATTTGCACAG CAGAAGACAT GCTTAATCCT AACTATGAAG
10151 ATCTGCTCAT TCGCAAATCC AACCATAGCT TCTTGTTCA GGCTGGCAAT
10201 GTTCAACTTC GTGTTATTGG CCATTCTATG CAAAATTGTC TGCTTAGGCT
10251 TAAAGTTGAT ACTTCTAACC CTAAGACACC CAAGTATAAA TTTGTCCGTA
10301 TCCAACCTGG TCAAACATTT TCAGTTCTAG CATGCTACAA TGGTTCACCA
10351 TCTGGTGTTT ATCAGTGTGC CATGAGACCT AATCATACCA TTAAAGGTTC
10401 TTTCCTTAAT GGATCATGTG GTAGTGTTGG TTTTAACATT GATTATGATT
```

```
10451 GCGTGTCTTT CTGCTATATG CATCATATGG AGCTTCCAAC AGGAGTACAC
10501 GCTGGTACTG ACTTAGAAGG TAAATTCTAT GGTCCATTTG TTGACAGACA
10551 AACTGCACAG GCTGCAGGTA CAGACACAAC CATAACATTA AATGTTTTGG
10601 CATGGCTGTA TGCTGCTGTT ATCAATGGTG ATAGGTGGTT TCTTAATAGA
10651 TTCACCACTA CTTTGAATGA CTTTAACCTT GTGGCAATGA AGTACAACTA
10701 TGAACCTTTG ACACAAGATC ATGTTGACAT ATTGGGACCT CTTTCTGCTC
10751 AAACAGGAAT TGCCGTCTTA GATATGTGTG CTGCTTTGAA AGAGCTGCTG
10801 CAGAATGGTA TGAATGGTCG TACTATCCTT GGTAGCACTA TTTTAGAAGA
10851 TGAGTTTACA CCATTTGATG TTGTTAGACA ATGCTCTGGT GTTACCTTCC
10901 AAGGTAAGTT CAAGAAAATT GTTAAGGGCA CTCATCATTG GATGCTTTTA
10951 ACTTTCTTGA CATCACTATT GATTCTTGTT CAAAGTACAC AGTGGTCACT
11001 GTTTTTCTTT GTTTACGAGA ATGCTTTCTT GCCATTTACT CTTGGTATTA
11051 TGGCAATTGC TGCATGTGCT ATGCTGCTTG TTAAGCATAA GCACGCATTC
11101 TTGTGCTTGT TTCTGTTACC TTCTCTTGCA ACAGTTGCTT ACTTTAATAT
11151 GGTCTACATG CCTGCTAGCT GGGTGATGCG TATCATGACA TGGCTTGAAT
11201 TGGCTGACAC TAGCTTGTCT GGTTATAGGC TTAAGGATTG TGTTATGTAT
11251 GCTTCAGCTT TAGTTTTGCT TATTCTCATG ACAGCTCGCA CTGTTTATGA
11301 TGATGCTGCT AGACGTGTTT GGACACTGAT GAATGTCATT ACACTTGTTT
11351 ACAAAGTCTA CTATGGTAAT GCTTTAGATC AAGCTATTTC CATGTGGGCC
11401 TTAGTTATTT CTGTAACCTC TAACTATTCT GGTGTCGTTA CGACTATCAT
11451 GTTTTTAGCT AGAGCTATAG TGTTTGTGTG TGTTGAGTAT TACCCATTGT
11501 TATTTATTAC TGGCAACACC TTACAGTGTA TCATGCTTGT TTATTGTTTC
11551 TTAGGCTATT GTTGCTGCTG CTACTTTGGC CTTTTCTGTT TACTCAACCG
11601 TTACTTCAGG CTTACTCTTG GTGTTTATGA CTACTTGGTC TCTACACAAG
11651 AATTTAGGTA TATGAACTCC CAGGGGCTTT GCCTCCTAA GAGTAGTATT
11701 GATGCTTTCA AGCTTAACAT TAAGTTGTTG GGTATTGGAG GTAAACCATG
11751 TATCAAGGTT GCTACTGTAC AGTCTAAAAT GTCTGACGTA AAGTGCACAT
11801 CTGTGGTACT GCTCTCGGTT CTCAACAAC TTAGAGTAGA GTCATCTTCT
11851 AAATTGTGGG CACAATGTGT ACAACTCCAC AATGATATTC TTCTTGCAAA
11901 AGACACAACT GAAGCTTTCG AGAAGATGGT TTCTCTTTTG TCTGTTTTGC
11951 TATCCATGCA GGGTGCTGTA GACATTAATA GGTTGTGCGA GGAAATGCTC
12001 GATAACCGTG CTACTCTTCA GGCTATTGCT TCAGAATTTA GTTCTTTACC
12051 ATCATATGCC GCTTATGCCA CTGCCCAGGA GGCCTATGAG CAGGCTGTAG
12101 CTAATGGTGA TTCTGAAGTC GTTCTCAAAA AGTTAAAGAA ATCTTTGAAT
12151 GTGGCTAAAT CTGAGTTTGA CCGTGATGCT GCCATGCAAC GCAAGTTGGA
12201 AAAGATGGCA GATCAGGCTA TGACCCAAAT GTACAAACAG GCAAGATCTG
12251 AGGACAAGAG GGCAAAAGTA ACTAGTGCTA TGCAAACAAT GCTCTTCACT
12301 ATGCTTAGGA AGCTTGATAA TGATGCACTT AACAACATTA TCAACAATGC
12351 GCGTGATGGT TGTGTTCCAC TCAACATCAT ACCATTGACT ACAGCAGCCA
12401 AACTCATGGT TGTTGTCCCT GATTATGGTA CCTACAAGAA CACTTGTGAT
12451 GGTAACACCT TTACATATGC ATCTGCACTC TGGGAAATCC AGCAAGTTGT
12501 TGATGCGGAT AGCAAGATTG TTCAACTTAG TGAAATTAAC ATGGACAATT
12551 CACCAAATTT GGCTTGGCCT CTTATTGTTA CAGCTCTAAG AGCCAACTCA
12601 GCTGTTAAAC TACAGAATAA TGAACTGAGT CCAGTAGCAC TACGACAGAT
12651 GTCCTGTGCG GCTGGTACCA CACAAACAGC TTGTACTGAT GACAATGCAC
12701 TTGCCTACTA TAACAATTCG AAGGGAGGTA GGTTTGTGCT GGCATTACTA
12751 TCAGACCACC AAGATCTCAA ATGGGCTAGA TTCCCTAAGA GTGATGGTAC
12801 AGGTACAATT TACACAGAAC TGGAACCACC TTGTAGGTTT GTTACAGACA
12851 CACCAAAAGG GCCTAAAGTG AAATACTTGT ACTTCATCAA AGGCTTAAAC
12901 AACCTAAATA GAGGTATGGT GCTGGGCAGT TTAGCTGCTA CAGTACGTCT
12951 TCAGGCTGGA AATGCTACAG AAGTACCTGC CAATTCAACT GTGCTTTCCT
13001 TCTGTGCTTT TGCAGTAGAC CCTGCTAAAG CATATAAGGA TTACCTAGCA
13051 AGTGGAGGAC AACCAATCAC CAACTGTGTG AAGATGTTGT GTACACACAC
```

Fig. 1 (cont.)

```
13101 TGGTACAGGA CAGGCAATTA CTGTAACACC AGAAGCTAAC ATGGACCAAG
13151 AGTCCTTTGG TGGTGCTTCA TGTTGTCTGT ATTGTAGATG CCACATTGAC
13201 CATCCAAATC CTAAAGGATT CTGTGACTTG AAAGGTAAGT ACGTCCAAAT
13251 ACCTACCACT TGTGCTAATG ACCCAGTGGG TTTTACACTT AGAAACACAG
13301 TCTGTACCGT CTGCGGAATG TGGAAAGGTT ATGGCTGTAG TTGTGACCAA
13351 CTCCGCGAAC CCTTGATGCA GTCTGCGGAT GCATCAACGT TTTTAAACGG
13401 GTTTGCGGTG TAAGTGCAGC CCGTCTTACA CCGTGCGGCA CAGGCACTAG
13451 TACTGATGTC GTCTACAGGG CTTTTGATAT TTACAACGAA AAAGTTGCTG
13501 GTTTTGCAAA GTTCCTAAAA ACTAATTGCT GTCGCTTCCA GGAGAAGGAT
13551 GAGGAAGGCA ATTTATTAGA CTCTTACTTT GTAGTTAAGA GGCATACTAT
13601 GTCTAACTAC CAACATGAAG AGACTATTTA TAACTTGGTT AAAGATTGTC
13651 CAGCGGTTGC TGTCCATGAC TTTTTCAAGT TTAGAGTAGA TGGTGACATG
13701 GTACCACATA TATCACGTCA GCGTCTAACT AAATACACAA TGGCTGATTT
13751 AGTCTATGCT CTACGTCATT TTGATGAGGG TAATTGTGAT ACATTAAAAG
13801 AAATACTCGT CACATACAAT TGCTGTGATG ATGATTATTT CAATAAGAAG
13851 GATTGGTATG ACTTCGTAGA GAATCCTGAC ATCTTACGCG TATATGCTAA
13901 CTTAGGTGAG CGTGTACGCC AATCATTATT AAAGACTGTA CAATTCTGCG
13951 ATGCTATGCG TGATGCAGGC ATTGTAGGCG TACTGACATT AGATAATCAG
14001 GATCTTAATG GAACTGGTA CGATTTCGGT GATTTCGTAC AAGTAGCACC
14051 AGGCTGCGGA GTTCCTATTG TGGATTCATA TTACTCATTG CTGATGCCCA
14101 TCCTCACTTT GACTAGGGCA TTGGCTGCTG AGTCCCATAT GGATGCTGAT
14151 CTCGCAAAAC CACTTATTAA GTGGGATTTG CTGAAATATG ATTTTACGGA
14201 AGAGAGACTT TGTCTCTTCG ACCGTTATTT AAATATTGG GACCAGACAT
14251 ACCATCCCAA TTGTATTAAC TGTTTGGATG ATAGGTGTAT CCTTCATTGT
14301 GCAAACTTTA ATGTGTTATT TTCTACTGTG TTTCCACCTA CAAGTTTTGG
14351 ACCACTAGTA AGAAAATAT TTGTAGATGG TGTTCCTTTT GTTGTTTCAA
14401 CTGGATACCA TTTTCGTGAG TTAGGAGTCG TACATAATCA GGATGTAAAC
14451 TTACATAGCT CGCGTCTCAG TTTCAAGGAA CTTTTAGTGT ATGCTGCTGA
14501 TCCAGCTATG CATGCAGCTT CTGGCAATTT ATTGCTAGAT AAACGCACTA
14551 CATGCTTTTC AGTAGCTGCA CTAACAAACA ATGTTGCTTT TCAAACTGTC
14601 AAACCCGGTA ATTTTAATAA AGACTTTTAT GACTTTGCTG TGTCTAAAGG
14651 TTTCTTTAAG GAAGGAAGTT CTGTTGAACT AAAACACTTC TTCTTTGCTC
14701 AGGATGGCAA CGCTGCTATC AGTGATTATG ACTATTATCG TTATAATCTG
14751 CCAACAATGT GTGATATCAG ACAACTCCTA TTCGTAGTTG AAGTTGTTGA
14801 TAAATACTTT GATTGTTACG ATGGTGGCTG TATTAATGCC AACCAAGTAA
14851 TCGTTAACAA TCTGGATAAA TCAGCTGGTT TCCCATTTAA TAAATGGGGT
14901 AAGGCTAGAC TTTATTATGA CTCAATGAGT TATGAGGATC AAGATGCACT
14951 TTTCGCGTAT ACTAAGCGTA ATGTCATCCC TACTATAACT CAAATGAATC
15001 TTAAGTATGC CATTAGTGCA AAGAATAGAG CTCGCACCGT AGCTGGTGTC
15051 TCTATCTGTA GTACTATGAC AAATAGACAG TTTCATCAGA AATTATTGAA
15101 GTCAATAGCC GCCACTAGAG GAGCTACTGT GGTAATTGGA ACAAGCAAGT
15151 TTTACGGTGG CTGGCATAAT ATGTTAAAAA CTGTTTACAG TGATGTAGAA
15201 ACTCCACACC TTATGGGTTG GGATTATCCA AAATGTGACA GAGCCATGCC
15251 TAACATGCTT AGGATAATGG CCTCTCTTGT TCTTGCTCGC AAACATAACA
15301 CTTGCTGTAA CTTATCACAC CGTTTCTACA GGTTAGCTAA CGAGTGTGCG
15351 CAAGTATTAA GTGAGATGGT CATGTGTGGC GGCTCACTAT ATGTTAAACC
15401 AGGTGGAACA TCATCCGGTG ATGCTACAAC TGCTTATGCT AATAGTGTCT
15451 TTAACATTTG TCAAGCTGTT ACAGCCAATG TAAATGCACT TCTTTCAACT
15501 GATGGTAATA AGATAGCTGA CAAGTATGTC CGCAATCTAC AACACAGGCT
15551 CTATGAGTGT CTCTATAGAA ATAGGGATGT TGATCATGAA TTCGTGGATG
15601 AGTTTTACGC TTACCTGCGT AAACATTTCT CCATGATGAT TCTTTCTGAT
15651 GATGCCGTTG TGTGCTATAA CAGTAACTAT GCGGCTCAAG GTTTAGTAGC
15701 TAGCATTAAG AACTTTAAGG CAGTTCTTTA TTATCAAAAT AATGTGTTCA
```

```
15751 TGTCTGAGGC AAAATGTTGG ACTGAGACTG ACCTTACTAA AGGACCTCAC
15801 GAATTTTGCT CACAGCATAC AATGCTAGTT AAACAAGGAG ATGATTACGT
15851 GTACCTGCCT TACCCAGATC CATCAAGAAT ATTAGGCGCA GGCTGTTTTG
15901 TCGATGATAT TGTCAAAACA GATGGTACAC TTATGATTGA AAGGTTCGTG
15951 TCACTGGCTA TTGATGCTTA CCCACTTACA AAACATCCTA ATCAGGAGTA
16001 TGCTGATGTC TTTCACTTGT ATTTACAATA CATTAGAAAG TTACATGATG
16051 AGCTTACTGG CCACATGTTG GACATGTATT CCGTAATGCT AACTAATGAT
16101 AACACCTCAC GGTACTGGGA ACCTGAGTTT TATGAGGCTA TGTACACACC
16151 ACATACAGTC TTGCAGGCTG TAGGTGCTTG TGTATTGTGC AATTCACAGA
16201 CTTCACTTCG TTGCGGTGCC TGTATTAGGA GACCATTCCT ATGTTGCAAG
16251 TGCTGCTATG ACCATGTCAT TCAACATCA CACAAATTAG TGTTGTCTGT
16301 TAATCCCTAT GTTTGCAATG CCCCAGGTTG TGATGTCACT GATGTGACAC
16351 AACTGTATCT AGGAGGTATG AGCTATTATT GCAAGTCACA TAAGCCTCCC
16401 ATTAGTTTTC CATTATGTGC TAATGGTCAG GTTTTGGTT TATACAAAAA
16451 CACATGTGTA GGCAGTGACA ATGTCACTGA CTTCAATGCG ATAGCAACAT
16501 GTGATTGGAC TAATGCTGGC GATTACATAC TTGCCAACAC TTGTACTGAG
16551 AGACTCAAGC TTTTCGCAGC AGAAACGCTC AAAGCCACTG AGGAAACATT
16601 TAAGCTGTCA TATGGTATTG CTACTGTACG CGAAGTACTC TCTGACAGAG
16651 AATTGCATCT TTCATGGGAG GTTGGAAAAC CTAGACCACC ATTGAACAGA
16701 AACTATGTCT TTACTGGTTA CCGTGTAACT AAAAATAGTA AGTACAGAT
16751 TGGAGAGTAC ACCTTTGAAA AAGGTGACTA TGGTGATGCT GTTGTGTACA
16801 GAGGTACTAC GACATACAAG TTGAATGTTG GTGATTACTT TGTGTTGACA
16851 TCTCACACTG TAATGCCACT TAGTGCACCT ACTCTAGTGC CACAAGAGCA
16901 CTATGTGAGA ATTACTGGCT TGTACCCAAC ACTCAACATC TCAGATGAGT
16951 TTTCTAGCAA TGTTGCAAAT TATCAAAAGG TCGGCATGCA AAAGTACTCT
17001 ACACTCCAAG GACCACCTGG TACTGGTAAG AGTCATTTTG CCATCGGACT
17051 TGCTCTCTAT TACCCATCTG CTCGCATAGT GTATACGGCA TGCTCTCATG
17101 CAGCTGTTGA TGCCCTATGT GAAAAGGCAT TAAAATATTT GCCCATAGAT
17151 AAATGTAGTA GAATCATACC TGCGCGTGCG CGCGTAGAGT GTTTTGATAA
17201 ATTCAAAGTG AATTCAACAC TAGAACAGTA TGTTTTCTGC ACTGTAAATG
17251 CATTGCCAGA AACAACTGCT GACATTGTAG TCTTTGATGA AATCTCTATG
17301 GCTACTAATT ATGACTTGAG TGTTGTCAAT GCTAGACTTC GTGCAAAACA
17351 CTACGTCTAT ATTGGCGATC CTGCTCAATT ACCAGCCCCC CGCACATTGC
17401 TGACTAAAGG CACACTAGAA CCAGAATATT TTAATTCAGT GTGCAGACTT
17451 ATGAAAACAA TAGGTCCAGA CATGTTCCTT GGAACTTGTC GCCGTTGTCC
17501 TGCTGAAATT GTTGACACTG TGAGTGCTTT AGTTTATGAC AATAAGCTAA
17551 AAGCACACAA GGATAAGTCA GCTCAATGCT TCAAAATGTT CTACAAAGGT
17601 GTTATTACAC ATGATGTTTC ATCTGCAATC AACAGACCTC AAATAGGCGT
17651 TGTAAGAGAA TTTCTTACAC GCAATCCTGC TTGGAGAAAA GCTGTTTTTA
17701 TCTCACCTTA TAATTCACAG AACGCTGTAG CTTCAAAAAT CTTAGGATTG
17751 CCTACGCAGA CTGTTGATTC ATCACAGGGT TCTGAATATG ACTATGTCAT
17801 ATTCACACAA ACTACTGAAA CAGCACACTC TTGTAATGTC AACCGCTTCA
17851 ATGTGGCTAT CACAAGGGCA AAAATTGGCA TTTTGTGCAT AATGTCTGAT
17901 AGAGATCTTT ATGACAAACT GCAATTTACA AGTCTAGAAA TACCACGTCG
17951 CAATGTGGCT ACATTACAAG CAGAAAATGT AACTGGACTT TTTAAGGACT
18001 GTAGTAAGAT CATTACTGGT CTTCATCCTA CACAGGCACC TACACACCTC
18051 AGCGTTGATA TAAAGTTCAA GACTGAAGGA TTATGTGTTG ACATACCAGG
18101 CATACCAAAG GACATGACCT ACCGTAGACT CATCTCTATG ATGGGTTTCA
18151 AAATGAATTA CCAAGTCAAT GGTTACCCTA ATATGTTTAT CACCCGCGAA
18201 GAAGCTATTC GTCACGTTCG TGCGTGGATT GGCTTTGATG TAGAGGGCTG
18251 TCATGCAACT AGAGATGCTG TGGGTACTAA CCTACCTCTC CAGCTAGGAT
18301 TTTCTACAGG TGTTAACTTA GTAGCTGTAC CGACTGGTTA TGTTGACACT
18351 GAAAATAACA CAGAATTCAC CAGAGTTAAT GCAAAACCTC CACCAGGTGA
```

Fig. 1 (cont.)

```
18401 CCAGTTTAAA CATCTTATAC CACTCATGTA TAAAGGCTTG CCCTGGAATG
18451 TAGTGCGTAT TAAGATAGTA CAAATGCTCA GTGATACACT GAAAGGATTG
18501 TCAGACAGAG TCGTGTTCGT CCTTGGGCG CATGGCTTTG AGCTTACATC
18551 AATGAAGTAC TTTGTCAAGA TTGGACCTGA AGAACGTGT TGTCTGTGTG
18601 ACAAACGTGC AACTTGCTTT TCTACTTCAT CAGATACTTA TGCCTGCTGG
18651 AATCATTCTG TGGGTTTTGA CTATGTCTAT AACCCATTTA TGATTGATGT
18701 TCAGCAGTGG GGCTTACGG GTAACCTTCA GAGTAACCAT GACCAACATT
18751 GCCAGGTACA TGGAAATGCA CATGTGGCTA GTTGTGATGC TATCATGACT
18801 AGATGTTTAG CAGTCCATGA GTGCTTTGTT AAGCGCGTTG ATTGGTCTGT
18851 TGAATACCCT ATTATAGGAG ATGAACTGAG GGTTAATTCT GCTTGCAGAA
18901 AAGTACAACA CATGGTTGTG AAGTCTGCAT TGCTTGCTGA TAAGTTTCCA
18951 GTTCTTCATG ACATTGGAAA TCCAAAGGCT ATCAAGTGTG TGCCTCAGGC
19001 TGAAGTAGAA TGGAAGTTCT ACGATGCTCA GCCATGTAGT GACAAAGCTT
19051 ACAAAATAGA GGAGCTCTTC TATTCTTATG CTACACATCA CGATAAATTC
19101 ACTGATGGTG TTTGTTTGTT TTGGAATTGT AACGTTGATC GTTACCCAGC
19151 CAATGCAATT GTGTGTAGGT TTGACACAAG AGCCTTGTCA AACTTGAACT
19201 TACCAGGCTG TGATGGTGGT AGTTTGTATG TGAATAAGCA TGCATTCCAC
19251 ACTCCAGCTT TCGATAAAAG TGCATTACT AATTTAAAGC AATTGCCTTT
19301 CTTTTACTAT TCTGATAGTC CTTGTGAGTC TCATGGCAAA CAAGTAGTGT
19351 CGGATATTGA TTATGTTCCA CTCAAATCTG CTACGTGTAT TACACGATGC
19401 AATTTAGGTG GTGCTGTTTG CAGACACCAT GCAAATGAGT ACCGACAGTA
19451 CTTGGATGCA TATAATATGA TGATTTCTGC TGGATTTAGC CTATGGATTT
19501 ACAAACAATT TGATACTTAT AACCTGTGGA ATACATTTAC CAGGTTACAG
19551 AGTTTAGAAA ATGTGGCTTA TAATGTTGTT AATAAAGGAC ACTTTGATGG
19601 ACACGCCGGC GAAGCACCTG TTTCCATCAT TAATAATGCT GTTTACACAA
19651 AGGTAGATGG TATTGATGTG GAGATCTTTG AAAATAAGAC AACACTTCCT
19701 GTTAATGTTG CATTTGAGCT TTGGGCTAAG CGTAACATTA ACCAGTGCC
19751 AGAGATTAAG ATACTCAATA ATTTGGGTGT TGATATCGCT GCTAATACTG
19801 TAATCTGGGA CTACAAAAGA GAAGCCCCAG CACATGTATC TACAATAGGT
19851 GTCTGCACAA TGACTGACAT TGCCAAGAAA CCTACTGAGA GTGCTTGTTC
19901 TTCACTTACT GTCTTGTTTG ATGGTAGAGT GGAAGGACAG GTAGACCTTT
19951 TTAGAAACGC CCGTAATGGT GTTTTAATAA CAGAAGGTTC AGTCAAAGGT
20001 CTAACACCTT CAAAGGGACC AGCACAAGCT AGCGTCAATG GAGTCACATT
20051 AATTGGAGAA TCAGTAAAAA CACAGTTTAA CTACTTTAAG AAAGTAGACG
20101 GCATTATTCA ACAGTTGCCT GAAACCTACT TTACTCAGAG CAGAGACTTA
20151 GAGGATTTTA AGCCCAGATC ACAAATGGAA ACTGACTTC TCGAGCTCGC
20201 TATGGATGAA TTCATACAGC GATATAAGCT CGAGGGCTAT GCCTTCGAAC
20251 ACATCGTTTA TGGAGATTTC AGTCATGGAC AACTTGGCGG TCTTCATTTA
20301 ATGATAGGCT TAGCCAAGCG CTCACAAGAT TCACCACTTA AATTAGAGGA
20351 TTTTATCCCT ATGGACAGCA CAGTGAAAAA TTACTTCATA ACAGATGCGC
20401 AAACAGGTTC ATCAAAATGT GTGTGTTCTG TGATTGATCT TTTACTTGAT
20451 GACTTTGTCG AGATAATAAA GTCACAAGAT TTGTCAGTGA TTTCAAAAGT
20501 GGTCAAGGTT ACAATTGACT ATGCTGAAAT TCATTCATG CTTTGGTGTA
20551 AGGATGGACA TGTTGAAACC TTCTACCCAA AACTACAAGC AAGTCAAGCG
20601 TGGCAACCAG GTGTTGCGAT GCCTAACTTG TACAAGATGC AAAGAATGCT
20651 TCTTGAAAAG TGTGACCTTC AGAATTATGG TGAAAATGCT GTTATACCAA
20701 AAGGAATAAT GATGAATGTC GCAAAGTATA CTCAACTGTG TCAATACTTA
20751 AATACACTTA CTTTAGCTGT ACCCTACAAC ATGAGAGTTA TTCACTTTGG
20801 TGCTGGCTCT GATAAAGGAG TTGCACCAGG TACAGCTGTG CTCAGACAAT
20851 GGTTGCCAAC TGGCACACTA CTTGTCGATT CAGATCTTAA TGACTTCGTC
20901 TCCGACGCAG ATTCTACTTT AATTGGAGAC TGTGCAACAG TACATACGGC
20951 TAATAAATGG GACCTTATTA TTAGCGATAT GTATGACCCT AGGACCAAAC
21001 ATGTGACAAA AGAGAATGAC TCTAAAGAAG GGTTTTTCAC TTATCTGTGT
```

Fig. 1 (cont.)

```
21051 GGATTTATAA AGCAAAAACT AGCCCTGGGT GGTTCTATAG CTGTAAAGAT
21101 AACAGAGCAT TCTTGGAATG CTGACCTTTA CAAGCTTATG GGCCATTTCT
21151 CATGGTGGAC AGCTTTTGTT ACAAATGTAA ATGCATCATC ATCGGAAGCA
21201 TTTTTAATTG GGCTAACTA TCTTGGCAAG CCGAAGGAAC AAATTGATGG
21251 CTATACCATG CATGCTAACT ACATTTCTG GAGGAACACA AATCCTATCC
21301 AGTTGTCTTC CTATTCACTC TTTGACATGA GCAAATTTCC TCTTAAATTA
21351 AGAGGAACTG CTGTAATGTC TCTTAAGGAG AATCAAATCA ATGATATGAT
21401 TTATTCTCTT CTGGAAAAAG GTAGGCTTAT CATTAGAGAA ACAACAGAG
21451 TTGTGGTTTC AAGTGATATT CTTGTTAACA ACTAAACGAA CATGTTTATT
21501 TTCTTATTAT TTCTTACTCT CACTAGTGGT AGTGACCTTG ACCGGTGCAC
21551 CACTTTTGAT GATGTTCAAG CTCCTAATTA CACTCAACAT ACTTCATCTA
21601 TGAGGGGGGT TTACTATCCT GATGAAATTT TTAGATCAGA CACTCTTTAT
21651 TTAACTCAGG ATTTATTTCT TCCATTTTAT TCTAATGTTA CAGGGTTTCA
21701 TACTATTAAT CATACGTTTG GCAACCCTGT CATACCTTTT AAGGATGGTA
21751 TTTATTTTGC TGCCACAGAG AAATCAAATG TTGTCCGTGG TTGGGTTTTT
21801 GGTTCTACCA TGAACAACAA GTCACAGTCG GTGATTATTA TTAACAATTC
21851 TACTAATGTT GTTATACGAG CATGTAACTT TGAATTGTGT GACAACCCTT
21901 TCTTTGCTGT TTCTAAACCC ATGGGTACAC AGACACATAC TATGATATTC
21951 GATAATGCAT TTAATTGCAC TTCGAGTAC ATATCTGATG CCTTTTCGCT
22001 TGATGTTTCA GAAAAGTCAG GTAATTTTAA ACACTTACGA GAGTTTGTGT
22051 TTAAAAATAA AGATGGGTTT CTCTATGTTT ATAAGGGCTA TCAACCTATA
22101 GATGTAGTTC GTGATCTACC TTCTGGTTTT AACACTTTGA AACCTATTTT
22151 TAAGTTGCCT CTTGGTATTA ACATTACAAA TTTTAGAGCC ATTCTTACAG
22201 CCTTTTCACC TGCTCAAGAC ATTTGGGGCA CGTCAGCTGC AGCCTATTTT
22251 GTTGGCTATT TAAAGCCAAC TACATTTATG CTCAAGTATG ATGAAAATGG
22301 TACAATCACA GATGCTGTTG ATTGTTCTCA AAATCCACTT GCTGAACTCA
22351 AATGCTCTGT TAAGAGCTTT GAGATTGACA AAGGAATTTA CCAGACCTCT
22401 AATTTCAGGG TTGTTCCCTC AGGAGATGTT GTGAGATTCC CTAATATTAC
22451 AAACTTGTGT CCTTTTGGAG AGGTTTTAA TGCTACTAAA TTCCCTTCTG
22501 TCTATGCATG GGAGAGAAAA AAAATTTCTA ATTGTGTTGC TGATTACTCT
22551 GTGCTCTACA ACTCAACATT TTTTTCAACC TTTAAGTGCT ATGGCGTTTC
22601 TGCCACTAAG TTGAATGATC TTTGCTTCTC CAATGTCTAT GCAGATTCTT
22651 TTGTAGTCAA GGGAGATGAT GTAAGACAAA TAGCGCCAGG ACAAACTGGT
22701 GTTATTGCTG ATTATAATTA TAAATTGCCA GATGATTTCA TGGGTTGTGT
22751 CCTTGCTTGG AATACTAGGA ACATTGATGC TACTTCAACT GGTAATTATA
22801 ATTATAAATA TAGGTATCTT AGACATGGCA AGCTTAGGCC CTTTGAGAGA
22851 GACATATCTA ATGTGCCTTT CTCCCCTGAT GGCAAACCTT GCACCCCACC
22901 TGCTCTTAAT TGTTATTGGC CATTAAATGA TTATGGTTTT TACACCACTA
22951 CTGGCATTGG CTACCAACCT TACAGAGTTG TAGTACTTTC TTTTGAACTT
23001 TTAAATGCAC CGGCCACGGT TTGTGGACCA AAATTATCCA CTGACCTTAT
23051 TAAGAACCAG TGTGTCAATT TTAATTTTAA TGGACTCACT GGTACTGGTG
23101 TGTTAACTCC TTCTTCAAAG AGATTTCAAC CATTTCAACA ATTTGGCCGT
23151 GATGTTTCTG ATTTCACTGA TTCCGTTCGA GATCCTAAAA CATCTGAAAT
23201 ATTAGACATT TCACCTTGCT CTTTTGGGGG TGTAAGTGTA ATTACACCTG
23251 GAACAAATGC TTCATCTGAA GTTGCTGTTC TATATCAAGA TGTTAACTGC
23301 ACTGATGTTT CTACAGCAAT TCATGCAGAT CAACTCACAC CAGCTTGGCG
23351 CATATATTCT ACTGGAAACA ATGTATTCCA GACTCAAGCA GGCTGTCTTA
23401 TAGGAGCTGA GCATGTCGAC ACTTCTTATG AGTGCGACAT CCTATTGGA
23451 GCTGGCATTT GTGCTAGTTA CCATACAGTT TCTTTATTAC GTAGTACTAG
23501 CCAAAAATCT ATTGTGGCTT ATACTATGTC TTTAGGTGCT GATAGTTCAA
23551 TTGCTTACTC TAATAACACC ATTGCTATAC CTACTAACTT TTCAATTAGC
23601 ATTACTACAG AAGTAATGCC TGTTTCTATG GCTAAAACCT CCGTAGATTG
23651 TAATATGTAC ATCTGCGGAG ATTCTACTGA ATGTGCTAAT TTGCTTCTCC
```

```
23701 AATATGGTAG CTTTTGCACA CAACTAAATC GTGCACTCTC AGGTATTGCT
23751 GCTGAACAGG ATCGCAACAC ACGTGAAGTG TTCGCTCAAG TCAAACAAAT
23801 GTACAAAACC CCAACTTTGA AATATTTTGG TGGTTTTAAT TTTTCACAAA
23851 TATTACCTGA CCCTCTAAAG CCAACTAAGA GGTCTTTTAT TGAGGACTTG
23901 CTCTTTAATA AGGTGACACT CGCTGATGCT GGCTTCATGA AGCAATATGG
23951 CGAATGCCTA GGTGATATTA ATGCTAGAGA TCTCATTTGT GCGCAGAAGT
24001 TCAATGGACT TACAGTGTTG CCACCTCTGC TCACTGATGA TATGATTGCT
24051 GCCTACACTG CTGCTCTAGT TAGTGGTACT GCCACTGCTG GATGGACATT
24101 TGGTGCTGGC GCTGCTCTTC AAATACCTTT TGCTATGCAA ATGGCATATA
24151 GGTTCAATGG CATTGGAGTT ACCCAAAATG TTCTCTATGA GAACCAAAAA
24201 CAAATCGCCA ACCAATTTAA CAAGGCGATT AGTCAAATTC AAGAATCACT
24251 TACAACAACA TCAACTGCAT TGGGCAAGCT GCAAGACGTT GTTAACCAGA
24301 ATGCTCAAGC ATTAAACACA CTTGTTAAAC AACTTAGCTC TAATTTTGGT
24351 GCAATTTCAA GTGTGCTAAA TGATATCCTT TCGCGACTTG ATAAAGTCGA
24401 GGCGGAGGTA CAAATTGACA GGTTAATTAC AGGCAGACTT CAAAGCCTTC
24451 AAACCTATGT AACACAACAA CTAATCAGGG CTGCTGAAAT CAGGGCTTCT
24501 GCTAATCTTG CTGCTACTAA AATGTCTGAG TGTGTTCTTG ACAATCAAA
24551 AAGAGTTGAC TTTTGTGGAA AGGGCTACCA CCTTATGTCC TTCCCACAAG
24601 CAGCCCCGCA TGGTGTTGTC TTCCTACATG TCACGTATGT GCCATCCCAG
24651 GAGAGGAACT TCACCACAGC GCCAGCAATT TGTCATGAAG GCAAAGCATA
24701 CTTCCCTCGT GAAGGTGTTT TTGTGTTTAA TGGCACTTCT TGGTTTATTA
24751 CACAGAGGAA CTTCTTTTCT CCACAAATAA TTACTACAGA CAATACATTT
24801 GTCTCAGGAA ATTGTGATGT CGTTATTGGC ATCATTAACA ACACAGTTTA
24851 TGATCCTCTG CAACCTGAGC TCGACTCATT CAAAGAAGAG CTGGACAAGT
24901 ACTTCAAAAA TCATACATCA CCAGATGTTG ATCTTGGCGA CATTTCAGGC
24951 ATTAACGCTT CTGTCGTCAA CATTCAAAAA GAAATTGACC GCCTCAATGA
25001 GGTCGCTAAA AATTTAAATG AATCACTCAT TGACCTTCAA GAATTGGGAA
25051 AATATGAGCA ATATATTAAA TGGCCTTGGT ATGTTTGGCT CGGCTTCATT
25101 GCTGGACTAA TTGCCATCGT CATGGTTACA ATCTTGCTTT GTTGCATGAC
25151 TAGTTGTTGC AGTTGCCTCA AGGGTGCATG CTCTTGTGGT TCTTGCTGCA
25201 AGTTTGATGA GGATGACTCT GAGCCAGTTC TCAAGGGTGT CAAATTACAT
25251 TACACATAAA CGAACTTATG GATTTGTTTA TGAGATTTTT TACTCTTGGA
25301 TCAATTACTG CACAGCCAGT AAAAATTGAC AATGCTTCTC CTGCAAGTAC
25351 TGTTCATGCT ACAGCAACGA TACCGCTACA AGCCTCACTC CCTTTCGGAT
25401 GGCTTGTTAT TGGCGTTGCA TTTCTTGCTG TTTTTCAGAG CGCTACCAAA
25451 ATAATTGCGC TCAATAAAAG ATGGCAGCTA GCCCTTTATA AGGGCTTCCA
25501 GTTCATTTGC AATTTACTGC TGCTATTTGT TACCATCTAT TCACATCTTT
25551 TGCTTGTCGC TGCAGGTATG GAGGCGCAAT TTTTGTACCT CTATGCCTTG
25601 ATATATTTTC TACAATGCAT CAACGCATGT AGAATTATTA TGAGATGTTG
25651 GCTTTGTTGG AAGTGCAAAT CCAAGAACCC ATTACTTTAT GATGCCAACT
25701 ACTTTGTTTG CTGGCACACA CATAACTATG ACTACTGTAT ACCATATAAC
25751 AGTGTCACAG ATACAATTGT CGTTACTGAA GGTGACGGCA TTTCAACACC
25801 AAAACTCAAA GAAGACTACC AAATTGGTGG TTATTCTGAG GATAGGCACT
25851 CAGGTGTTAA AGACTATGTC GTTGTACATG GCTATTTCAC CGAAGTTTAC
25901 TACCAGCTTG AGTCTACACA AATTACTACA GACACTGGTA TTGAAAATGC
25951 TACATTCTTC ATCTTTAACA AGCTTGTTAA AGACCCACCG AATGTGCAAA
26001 TACACACAAT CGACGGCTCT TCAGGAGTTG CTAATCCAGC AATGGATCCA
26051 ATTTATGATG AGCCGACGAC GACTACTAGC GTGCCTTTGT AAGCACAAGA
26101 AAGTGAGTAC GAACTTATGT ACTCATTCGT TTCGGAAGAA ACAGGTACGT
26151 TAATAGTTAA TAGCGTACTT CTTTTTCTTG CTTTCGTGGT ATTCTTGCTA
26201 GTCACACTAG CCATCCTTAC TGCGCTTCGA TTGTGTGCGT ACTGCTGCAA
26251 TATTGTTAAC GTGAGTTTAG TAAAACCAAC GGTTTACGTC TACTCGCGTG
26301 TTAAAAATCT GAACTCTTCT GAAGGAGTTC CTGATCTTCT GGTCTAAACG
```

```
26351 AACTAACTAT TATTATTATT CTGTTTGGAA CTTTAACATT GCTTATCATG
26401 GCAGACAACG GTACTATTAC CGTTGAGGAG CTTAAACAAC TCCTGGAACA
26451 ATGGAACCTA GTAATAGGTT TCCTATTCCT AGCCTGGATT ATGTTACTAC
26501 AATTTGCCTA TTCTAATCGG AACAGGTTTT TGTACATAAT AAAGCTTGTT
26551 TTCCTCTGGC TCTTGTGGCC AGTAACACTT GCTTGTTTTG TGCTTGCTGC
26601 TGTCTACAGA ATTAATTGGG TGACTGGCGG GATTGCGATT GCAATGGCTT
26651 GTATTGTAGG CTTGATGTGG CTTAGCTACT TCGTTGCTTC CTTCAGGCTG
26701 TTTGCTCGTA CCCGCTCAAT GTGGTCATTC AACCCAGAAA CAAACATTCT
26751 TCTCAATGTG CCTCTCCGGG GGACAATTGT GACCAGACCG CTCATGGAAA
26801 GTGAACTTGT CATTGGTGCT GTGATCATTC GTGGTCACTT GCGAATGGCC
26851 GGACACCCCC TAGGGCGCTG TGACATTAAG GACCTGCCAA AAGAGATCAC
26901 TGTGGCTACA TCACGAACGC TTTCTTATTA CAAATTAGGA GCGTCGCAGC
26951 GTGTAGGCAC TGATTCAGGT TTTGCTGCAT ACAACCGCTA CCGTATTGGA
27001 AACTATAAAT TAAATACAGA CCACGCCGGT AGCAACGACA ATATTGCTTT
27051 GCTAGTACAG TAAGTGACAA CAGATGTTTC ATCTTGTTGA CTTCCAGGTT
27101 ACAATAGCAG AGATATTGAT TATCATTATG AGGACTTTCA GGATTGCTAT
27151 TTGGAATCTT GACGTTATAA TAAGTTCAAT AGTGAGACAA TTATTTAAGC
27201 CTCTAACTAA GAAGAATTAT TCGGAGTTAG ATGATGAAGA ACCTATGGAG
27251 TTAGATTATC CATAAAACGA ACATGAAAAT TATTCTCTTC CTGACATTGA
27301 TTGTATTTAC ATCTTGCGAG CTATATCACT ATCAGGAGTG TGTTAGAGGT
27351 ACGACTGTAC TACTAAAAGA ACCTTGCCCA TCAGGAACAT ACGAGGGCAA
27401 TTCACCATTT CACCCTCTTG CTGACAATAA ATTTGCACTA ACTTGCACTA
27451 GCACACACTT TGCTTTTGCT TGTGCTGACG GTACTCGACA TACCTATCAG
27501 CTGCGTGCAA GATCAGTTTC ACCAAAACTT TTCATCAGAC AAGAGGAGGT
27551 TCAACAAGAG CTCTACTCGC CACTTTTTCT CATTGTTGCT GCTCTAGTAT
27601 TTTTAATACT TTGCTTCACC ATTAAGAGAA AGACAGAATG AATGAGCTCA
27651 CTTTAATTGA CTTCTATTTG TGCTTTTTAG CCTTTCTGCT ATTCCTTGTT
27701 TTAATAATGC TTATTATATT TGGTTTTCA CTCGAAATCC AGGATCTAGA
27751 AGAACCTTGT ACCAAAGTCT AAACGAACAT GAAACTTCTC ATTGTTTTGA
27801 CTTGTATTTC TCTATGCAGT TGCATATGCA CTGTAGTACA GCGCTGTGCA
27851 TCTAATAAAC CTCATGTGCT TGAAGATCCT TGTAAGGTAC AACACTAGGG
27901 GTAATACTTA TAGCACTGCT TGGCTTGTG CTCTAGGAAA GGTTTTACCT
27951 TTTCATAGAT GGCACACTAT GGTTCAAACA TGCACACCTA ATGTTACTAT
28001 CAACTGTCAA GATCCAGCTG GTGGTGCGCT TATAGCTAGG TGTTGGTACC
28051 TTCATGAAGG TCACCAAACT GCTGCATTTA GAGACGTACT TGTTGTTTTA
28101 AATAAACGAA CAAATTAAAA TGTCTGATAA TGGACCCCAA TCAAACCAAC
28151 GTAGTGCCCC CCGCATTACA TTTGGTGGAC CCACAGATTC AACTGACAAT
28201 AACCAGAATG GAGGACGCAA TGGGGCAAGG CCAAAACAGC GCCGACCCCA
28251 AGGTTTACCC AATAATACTG CGTCTTGGTT CACAGCTCTC ACTCAGCATG
28301 GCAAGGAGGA ACTTAGATTC CCTCGAGGCC AGGGCGTTCC AATCAACACC
28351 AATAGTGGTC CAGATGACCA AATTGGCTAC TACCGAAGAG CTACCCGACG
28401 AGTTCGTGGT GGTGACGGCA AAATGAAAGA GCTCAGCCCC AGATGGTACT
28451 TCTATTACCT AGGAACTGGC CCAGAAGCTT CACTTCCCTA CGGCGCTAAC
28501 AAAGAAGGCA TCGTATGGGT TGCAACTGAG GGAGCCTTGA ATACACCCAA
28551 AGACCACATT GGCACCCGCA ATCCTAATAA CAATGCTGCC ACCGTGCTAC
28601 AACTTCCTCA AGGAACAACA TTGCCAAAAG CTTCTACGC AGAGGGAAGC
28651 AGAGGCGGCA GTCAAGCCTC TTCTCGCTCC TCATCACGTA GTCGCGGTAA
28701 TTCAAGAAAT TCAACTCCTG GCAGCAGTAG GGGAAATTCT CCTGCTCGAA
28751 TGGCTAGCGG AGGTGGTGAA ACTGCCCTCG CGCTATTGCT GCTAGACAGA
28801 TTGAACCAGC TTGAGAGCAA AGTTTCTGGT AAAGGCCAAC AACAACAAGG
28851 CCAAACTGTC ACTAAGAAAT CTGCTGCTGA GGCATCTAAA AAGCCTCGCC
28901 AAAAACGTAC TGCCACAAAA CAGTACAACG TCACTCAAGC ATTTGGGAGA
28951 CGTGGTCCAG AACAAACCCA AGGAAATTTC GGGGACCAAG ACCTAATCAG
```

Fig. 1 (cont.)

```
29001 ACAAGGAACT GATTACAAAC ATTGGCCGCA AATTGCACAA TTTGCTCCAA
29051 GTGCCTCTGC ATTCTTTGGA ATGTCACGCA TTGGCATGGA AGTCACACCT
29101 TCGGGAACAT GGCTGACTTA TCATGGAGCC ATTAAATTGG ATGACAAAGA
29151 TCCACAATTC AAAGACAACG TCATACTGCT GAACAAGCAC ATTGACGCAT
29201 ACAAAACATT CCCACCAACA GAGCCTAAAA AGGACAAAAA GAAAAAGACT
29251 GATGAAGCTC AGCCTTTGCC GCAGAGACAA AAGAAGCAGC CCACTGTGAC
29301 TCTTCTTCCT GCGGCTGACA TGGATGATTT CTCCAGACAA CTTCAAAATT
29351 CCATGAGTGG AGCTTCTGCT GATTCAACTC AGGCATAAAC ACTCATGATG
29401 ACCACACAAG GCAGATGGGC TATGTAAACG TTTTCGCAAT TCCGTTTACG
29451 ATACATAGTC TACTCTTGTG CAGAATGAAT TCTCGTAACT AAACAGCACA
29501 AGTAGGTTTA GTTAACTTTA ATCTCACATA GCAATCTTTA ATCAATGTGT
29551 AACATTAGGG AGGACTTGAA AGAGCCACCA CATTTTCATC GAGGCCACGC
29601 GGAGTACGAT CGAGGGTACA GTGAATAATG CTAGGGAGAG CTGCCTATAT
29651 GGAAGAGCCC TAATGTGTAA AATTAATTTT AGTAGTGCTA TCCCCATGTG
29701 ATTTTAATAG CTTCTTAGGA GAATGAC
```

Fig. 1 (cont.)

Group 1 Coronavirus (Human Coronavirus-HCoV 229E and Procine epidemic diarrhea virus-PEDV) with SARS (3 different isolates: Toronto, Singapore and Guangzhou)

SEQ ID NO: 23

```
NC_004718(TOR)    AATATGTTAAAAACTGTTTACAGTGATGTAGAAACTCCACACCTTATGGGTTGGGATTAT
AY283794(GIS)     AATATGTTAAAAACTGTTTACAGTGATGTAGAAACTCCACACCTTATGGGTTGGGATTAT
AY278489(GZ)      AATATGTTAAAAACTGTTTACAGTGATGTAGAAACTCCACACCTTATGGGTTGGGATTAT
NC_002645(HCoV)   AATATGTTAAAGAACCTGATGGCCGATGTTGATGATCCTAAATTGATGGGATGGGACTAT
NC_003436(PEDV)   AATATGCTTAAGAACCTTATTGATGGTGTTGAAAATCCGTGTCTTATGGGTTGGGATTAC

NC_004718(TOR)    CCAAAATGTGACAGAGCCATGCCTAACATGCTTAGGATAATGGCCTCTCTTGTTCTTGCT
AY283794(GIS)     CCAAAATGTGACAGAGCCATGCCTAACATGCTTAGGATAATGGCCTCTCTTGTTCTTGCT
AY278489(GZ)      CCAAAATGTGACAGAGCCATGCCTAACATGCTTAGGATAATGGCCTCTCTTGTTCTTGCT
NC_002645(HCoV)   CCTAAGTGTGATAGAGCTATGCCCTCAATGATTCGTATGTTGTCGGCTATCATCTTAGGT
NC_003436(PEDV)   CCAAAGTGCGATAGAGCACTGCCCAATATGATACGCATGATTTCAGCCATGATCTTAGGC

NC_004718(TOR)    CGCAAACATAACACTTGCTGTAACTTATCACACCGTTTCTACAGGTTAGCTAACGAGTGT
AY283794(GIS)     CGCAAACATAACACTTGCTGTAACTTATCACACCGTTTCTACAGGTTAGCTAACGAGTGT
AY278489(GZ)      CGCAAACATAACACTTGCTGTAACTTATCACACCGTTTCTACAGGTTAGCTAACGAGTGT
NC_002645(HCoV)   TCTAAGCATGTCACATGTTGTACGGCTAGTGATAAATTTTATAGACTTAGTAATGAGCTT
NC_003436(PEDV)   TCTAAGCACACCATGCTGCAGTTCTACTGACCGCTTTTTCAGGTTGTGCAATGAATTG
```

SEQ ID NO: 24

```
NC_004718(TOR)    GCGCAAGTATTAAGTGAGATGGTCATGTGTGGCGGCTCACTATATGTTAAACCAGGTGGA
AY283794(GIS)     GCGCAAGTATTAAGTGAGATGGTCATGTGTGGCGGCTCACTATATGTTAAACCAGGTGGA
AY278489(GZ)      GCGCAAGTATTAAGTGAGATGGTCATGTGTGGCGGCTCACTATATGTTAAACCAGGTGGA
NC_002645(HCoV)   GCTCAAGTTTTGACCGAGGTTGTTTATTCAAATGGTGGGTTTTATTTTAAACCTGGTGGT
NC_003436(PEDV)   GCTCAAGTCCTTACTGAGGTTGTTATTCTAATGGAGGGTTTTATTTGAAGCCAGGTGGT
```

Group 2 Coronaviruses (Bovine coronavirus-BCoV and Murine hepatitis virus-MHV) with SARS (3 isolates: Singapore, Guangzhou and Toronto)

SEQ ID NO: 23

```
AY283794(GIS)     AATATGTTAAAAACTGTTTACAGTGATGTAGAAACTCCACACCTTATGGGTTGGGATTAT
AY278489(GZ)      AATATGTTAAAAACTGTTTACAGTGATGTAGAAACTCCACACCTTATGGGTTGGGATTAT
NC_004718(TOR)    AATATGTTAAAAACTGTTTACAGTGATGTAGAAACTCCACACCTTATGGGTTGGGATTAT
NC_003045(BCoV)   GATATGTTACGTCGCCTTATTAAAGATGTTGATAATCCTGTACTTATGGGTTGGGATTAT
NC_001846(MHV)    GATATGTTACGCCGCCTTATTAAAGATGTTGATAGTCCTGTACTCATGGGTTGGGACTAT

AY283794(GIS)     CCAAAATGTGACAGAGCCATGCCTAACATGCTTAGGATAATGGCCTCTCTTGTTCTTGCT
AY278489(GZ)      CCAAAATGTGACAGAGCCATGCCTAACATGCTTAGGATAATGGCCTCTCTTGTTCTTGCT
NC_004718(TOR)    CCAAAATGTGACAGAGCCATGCCTAACATGCTTAGGATAATGGCCTCTCTTGTTCTTGCT
NC_003045(BCoV)   CCTAAGTGTGATCGTGCTATGCCAAACATACTACGTATTGTTAGTAGTCTGGTTTTGGCT
NC_001846(MHV)    CCTAAATGTGATCGTGCTATGCCAAACATACTGCGTATTGTTAGTAGTTTGGTGCTAGCC

AY283794(GIS)     CGCAAACATAACACTTGCTGTAACTTATCACACCGTTTCTACAGGTTAGCTAACGAGTGT
AY278489(GZ)      CGCAAACATAACACTTGCTGTAACTTATCACACCGTTTCTACAGGTTAGCTAACGAGTGT
NC_004718(TOR)    CGCAAACATAACACTTGCTGTAACTTATCACACCGTTTCTACAGGTTAGCTAACGAGTGT
NC_003045(BCoV)   CGAAAACATGAGGCATGTTGTTCGCAAAGCGATAGGTTTTATCGACTTGCGAATGAATGC
NC_001846(MHV)    CGTAAACATGATTCGTGCTGTTCGCATACGGATAGATTCTATCGTCTTGCGAACGAGTGC
```

SEQ ID NO: 24

```
AY283794(GIS)     GCGCAAGTATTAAGTGAGATGGTCATGTGTGGCGGCTCACTATATGTTAAACCAGGTGGA
AY278489(GZ)      GCGCAAGTATTAAGTGAGATGGTCATGTGTGGCGGCTCACTATATGTTAAACCAGGTGGA
NC_004718(TOR)    GCGCAAGTATTAAGTGAGATGGTCATGTGTGGCGGCTCACTATATGTTAAACCAGGTGGA
NC_003045(BCoV)   GCACAAGTTCTGAGTGAAATTGTTATGTGTGGTGGCTGTTATTATGTTAAGCCTGGTGGC
NC_001846(MHV)    GCCCAAGTTTTGAGTGAAATTGTTATGTGTGGTGGTTGTTATTATGTTAAACCAGGTGGC
```

Group 3 Coronavirus (Avian Infectious Bronchitis Virus-IBV) with SARS (3 isolates: Singapore, Guangzhou and Toronto)

SEQ ID NO: 23

```
AY283794(GIS)     AATATGTTAAAAACTGTTTACAGTGATGTAGAAACTCCACACCTTATGGGTTGGGATTAT
AY278489(GZ)      AATATGTTAAAAACTGTTTACAGTGATGTAGAAACTCCACACCTTATGGGTTGGGATTAT
NC_004718(TOR)    AATATGTTAAAAACTGTTTACAGTGATGTAGAAACTCCACACCTTATGGGTTGGGATTAT
NC_001451(IBV)    AACATGTTGAGAAACCTGATTCAGGGTGTTGAAGACCCAATTCTTATGGGTTGGGATTAT

AY283794(GIS)     CCAAAATGTGACAGAGCCATGCCTAACATGCTTAGGATAATGGCCTCTCTTGTTCTTGCT
AY278489(GZ)      CCAAAATGTGACAGAGCCATGCCTAACATGCTTAGGATAATGGCCTCTCTTGTTCTTGCT
NC_004718(TOR)    CCAAAATGTGACAGAGCCATGCCTAACATGCTTAGGATAATGGCCTCTCTTGTTCTTGCT
NC_001451(IBV)    CCTAAGTGTGATAGAGCAATGCCTAATTTGTTGCGTATAGCAGCATCCTTAGTACTTGCT

AY283794(GIS)     CGCAAACATAACACTTGCTGTAACTTATCACACCGTTTCTACAGGTTAGCTAACGAGTGT
AY278489(GZ)      CGCAAACATAACACTTGCTGTAACTTATCACACCGTTTCTACAGGTTAGCTAACGAGTGT
NC_004718(TOR)    CGCAAACATAACACTTGCTGTAACTTATCACACCGTTTCTACAGGTTAGCTAACGAGTGT
NC_001451(IBV)    CGCAAACACACTAACTGTTGTAGTTGGTCTGAACGCATTTATAGGTTGTATAATGAATGC
```

Fig. 2

```
                                                                                   SEQ ID NO: 24
AY283794(GIS)     GCGCAAGTATTAAGTGAGATGGTCATGTGTGGCGGCTCAC-TATATGTTAAACCAGGTGG
AY278489(GZ)      GCGCAAGTATTAAGTGAGATGGTCATGTGTGGCGGCTCAC-TATATGTTAAACCAGGTGG
NC_004718(TOR)    GCGCAAGTATTAAGTGAGATGGTCATGTGTGGCGGCTCAC-TATATGTTAAACCAGGTGG
NC_001451(IBV)    GCCCAGGTCTTATCTGAAACTGT-ACTTGCTACAGGTGGTATTTATGTTAAACCTGGTGG
```

Fig. 2 (cont.)

```
SEQUENCE LISTING

<160> NUMBER OF SEQ ID NOS: 33

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tgatggttgt gttccactca acatc                                           25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
acactggtac aggacaggca attac                                           25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggtgtaagtg cagcccgtct tacac                                           25

<210> SEQ ID NO 4
<211> LENGTH: 25
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
cgaattttgc tcacagcata caatg                                              25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
attggagagt acacctttga aaaag                                              25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gctagacttc gtgcaaaaca ctacg                                              25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tgtggctagt tgtgatgcta tcatg                                              25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gctacacatc acgataaatt cactg                                              25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
cactcaaatc tgctacgtgt attac                                              25

<210> SEQ ID NO 10
<211> LENGTH: 25
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 10
ctcgctatgg atgaattcat acagc                                       25

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ggttgggatt atccaaaatg tga                                         23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ggcatcatca gaaagaatca tcat                                        24

<210> SEQ ID NO 13
<211> LENGTH: 29727
<212> TYPE: DNA
<213> ORGANISM: SARS coronavirus (Urbani strain)

<400> SEQUENCE: 13
ttattaggtt tttacctacc caggaaaagc caaccaacct cgatctcttg tagatctgtt 60
ctctaaacga actttaaaat ctgtgtagct gtcgctcggc tgcatgccta gtgcacctac 120
gcagtataaa caataataaa ttttactgtc gttgacaaga aacgagtaac tcgtccctct 180
tctgcagact gcttacggtt tcgtccgtgt tgcagtcgat catcagcata cctaggtttc 240
gtccgggtgt gaccgaaagg taagatggag agccttgttc ttggtgtcaa cgagaaaaca 300
cacgtccaac tcagtttgcc tgtccttcag gttagagacg tgctagtgcg tggcttcggg 360
gactctgtgg aagaggccct atcggaggca cgtgaacacc tcaaaaatgg cacttgtggt 420
ctagtagagc tggaaaaagg cgtactgccc cagcttgaac agccctatgt gttcattaaa 480
cgttctgatg ccttaagcac caatcacggc cacaaggtcg ttgagctggt tgcagaaatg 540
gacggcattc agtacggtcg tagcggtata acactgggag tactcgtgcc acatgtgggc 600
gaaaccccaa ttgcataccg caatgttctt cttcgtaaga acggtaataa gggagccggt 660
ggtcatagct atggcatcga tctaaagtct tatgacttag gtgacgagct tggcactgat 720
cccattgaag attatgaaca aaactggaac actaagcatg gcagtggtgc actccgtgaa 780
ctcactcgtg agctcaatgg aggtgcagtc actcgctatg tcgacaacaa tttctgtggc 840
ccagatgggt accctcttga ttgcatcaaa gattttctcg cacgcgcggg caagtcaatg 900
tgcactcttt ccgaacaact tgattacatc gagtcgaaga gaggtgtcta ctgctgccgt 960
gaccatgagc atgaaattgc ctggttcact gagcgctctg ataagagcta cgagcaccag 1020
acacccttcg aaattaagag tgccaagaaa tttgacactt tcaaagggga atgcccaaag 1080

```
tttgtgtttc ctcttaactc aaaagtcaaa gtcattcaac cacgtgttga aaagaaaaag   1140
actgagggtt tcatggggcg tatacgctct gtgtaccctg ttgcatctcc acaggagtgt   1200
aacaatatgc acttgtctac cttgatgaaa tgtaatcatt gcgatgaagt ttcatggcag   1260
acgtgcgact ttctgaaagc cacttgtgaa cattgtggca ctgaaaattt agttattgaa   1320
ggacctacta catgtgggta cctacctact aatgctgtag tgaaaatgcc atgtcctgcc   1380
tgtcaagacc cagagattgg acctgagcat agtgttgcag attatcacaa ccactcaaac   1440
attgaaactc gactccgcaa gggaggtagg actagatgtt ttggaggctg tgtgtttgcc   1500
tatgttggct gctataataa gcgtgcctac tgggttcctc gtgctagtgc tgatattggc   1560
tcaggccata ctggcattac tggtgacaat gtggagacct gaatgagga tctccttgag    1620 atactgagtc gtgaacgtgt taacattaac attgttggcg attttcattt gaatgaagag   1680
gttgccatca ttttggcatc tttctctgct tctacaagtg cctttattga cactataaag   1740
agtcttgatt acaagtcttt caaaaccatt gttgagtcct gcggtaacta taagttacc    1800 aagggaaagc ccgtaaaagg tgcttggaac attggacaac agagatcagt tttaacacca   1860
ctgtgtggtt ttccctcaca ggctgctggt gttatcagat caattttgc gcgcacactt    1920 gatgcagcaa accactcaat tcctgatttg caaagagcag ctgtcaccat acttgatggt   1980
atttctgaac agtcattacg tcttgtcgac gccatggttt atacttcaga cctgctcacc   2040
aacagtgtca ttattatggc atatgtaact ggtggtcttg tacaacagac ttctcagtgg   2100
ttgtctaatc ttttgggcac tactgttgaa aaactcaggc ctatctttga atggattgag   2160
gcgaaactta gtgcaggagt tgaatttctc aaggatgctt gggagattct caaatttctc   2220
attacaggtg tttttgacat cgtcaagggt caaatacagg ttgcttcaga taacatcaag   2280
gattgtgtaa atgcttcat tgatgttgtt aacaaggcac tcgaaatgtg cattgatcaa    2340
gtcactatcg ctggcgcaaa gttgcgatca ctcaacttag tgaagtctt catcgctcaa    2400 agcaagggac tttaccgtca gtgtatacgt ggcaaggagc agctgcaact actcatgcct   2460
cttaaggcac caaaagaagt aacctttctt gaaggtgatt cacatgacac agtacttacc   2520
tctgaggagg ttgttctcaa gaacggtgaa ctcgaagcac tcgagacgcc cgttgatagc   2580
ttcacaaatg gagctatcgt tggcacacca gtctgtgtaa atggcctcat gctcttagag   2640
attaaggaca agaacaata ctgcgcattg tctcctggtt tactggctac aaacaatgtc    2700
tttcgcttaa agggggtgc accaattaaa ggtgtaacct ttggagaaga tactgtttgg   2760
gaagttcaag gttacaagaa tgtgagaatc acatttgagc ttgatgaacg tgttgacaaa   2820
gtgcttaatg aaaagtgctc tgtctacact gttgaatccg gtaccgaagt tactgagttt   2880
gcatgtgttg tagcagaggc tgttgtgaag acttacaac cagtttctga tctccttacc    2940
aacatgggta ttgatcttga tgagtggagt gtagctacat tctacttatt tgatgatgct   3000
ggtgaagaaa actttctcatc acgtatgtat tgttcctttt accctccaga tgaggaagaa   3060
gaggacgatg cagagtgtga ggaagaagaa attgatgaaa cctgtgaaca tgagtacggt   3120
acagaggatg attatcaagg tctccctctg gaatttggtg cctcagctga aacagttcga   3180
gttgaggaag aagaaggaga agactggctg gatgatacta ctgagcaatc agagattgag   3240
ccagaaccag aacctacacc tgaagaacca gttaatcagt ttactggtta tttaaaactt   3300
actgacaatg ttgccattaa atgtgttgac atcgttaagg aggcacaaag tgctaatcct   3360
atggtgattt aaatgctgc taacatacac ctgaaacatg gtggtggtgt agcaggtgca   3420
ctcaacaagg caaccaatgg tgccatgcaa aaggagagtg atgattacat taagctaaat   3480
```

```
ggccctctta cagtaggagg gtcttgtttg ctttctggac ataatcttgc taagaagtgt    3540
ctgcatgttg ttggacctaa cctaaatgca ggtgaggaca tccagcttct taaggcagca    3600
tatgaaaatt tcaattcaca ggacatctta cttgcaccat tgttgtcagc aggcatattt    3660
ggtgctaaac cacttcagtc tttacaagtg tgcgtgcaga cggttcgtac acaggtttat    3720
attgcagtca atgacaaagc tctttatgag caggttgtca tggattatct tgataacctg    3780
aagcctagag tggaagcacc taaacaagag gagccaccaa acacagaaga ttccaaaact    3840
gaggagaaat ctgtcgtaca gaagcctgtc gatgtgaagc aaaaattaa ggcctgcatt     3900 gatgaggtta ccacaacact ggaagaaact aagtttctta ccaataagtt actcttgttt    3960
gctgatatca atggtaagct ttaccatgat tctcagaaca tgcttagagg tgaagatatg    4020
tctttccttg agaaggatgc accttacatg gtaggtgatg ttatcactag tggtgatatc    4080
acttgtgttg taatacccte caaaaaggct ggtggcacta ctgagatgct ctcaagagct    4140
ttgaagaaag tgccagttga tgagtatata accacgtacc ctggacaagg atgtgctggt    4200
tatacacttg aggaagctaa gactgctctt aagaaatgca atctgcatt ttatgtacta     4260 ccttcagaag cacctaatgc taaggaagag attctaggaa ctgtatcctg gaatttgaga    4320
gaaatgcttg ctcatgctga agagacaaga aaattaatgc ctatatgcat ggatgttaga    4380
gccataatgg caaccatcca acgtaagtat aaaggaatta aaattcaaga gggcatcgtt    4440
gactatggtg tccgattctt cttttatact agtaaagagc ctgtagcttc tattattacg    4500
aagctgaact ctctaaatga gccgcttgtc acaatgccaa ttggttatgt gacacatggt    4560
tttaatcttg aagaggctgc gcgctgtatg cgttctctta agctcctgc cgtagtgtca     4620 gtatcatcac cagatgctgt tactacatat aatggatacc tcacttcgtc atcaaagaca    4680
tctgaggagc actttgtaga aacagtttct ttggctggct cttacagaga ttggtcctat    4740
tcaggacagc gtacagagtt aggtgttgaa tttcttaagc gtggtgacaa aattgtgtac    4800
cacactctgg agagccccgt cgagtttcat cttgacggtg aggttctttc acttgacaaa    4860
ctaaagagtc tcttatccct gcgggaggtt aagactataa agtgttcac aactgtggac     4920 aacactaatc tccacacaca gcttgtggat atgtctatga catatggaca gcagtttggt    4980
ccaacatact tggatggtgc tgatgttaca aaaattaaac ctcatgtaaa tcatgagggt    5040
aagactttct ttgtactacc tagtgatgac acactacgta gtgaagcttt cgagtactac    5100
catactcttg atgagagttt tcttggtagg tacatgtctg cttttaaacca cacaaagaaa    5160 tggaaatttc ctcaagttgg tggtttaact tcaattaaat gggctgataa caattgttat    5220
ttgtctagtt ttttattagc acttcaacag cttgaagtca aattcaatgc accagcactt    5280
caagaggctt attatagagc ccgtgctggt gatgctgcta acttttgtgc actcatactc    5340
gcttacagta ataaaactgt tggcgagctt ggtgatgtca gagaaactat gacccatctt    5400
ctacagcatg ctaatttgga atctgcaaag cgagttctta atgtggtgtg taaacattgt    5460
ggtcagaaaa ctactacctt aacgggtgta gaagctgtga tgtatatggg tactctatct    5520
tatgataatc ttaagacagg tgtttccatt ccatgtgtgt gtggtcgtga tgctacacaa    5580
tatctagtac aacaagagtc ttcttttgtt atgatgtctg caccacctgc tgagtataaa    5640
ttacagcaag gtacattctt atgtgcgaat gagtacactg gtaactatca gtgtggtcat    5700
tacactcata taactgctaa ggagacccte tatcgtattg acggagctca ccttacaaag    5760
atgtcagagt acaaaggacc agtgactgat gttttctaca aggaaacatc ttacactaca    5820
```

```
accatcaagc ctgtgtcgta taaactcgat ggagttactt acacagagat tgaaccaaaa    5880
ttggatgggt attataaaaa ggataatgct tactatacag agcagcctat agaccttgta    5940
ccaactcaac cattaccaaa tgcgagtttt gataatttca aactcacatg ttctaacaca    6000
aaatttgctg atgatttaaa tcaaatgaca ggcttcacaa agccagcttc acgagagcta    6060
tctgtcacat tcttcccaga cttgaatggc gatgtagtgg ctattgacta tagacactat    6120
tcagcgagtt tcaagaaagg tgctaaatta ctgcataagc caattgtttg gcacattaac    6180
caggctacaa ccaagacaac gttcaaacca acacttggt gtttacgttg tctttggagt    6240
acaaagccag tagatacttc aaattcattt gaagttctgg cagtagaaga cacacaagga    6300
atggacaatc ttgcttgtga aagtcaacaa cccacctctg aagaagtagt ggaaaatcct    6360
accatacaga aggaagtcat agagtgtgac gtgaaaacta ccgaagttgt aggcaatgtc    6420
atacttaaac catcagatga aggtgttaaa gtaacacaag agttaggtca tgaggatctt    6480
atggctgctt atgtggaaaa cacaagcatt accattaaga aacctaatga gctttcacta    6540
gccttaggtt taaaaacaat tgccactcat ggtattgctg caattaatag tgttccttgg    6600
agtaaaattt tggcttatgt caaaccattc ttaggacaag cagcaattac aacatcaaat    6660
tgcgctaaga gattagcaca acgtgtgttt aacaattata tgccttatgt gtttacatta    6720
ttgttccaat tgtgtacttt tactaaaagt accaattcta gaattagagc ttcactacct    6780
acaactattg ctaaaaatag tgttaagagt gttgctaaat tatgtttgga tgccggcatt    6840
aattatgtga agtcacccaa attttctaaa ttgttcacaa tcgctatgtg gctattgttg    6900
ttaagtattt gcttaggttc tctaatctgt gtaactgctg cttttggtgt actcttatct    6960
aattttggtg ctccttctta ttgtaatggc gttagagaat tgtatcttaa ttcgtctaac    7020
gttactacta tggatttctg tgaaggttct tttccttgca gcatttgttt aagtggatta    7080
gactcccttg attcttatcc agctcttgaa accattcagg tgacgatttc atcgtacaag    7140
ctagacttga caattttagg tctggccgct gagtgggttt tggcatatat gttgttcaca    7200
aaattctttt atttattagg tctttcagct ataatgcagg tgttctttgg ctattttgct    7260
agtcatttca tcagcaattc ttggctcatg tggtttatca ttagtattgt acaaatggca    7320
cccgttctg caatggttag gatgtacatc ttctttgctt cttctactat catatggaag    7380
agctatgttc atatcatgga tggttgcacc tcttcgactt gcatgatgtg ctataagcgc    7440
aatcgtgcca cacgcgttga gtgtacaact attgttaatg gcatgaagag atctttctat    7500
gtctatgcaa atggaggccg tggcttctgc aagactcaca attggaattg tctcaattgt    7560
gacacatttt gcactggtag tacattcatt agtgatgaag ttgctcgtga tttgtcactc    7620
cagtttaaaa gaccaatcaa ccctactgac cagtcatcgt atattgttga tagtgttgct    7680
gtgaaaaatg cgcgcttca cctctacttt gacaaggctg tcaaaagac ctatgagaga    7740
catccgctct cccatttgt caatttagac aatttgagag ctaacaacac taaaggttca    7800
ctgcctatta atgtcatagt ttttgatggc aagtccaaat gcgacgagtc tgcttctaag    7860
tctgcttctg tgtactacag tcagctgatg tgccaaccta ttctgttgct tgaccaagtt    7920
cttgtatcag acgttggaga tagtactgaa gtttccgtta agatgtttga tgcttatgtc    7980
gacacctttt cagcaacttt tagtgttcct atggaaaaac ttaaggcact tgttgctaca    8040
gctcacagcg agttagcaaa gggtgtagct ttagatggtg tcctttctac attcgtgtca    8100
gctgcccgac aaggtgttgt tgataccgat gttgacacaa aggatgttat tgaatgtctc    8160
aaactttcac atcactctga cttagaagtg acaggtgaca gttgtaacaa tttcatgctc    8220
```

```
acctataata aggttgaaaa catgacgccc agagatcttg gcgcatgtat tgactgtaat    8280
gcaaggcata tcaatgccca agtagcaaaa agtcacaatg tttcactcat ctggaatgta    8340
aaagactaca tgtctttatc tgaacagctg cgtaaacaaa ttcgtagtgc tgccaagaag    8400
aacaacatac cttttagact aacttgtgct acaactagac aggttgtcaa tgtcataact    8460
actaaaatct cactcaaggg tggtaagatt gttagtactt gttttaaact tatgcttaag    8520
gccacattat tgtgcgttct tgctgcattg gtttgttata tcgttatgcc agtacataca    8580
ttgtcaatcc atgatggtta cacaaatgaa atcattggtt acaaagccat tcaggatggt    8640
gtcactcgtg acatcatttc tactgatgat tgttttgcaa ataaacatgc tggttttgac    8700
gcatggttta gccagcgtgg tggttcatac aaaaatgaca aaagctgccc tgtagtagct    8760
gctatcatta caagagagat tggtttcata gtgcctggct taccgggtac tgtgctgaga    8820
gcaatcaatg tgacttcttg cattttcta cctcgtgttt ttagtgctgt tgcaacatt    8880 tgctacacac cttccaaact cattgagtat agtgattttg ctacctctgc ttgcgttctt    8940
gctgctgagt gtacaatttt taaggatgct atgggcaaac ctgtgccata ttgttatgac    9000
actaatttgc tagagggttc tatttcttat agtgagcttc gtccagacac tcgttatgtg    9060
cttatggatg gttccatcat acagtttcct aacacttacc tggagggttc tgttagagta    9120
gtaacaactt ttgatgctga gtactgtaga catggtacat gcgaaaggtc agaagtaggt    9180
atttgcctat ctaccagtgg tagatgggtt cttaataatg agcattacag agctctatca    9240
ggagttttct gtggtgttga tgcgatgaat ctcatagcta acatctttac tcctcttgtg    9300
caacctgtgg gtgctttaga tgtgtctgct tcagtagtgg ctggtggtat tattgccata    9360
ttggtgactt gtgctgccta ctactttatg aaattcagac gtgtttttgg tgagtacaac    9420
catgttgttg ctgctaatgc acttttgttt ttgatgtctt tcactatact ctgtctggta    9480
ccagcttaca gctttctgcc gggagtctac tcagtctttt acttgtactt gacattctat    9540
ttcaccaatg atgtttcatt cttggctcac cttcaatggt ttgccatgtt ttctcctatt    9600
gtgccttttt ggataacagc aatctatgta ttctgtattt ctctgaagca ctgccattgg    9660
ttctttaaca actatcttag gaaaagagtc atgtttaatg gagttacatt tagtaccttc    9720
gaggaggctg ctttgtgtac cttttttgctc aacaaggaaa tgtacctaaa attgcgtagc    9780
gagacactgt tgccacttac acagtataac aggtatcttg ctctatataa caagtacaag    9840
tatttcagtg gagccttaga tactaccagc tatcgtgaag cagcttgctg ccacttagca    9900
aaggctctaa atgactttag caactcaggt gctgatgttc tctaccaacc accacagaca    9960
tcaatcactt ctgctgttct gcagagtggt tttaggaaaa tggcattccc gtcaggcaaa    10020
gttgaagggt gcatggtaca agtaacctgt ggaactacaa ctcttaatgg attgtggttg    10080
gatgacacag tatactgtcc aagacatgtc atttgcacag cagaagacat gcttaatcct    10140
aactatgaag atctgctcat tcgcaaatcc aaccatagct ttcttgttca ggctggcaat    10200
gttcaacttc gtgttattgg ccattctatg caaaattgtc tgcttaggct taaagttgat    10260
acttctaacc ctaagacacc caagtataaa tttgtccgta tccaacctgg tcaaacattt    10320
tcagttctag catgctacaa tggttcacca tctggtgttt atcagtgtgc catgagacct    10380
aatcatacca ttaaaggttc tttccttaat ggatcatgtg gtagtgttgg ttttaacatt    10440
gattatgatt gcgtgtcttt ctgctatatg catcatatgg agcttccaac aggagtacac    10500
gctggtactg acttagaagg taaattctat ggtccatttg ttgacagaca aactgcacag    10560
```

| | | | | | |
|---|---|---|---|---|---|
| gctgcaggta | cagacacaac | cataacatta | aatgttttgg | catggctgta | tgctgctgtt | 10620 |
| atcaatggtg | ataggtggtt | tcttaataga | ttcaccacta | ctttgaatga | ctttaacctt | 10680 |
| gtggcaatga | agtacaacta | tgaaccttg | acacaagatc | atgttgacat | attgggacct | 10740 |
| cttctgctc | aaacaggaat | tgccgtctta | gatatgtgtg | ctgctttgaa | agagctgctg | 10800 |
| cagaatggta | tgaatggtcg | tactatcctt | ggtagcacta | ttttagaaga | tgagtttaca | 10860 |
| ccatttgatg | ttgttagaca | atgctctggt | gttaccttcc | aaggtaagtt | caagaaaatt | 10920 |
| gttaagggca | ctcatcattg | gatgctttta | actttcttga | catcactatt | gattcttgtt | 10980 |
| caaagtacac | agtggtcact | gttttctctt | gtttacgaga | atgctttctt | gccatttact | 11040 |
| cttggtatta | tggcaattgc | tgcatgtgct | atgctgcttg | ttaagcataa | gcacgcattc | 11100 |
| ttgtgcttgt | ttctgttacc | ttctcttgca | acagttgctt | actttaatat | ggtctacatg | 11160 |
| cctgctagct | gggtgatgcg | tatcatgaca | tggcttgaat | tggctgacac | tagcttgtct | 11220 |
| ggttataggc | ttaaggattg | tgttatgtat | gcttcagctt | tagttttgct | tattctcatg | 11280 |
| acagctcgca | ctgtttatga | tgatgctgct | agacgtgttt | ggacactgat | gaatgtcatt | 11340 |
| acacttgttt | acaaagtcta | ctatggtaat | gctttagatc | aagctatttc | catgtgggcc | 11400 |
| ttagttattt | ctgtaaccct | taactattct | ggtgtcgtta | cgactatcat | gttttagct | 11460 |
| agagctatag | tgtttgtgtg | tgttgagtat | tacccattgt | tatttattac | tggcaacacc | 11520 |
| ttacagtgta | tcatgcttgt | ttattgtttc | ttaggctatt | gttgctgctg | ctactttggc | 11580 |
| cttttctgtt | tactcaaccg | ttacttcagg | cttactcttg | gtgtttatga | ctacttggtc | 11640 |
| tctacacaag | aatttaggta | tatgaactcc | caggggcttt | tgcctcctaa | gagtagtatt | 11700 |
| gatgctttca | agcttaacat | taagttgttg | ggtattggag | gtaaaccatg | tatcaaggtt | 11760 |
| gctactgtac | agtctaaaat | gtctgacgta | aagtgcacat | ctgtggtact | gctctcggtt | 11820 |
| cttcaacaac | ttagagtaga | gtcatcttct | aaattgtggg | cacaatgtgt | acaactccac | 11880 |
| aatgatattc | ttcttgcaaa | agacacaact | gaagctttcg | agaagatggt | ttctcttttg | 11940 |
| tctgttttgc | tatccatgca | gggtgctgta | gacattaata | ggttgtgcga | ggaaatgctc | 12000 |
| gataaccgtg | ctactcttca | ggctattgct | tcagaattta | gttctttacc | atcatatgcc | 12060 |
| gcttatgcca | ctgcccagga | ggcctatgag | caggctgtag | ctaatggtga | ttctgaagtc | 12120 |
| gttctcaaaa | agttaaagaa | atctttgaat | gtggctaaat | ctgagtttga | ccgtgatgct | 12180 |
| gccatgcaac | gcaagttgga | aaagatggca | gatcaggcta | tgacccaaat | gtacaaacag | 12240 |
| gcaagatctg | aggacaagag | ggcaaaagta | actagtgcta | tgcaaacaat | gctcttcact | 12300 |
| atgcttagga | agcttgataa | tgatgcactt | aacaacatta | tcaacaatgc | gcgtgatggt | 12360 |
| tgtgttccac | tcaacatcat | accattgact | acagcagcca | aactcatggt | tgttgtccct | 12420 |
| gattatggta | cctacaagaa | cacttgtgat | ggtaacacct | ttacatatgc | atctgcactc | 12480 |
| tgggaaatcc | agcaagttgt | tgatgcggat | agcaagatt | ttcaacttag | tgaaattaac | 12540 |
| atggacaatt | caccaaattt | ggcttggcct | cttattgtta | cagctctaag | agccaactca | 12600 |
| gctgttaaac | tacagaataa | tgaactgagt | ccagtagcac | tacgacagat | gtcctgtgcg | 12660 |
| gctggtacca | cacaaacagc | ttgtactgat | gacaatgcac | ttgcctacta | taacaattcg | 12720 |
| aagggaggta | ggtttgtgct | ggcattacta | tcagaccacc | aagatctcaa | atgggctaga | 12780 |
| ttccctaaga | gtgatggtac | aggtacaatt | tacacagaac | tggaaccacc | ttgtaggttt | 12840 |
| gttacagaca | caccaaaagg | gcctaaagtg | aaatacttgt | acttcatcaa | aggcttaaac | 12900 |
| aacctaaata | gaggtatggt | gctgggcagt | ttagctgcta | cagtacgtct | tcaggctgga | 12960 |

```
aatgctacag aagtacctgc caattcaact gtgctttcct tctgtgcttt tgcagtagac   13020
cctgctaaag catataagga ttacctagca agtggaggac aaccaatcac caactgtgtg   13080
aagatgttgt gtacacacac tggtacagga caggcaatta ctgtaacacc agaagctaac   13140
atggaccaag agtcctttgg tggtgcttca tgttgtctgt attgtagatg ccacattgac   13200
catccaaatc ctaaaggatt ctgtgacttg aaaggtaagt acgtccaaat acctaccact   13260
tgtgctaatg acccagtggg ttttacactt agaaacacag tctgtaccgt ctgcggaatg   13320
tggaaaggtt atggctgtag ttgtgaccaa ctccgcgaac ccttgatgca gtctgcggat   13380
gcatcaacgt ttttaaacgg gtttgcggtg taagtgcagc ccgtcttaca ccgtgcggca   13440
caggcactag tactgatgtc gtctacaggg cttttgatat ttacaacgaa aaagttgctg   13500
gttttgcaaa gttcctaaaa actaattgct gtcgcttcca ggagaaggat gaggaaggca   13560
atttattaga ctcttacttt gtagttaaga ggcatactat gtctaactac caacatgaag   13620
agactattta taacttggtt aaagattgtc cagcggttgc tgtccatgac tttttcaagt   13680
ttagagtaga tggtgacatg gtaccacata tatcacgtca gcgtctaact aaatacacaa   13740
tggctgattt agtctatgct ctacgtcatt ttgatgaggg taattgtgat acattaaaag   13800
aaatactcgt cacatacaat tgctgtgatg atgattattt caataagaag gattggtatg   13860
acttcgtaga gaatcctgac atcttacgcg tatatgctaa cttaggtgag cgtgtacgcc   13920
aatcattatt aaagactgta caattctgcg atgctatgcg tgatgcaggc attgtaggcg   13980
tactgacatt agataatcag gatcttaatg ggaactggta cgatttcggt gatttcgtac   14040
aagtagcacc aggctgcgga gttcctattg tggattcata ttactcattg ctgatgccca   14100
tcctcacttt gactagggca ttggctgctg agtcccatat ggatgctgat tctcgcaaaac   14160 cacttattaa gtgggatttg ctgaaatatg attttacgga agagagactt gtctcttcg   14220 accgttattt taaatattgg gaccagacat accatcccaa ttgtattaac tgtttggatg   14280
ataggtgtat ccttcattgt gcaaacttta atgtgttatt ttctactgtg tttccaccta   14340
caagttttgg accactagta agaaaaatat ttgtagatgg tgttcctttt gttgtttcaa   14400
ctggatacca ttttcgtgag ttaggagtcg tacataatca ggatgtaaac ttacatagct   14460
cgcgtctcag ttttcaaggaa cttttagtgt atgctgctga tccagctatg catgcagctt   14520
ctggcaattt attgctagat aaacgcacta catgctttc agtagctgca ctaacaaaca   14580
atgttgcttt tcaaactgtc aaacccggta atttaataa agacttttat gactttgctg   14640
tgtctaaagg tttctttaag gaaggaagtt ctgttgaact aaaacacttc ttctttgctc   14700
aggatggcaa cgctgctatc agtgattatg actattatcg ttataatctg ccaacaatgt   14760
gtgatatcag acaactccta ttcgtagttg aagttgttga taaatacttt gattgttacg   14820
atggtggctg tattaatgcc aaccaagtaa tcgttaacaa tctggataaa tcagctggtt   14880
tcccatttaa taaatggggt aaggctagac tttattatga ctcaatgagt tatgaggatc   14940
aagatgcact tttcgcgtat actaagcgta atgtcatccc tactataact caaatgaatc   15000
ttaagtatgc cattagtgca aagaatagag ctcgcaccgt agctggtgtc tctatctgta   15060
gtactatgac aaatagacag tttcatcaga aattattgaa gtcaatagcc gccactagag   15120
gagctactgt ggtaattgga acaagcaagt tttacggtgg ctggcataat atgttaaaaa   15180
ctgtttacag tgatgtagaa actccacacc ttatggggtg ggattatcca aaatgtgaca   15240
gagccatgcc taacatgctt aggataatgg cctctcttgt tcttgctcgc aaacataaca   15300
```

```
cttgctgtaa cttatcacac cgtttctaca ggttagctaa cgagtgtgcg caagtattaa   15360
gtgagatggt catgtgtggc ggctcactat atgttaaacc aggtggaaca tcatccggtg   15420
atgctacaac tgcttatgct aatagtgtct ttaacatttg tcaagctgtt acagccaatg   15480
taaatgcact tctttcaact gatggtaata agatagctga caagtatgtc cgcaatctac   15540
aacacaggct ctatgagtgt ctctatagaa atagggatgt tgatcatgaa ttcgtggatg   15600
agttttacgc ttacctgcgt aaacatttct ccatgatgat tctttctgat gatgccgttg   15660
tgtgctataa cagtaactat gcggctcaag gtttagtagc tagcattaag aactttaagg   15720
cagttcttta ttatcaaaat aatgtgttca tgtctgaggc aaaatgttgg actgagactg   15780
accttactaa aggacctcac gaattttgct cacagcatac aatgctagtt aaacaaggag   15840
atgattacgt gtacctgcct tacccagatc catcaagaat attaggcgca ggctgttttg   15900
tcgatgatat tgtcaaaaca gatggtacac ttatgattga aggttcgtg tcactggcta   15960 ttgatgctta cccacttaca aaacatccta atcaggagta tgctgatgtc tttcacttgt   16020
atttacaata cattagaaag ttacatgatg agcttactgg ccacatgttg gacatgtatt   16080
ccgtaatgct aactaatgat aacacctcac ggtactggga acctgagttt tatgaggcta   16140
tgtacacacc acatacagtc ttgcaggctg taggtgcttg tgtattgtgc aattcacaga   16200
cttcacttcg ttgcggtgcc tgtattagga gaccattcct atgttgcaag tgctgctatg   16260
accatgtcat ttcaacatca cacaaattag tgttgtctgt taatcccta t gtttgcaatg   16320 ccccaggttg tgatgtcact gatgtgacac aactgtatct aggaggtatg agctattatt   16380
gcaagtcaca taagcctccc attagttttc cattatgtgc taatggtcag ttttttggtt   16440
tatacaaaaa cacatgtgta ggcagtgaca atgtcactga cttcaatgcg atagcaacat   16500
gtgattggac taatgctggc gattacatac ttgccaacac ttgtactgag agactcaagc   16560
ttttcgcagc agaaacgctc aaagccactg aggaaacatt taagctgtca tatggtattg   16620
ctactgtacg cgaagtactc tctgacagag aattgcatct ttcatgggag gttggaaaac   16680
ctagaccacc attgaacaga aactatgtct ttactggtta ccgtgtaact aaaaatagta   16740
aagtacagat tggagagtac acctttgaaa aaggtgacta tggtgatgct gttgtgtaca   16800
gaggtactac gacatacaag ttgaatgttg gtgattactt tgtgttgaca tctcacactg   16860
taatgccact tagtgcacct actctagtgc cacaagagca ctatgtgaga attactggct   16920
tgtacccaac actcaacatc tcagatgagt tttctagcaa tgttgcaaat tatcaaaagg   16980
tcggcatgca aaagtactct acactccaag gaccacctgg tactggtaag agtcattttg   17040
ccatcggact tgctctctat tacccatctg ctcgcatagt gtatacggca tgctctcatg   17100
cagctgttga tgcccctatgt gaaaaggcat taaaatattt gcccatagat aaatgtagta   17160
gaatcatacc tgcgcgtgcg cgcgtagagt gttttgataa attcaaagtg aattcaacac   17220
tagaacagta tgttttctgc actgtaaatg cattgccaga acaactgct gacattgtag   17280 tctttgatga aatctctatg gctactaatt atgacttgag tgttgtcaat gctagacttc   17340
gtgcaaaaca ctacgtctat attggcgatc ctgctcaatt accagcccc cgcacattgc   17400 tgactaaagg cacactagaa ccagaatatt ttaattcagt gtgcagactt atgaaaacaa   17460
taggtccaga catgttcctt ggaacttgtc gccgttgtcc tgctgaaatt gttgacactg   17520
tgagtgcttt agtttatgac aataagctaa agcacacaa ggataagtca gctcaatgct   17580
tcaaaatgtt ctacaaaggt gttattacac atgatgtttc atctgcaatc aacagacctc   17640
aaataggcgt tgtaagagaa tttcttacac gcaatcctgc ttggagaaaa gctgttttta   17700
```

```
tctcaccttaa taattcacag aacgctgtag cttcaaaaat cttaggattg cctacgcaga    17760
ctgttgattc atcacagggt tctgaatatg actatgtcat attcacacaa actactgaaa    17820
cagcacactc ttgtaatgtc aaccgcttca atgtggctat cacaagggca aaaattggca    17880
ttttgtgcat aatgtctgat agagatcttt atgacaaact gcaatttaca agtctagaaa    17940
taccacgtcg caatgtggct acattacaag cagaaaatgt aactggactt tttaaggact    18000
gtagtaagat cattactggt cttcatccta cacaggcacc tacacacctc agcgttgata    18060
taaagttcaa gactgaagga ttatgtgttg acataccagg cataccaaag gacatgacct    18120
accgtagact catctctatg atgggtttca aaatgaatta ccaagtcaat ggttacccta    18180
atatgtttat cacccgcgaa gaagctattc gtcacgttcg tgcgtggatt ggctttgatg    18240
tagagggctg tcatgcaact agagatgctg tgggtactaa cctacctctc cagctaggat    18300
tttctacagg tgttaactta gtagctgtac cgactggtta tgttgacact gaaaataaca    18360
cagaattcac cagagttaat gcaaaacctc caccaggtga ccagtttaaa catcttatac    18420
cactcatgta taaaggcttg ccctggaatg tagtgcgtat taagatagta caaatgctca    18480
gtgatacact gaaaggattg tcagacagag tcgtgttcgt cctttgggcg catggctttg    18540
agcttacatc aatgaagtac tttgtcaaga ttggacctga agaacgtgt tgtctgtgtg    18600 acaaacgtgc aacttgcttt tctacttcat cagatactta tgcctgctgg aatcattctg    18660
tgggttttga ctatgtctat aacccattta tgattgatgt tcagcagtgg ggctttacgg    18720
gtaaccttca gagtaaccat gaccaacatt gccaggtaca tggaaatgca catgtggcta    18780
gttgtgatgc tatcatgact agatgtttag cagtccatga gtgctttgtt aagcgcgttg    18840
attggtctgt tgaataccct attataggag atgaactgag ggttaattct gcttgcagaa    18900
aagtacaaca catggttgtg aagtctgcat tgcttgctga taagtttcca gttcttcatg    18960
acattggaaa tccaaaggct atcaagtgtg tgcctcaggc tgaagtagaa tggaagttct    19020
acgatgctca gccatgtagt gacaaagctt acaaaataga ggagctcttc tattcttatg    19080
ctacacatca cgataaattc actgatggtg tttgtttgtt ttggaattgt aacgttgatc    19140
gttacccagc caatgcaatt gtgtgtaggt ttgacacaag agccttgtca aacttgaact    19200
taccaggctg tgatggtggt agtttgtatg tgaataagca tgcattccac actccagctt    19260
tcgataaaag tgcatttact aatttaaagc aattgccttt ctttactat tctgatagtc    19320 cttgtgagtc tcatggcaaa caagtagtgt cggatattga ttatgttcca ctcaaatctg    19380
ctacgtgtat tacacgatgc aatttaggtg gtgctgtttg cagacaccat gcaaatgagt    19440
accgacagta cttggatgca tataatatga tgatttctgc tggatttagc ctatggattt    19500
acaaacaatt tgatacttat aacctgtgga atacatttac caggttacag agtttagaaa    19560
atgtggctta taatgttgtt aataaaggac actttgatgg acacgccggc gaagcacctg    19620
tttccatcat taataatgct gtttacacaa aggtagatgg tattgatgtg gagatctttg    19680
aaaataagac aacacttcct gttaatgttg catttgagct ttgggctaag cgtaacatta    19740
aaccagtgcc agagattaag atactcaata atttgggtgt tgatatcgct gctaatactg    19800
taatctggga ctacaaaaga gaagcccag cacatgtatc tacaataggt gtctgcacaa    19860
tgactgacat tgccaagaaa cctactgaga gtgcttgttc ttcacttact gtcttgtttg    19920
atggtagagt ggaaggacag gtagaccttt ttagaaacgc ccgtaatggt gttttaataa    19980
cagaaggttc agtcaaaggt ctaacacctt caaagggacc agcacaagct agcgtcaatg    20040
```

```
gagtcacatt aattggagaa tcagtaaaaa cacagtttaa ctactttaag aaagtagacg    20100
gcattattca acagttgcct gaaacctact ttactcagag cagagactta gaggatttta    20160
agcccagatc acaaatggaa actgactttc tcgagctcgc tatggatgaa ttcatacagc    20220
gatataagct cgagggctat gccttcgaac acatcgttta tggagatttc agtcatggac    20280
aacttggcgg tcttcattta atgataggct tagccaagcg ctcacaagat tcaccactta    20340 aattgagga ttttatccct atggacagca cagtgaaaaa ttacttcata acagatgcgc    20400
aaacaggttc atcaaaatgt gtgtgttctg tgattgatct tttacttgat gactttgtcg    20460
agataataaa gtcacaagat ttgtcagtga tttcaaaagt ggtcaaggtt acaattgact    20520
atgctgaaat tcattcatg ctttggtgta aggatggaca tgttgaaacc ttctacccaa    20580
aactacaagc aagtcaagcg tggcaaccag gtgttgcgat gcctaacttg tacaagatgc    20640
aaagaatgct tcttgaaaag tgtgaccttc agaattatgg tgaaaatgct gttataccaa    20700
aaggaataat gatgaatgtc gcaaagtata ctcaactgtg tcaatactta aatacactta    20760
ctttagctgt accctacaac atgagagtta ttcactttgg tgctggctct gataaaggag    20820
ttgcaccagg tacagctgtg ctcagacaat ggttgccaac tggcacacta cttgtcgatt    20880
cagatcttaa tgacttcgtc tccgacgcag attctacttt aattggagac tgtgcaacag    20940
tacatacggc taataaatgg gaccttatta ttagcgatat gtatgaccct aggaccaaac    21000
atgtgacaaa agagaatgac tctaaagaag ggttttttcac ttatctgtgt ggatttataa    21060
agcaaaaact agccctgggt ggttctatag ctgtaaagat aacagagcat tcttggaatg    21120 ctgacccttta caagcttatg ggccatttct catggtggac agcttttgtt acaaatgtaa    21180
atgcatcatc atcggaagca ttttaattg gggctaacta tcttggcaag ccgaaggaac    21240
aaattgatgg ctataccatg catgctaact acattttctg gaggaacaca aatcctatcc    21300
agttgtcttc ctattcactc tttgacatga gcaaatttcc tcttaaatta agaggaactg    21360
ctgtaatgtc tcttaaggag aatcaaatca atgatatgat ttattctctt ctggaaaaag    21420
gtaggcttat cattagagaa acaacagag ttgtggtttc aagtgatatt cttgttaaca    21480
actaaacgaa catgttatt ttcttattat ttcttactct cactagtggt agtgaccttg    21540
accggtgcac cactttgat gatgttcaag ctcctaatta cactcaacat acttcatcta    21600 tgagggggt ttactatcct gatgaaattt ttagatcaga cactctttat ttaactcagg    21660
atttatttct tccattttat tctaatgtta cagggtttca tactattaat catacgtttg    21720
gcaaccctgt catacctttt aaggatggta tttattttgc tgccacagag aaatcaaatg    21780
ttgtccgtgg ttgggttttt ggttctacca tgaacaacaa gtcacagtcg gtgattatta    21840
ttaacaattc tactaatgtt gttatacgag catgtaactt tgaattgtgt gacaacccctt    21900 tctttgctgt ttctaaaccc atgggtacac agacacatac tatgatattc gataatgcat    21960
ttaattgcac tttcgagtac atatctgatg ccttttcgct tgatgtttca gaaaagtcag    22020
gtaattttaa acacttacga gagtttgtgt ttaaaataa agatgggttt ctctatgttt    22080
ataagggcta tcaacctata gatgtagttc gtgatctacc ttctggtttt aacactttga    22140
aacctatttt taagttgcct cttggtatta acattacaaa ttttagagcc attcttacag    22200 cctttttcacc tgctcaagac atttgggca cgtcagctgc agcctatttt gttggctatt    22260
taaagccaac tacatttatg ctcaagtatg atgaaaatgg tacaatcaca gatgctgttg    22320
attgttctca aaatccactt gctgaactca aatgctctgt taagagcttt gagattgaca    22380
aaggaattta ccagacctct aatttcaggg ttgttccctc aggagatgtt gtgagattcc    22440
```

```
ctaatattac aaacttgtgt cctttggag aggttttaa tgctactaaa ttcccttctg    22500
tctatgcatg ggagagaaaa aaaatttcta attgtgttgc tgattactct gtgctctaca    22560
actcaacatt ttttcaacc tttaagtgct atggcgtttc tgccactaag ttgaatgatc    22620
tttgcttctc caatgtctat gcagattctt ttgtagtcaa gggagatgat gtaagacaaa    22680
tagcgccagg acaaactggt gttattgctg attataatta taaattgcca gatgatttca    22740
tgggttgtgt ccttgcttgg aatactagga acattgatgc tacttcaact ggtaattata    22800
attataaata taggtatctt agacatggca agcttaggcc ctttgagaga gacatatcta    22860
atgtgccttt ctcccctgat ggcaaacctt gcaccccacc tgctcttaat tgttattggc    22920
cattaaatga ttatggtttt tacaccacta ctggcattgg ctaccaacct tacagagttg    22980
tagtactttc ttttgaactt ttaaatgcac cggccacggt ttgtggacca aaattatcca    23040
ctgaccttat taagaaccag tgtgtcaatt ttaatttaa tggactcact ggtactggtg    23100
tgttaactcc ttcttcaaag agatttcaac catttcaaca atttggccgt gatgtttctg    23160
atttcactga ttccgttcga gatcctaaaa catctgaaat attagacatt tcaccttgct    23220
cttttggggg tgtaagtgta attacacctg gaacaaatgc ttcatctgaa gttgctgttc    23280
tatatcaaga tgttaactgc actgatgttt ctacagcaat tcatgcagat caactcacac    23340
cagcttggcg catatattct actggaaaca atgtattcca gactcaagca ggctgtctta    23400
taggagctga gcatgtcgac acttcttatg agtgcgacat tcctattgga gctggcattt    23460
gtgctagtta ccatacagtt tctttattac gtagtactag ccaaaaatct attgtggctt    23520
atactatgtc tttaggtgct gatagttcaa ttgcttactc taataacacc attgctatac    23580
ctactaactt tcaattagc attactacag aagtaatgcc tgtttctatg ctaaaacct    23640
ccgtagattg taatatgtac atctgcggag attctactga atgtgctaat ttgcttctcc    23700
aatatggtag cttttgcaca caactaaatc gtgcactctc aggtattgct gctgaacagg    23760
atcgcaacac acgtgaagtg ttcgctcaag tcaaacaaat gtacaaaacc caactttga    23820
aatattttgg tggttttaat ttttcacaaa tattacctga ccctctaaag ccaactaaga    23880
ggtcttttat tgaggacttg ctctttaata aggtgacact cgctgatgct ggcttcatga    23940
agcaatatgg cgaatgccta ggtgatatta atgctagaga tctcatttgt gcgcagaagt    24000
tcaatggact tacagtgttg ccacctctgc tcactgatga tatgattgct gcctacactg    24060
ctgctctagt tagtggtact gccactgctg gatggacatt tggtgctggc gctgctcttc    24120
aaataccttt tgctatgcaa atggcatata ggttcaatgg cattggagtt acccaaaatg    24180
ttctctatga gaaccaaaaa caaatcgcca accaatttaa caaggcgatt agtcaaattc    24240
aagaatcact tacaacaaca tcaactgcat tgggcaagct gcaagacgtt gttaaccaga    24300
atgctcaagc attaaacaca cttgttaaac aacttagctc taattttggt gcaatttcaa    24360
gtgtgctaaa tgatatcctt tcgcgacttg ataaagtcga ggcggaggta caaattgaca    24420
ggttaattac aggcagactt caaagccttc aaacctatgt aacacaacaa ctaatcaggg    24480
ctgctgaaat cagggcttct gctaatcttg ctgctactaa aatgtctgag tgtgttcttg    24540
gacaatcaaa aagagttgac ttttgtggaa agggctacca ccttatgtcc ttcccacaag    24600
cagccccgca tggtgttgtc ttcctacatg tcacgtatgt gccatcccag agaggaact    24660
tcaccacagc gccagcaatt tgtcatgaag gcaaagcata cttccctcgt gaaggtgttt    24720
ttgtgtttaa tggcacttct tggtttatta cacagaggaa cttctttct ccacaaataa    24780
```

```
ttactacaga caatacattt gtctcaggaa attgtgatgt cgttattggc atcattaaca    24840
acacagttta tgatcctctg caacctgagc tcgactcatt caaagaagag ctggacaagt    24900
acttcaaaaa tcatacatca ccagatgttg atcttggcga catttcaggc attaacgctt    24960
ctgtcgtcaa cattcaaaaa gaaattgacc gcctcaatga ggtcgctaaa aatttaaatg    25020
aatcactcat tgaccttcaa gaattgggaa aatatgagca atatattaaa tggccttggt    25080
atgtttggct cggcttcatt gctggactaa ttgccatcgt catggttaca atcttgcttt    25140
gttgcatgac tagttgttgc agttgcctca agggtgcatg ctcttgtggt tcttgctgca    25200
agtttgatga ggatgactct gagccagttc tcaagggtgt caaattacat tacacataaa    25260
cgaacttatg gatttgttta tgagattttt tactcttgga tcaattactg cacagccagt    25320
aaaaattgac aatgcttctc ctgcaagtac tgttcatgct acagcaacga taccgctaca    25380
agcctcactc cctttcggat ggcttgttat tggcgttgca tttcttgctg ttttttcagag    25440
cgctaccaaa ataattgcgc tcaataaaag atggcagcta gcccttata agggcttcca     25500
gttcatttgc aatttactgc tgctatttgt taccatctat tcacatcttt gcttgtcgc     25560
tgcaggtatg gaggcgcaat ttttgtacct ctatgccttg atatatttc tacaatgcat     25620
caacgcatgt agaattatta tgagatgttg ctttgttgg aagtgcaaat ccaagaaccc     25680
attactttat gatgccaact actttgtttg ctggcacaca cataactatg actactgtat    25740
accatataac agtgtcacag atacaattgt cgttactgaa ggtgacggca tttcaacacc    25800
aaaactcaaa gaagactacc aaattggtgg ttattctgag gataggcact caggtgttaa    25860
agactatgtc gttgtacatg gctatttcac cgaagtttac taccagcttg agtctacaca    25920
aattactaca gacactggta ttgaaaatgc tacattcttc atctttaaca agcttgttaa    25980
agacccaccg aatgtgcaaa tacacacaat cgacggctct tcaggagttg ctaatccagc    26040
aatggatcca atttatgatg agccgacgac gactactagc gtgcctttgt aagcacaaga    26100
aagtgagtac gaacttatgt actcattcgt ttcggaagaa acaggtacgt taatagttaa    26160
tagcgtactt cttttctttg ctttcgtggt attcttgcta gtcacactag ccatccttac    26220
tgcgcttcga ttgtgtgcgt actgctgcaa tattgttaac gtgagtttag taaaaccaac    26280
ggtttacgtc tactcgcgtg ttaaaaatct gaactcttct gaaggagttc ctgatcttct    26340
ggtctaaacg aactaactat tattattatt ctgtttggaa ctttaacatt gcttatcatg    26400
gcagacaacg gtactattac cgttgaggag cttaaacaac tcctggaaca atggaaccta    26460
gtaataggtt tcctattcct agcctggatt atgttactac aatttgccta ttctaatcgg    26520
aacaggtttt tgtacataat aaagcttgtt ttcctctggc tcttgtggcc agtaacactt    26580
gcttgttttg tgcttgctgc tgtctacaga attaattggg tgactggcgg gattgcgatt    26640
gcaatggctt gtattgtagg cttgatgtgg cttagctact tcgttgcttc cttcaggctg    26700
tttgctcgta cccgctcaat gtggtcattc aacccagaaa caaacattct tctcaatgtg    26760
cctctccggg ggacaattgt gaccagaccg ctcatggaaa gtgaacttgt cattggtgct    26820
gtgatcattc gtggtcactt gcgaatggcc ggacaccccc tagggcgctg tgacattaag    26880
gacctgccaa aagagatcac tgtggctaca tcacgaacgc tttcttatta caaattagga    26940
gcgtcgcagc gtgtaggcac tgattcaggt tttgctgcat acaaccgcta ccgtattgga    27000
aactataaat taaatacaga ccacgccggt agcaacgaca atattgcttt gctagtacag    27060
taagtgacaa cagatgtttc atcttgttga cttccaggtt acaatagcag agatattgat    27120
tatcattatg aggactttca ggattgctat ttggaatctt gacgttataa taagttcaat    27180
```

```
agtgagacaa ttatttaagc ctctaactaa gaagaattat tcggagttag atgatgaaga   27240
acctatggag ttagattatc cataaaacga acatgaaaat tattctcttc ctgacattga   27300
ttgtatttac atcttgcgag ctatatcact atcaggagtg tgttagaggt acgactgtac   27360
tactaaaaga accttgccca tcaggaacat acgagggcaa ttcaccattt caccctcttg   27420
ctgacaataa atttgcacta acttgcacta gcacacactt tgcttttgct tgtgctgacg   27480
gtactcgaca tacctatcag ctgcgtgcaa gatcagtttc accaaaactt ttcatcagac   27540
aagaggaggt tcaacaagag ctctactcgc cacttttttct cattgttgct gctctagtat   27600
ttttaatact ttgcttcacc attaagagaa agacagaatg aatgagctca ctttaattga   27660
cttctatttg tgcttttttag cctttctgct attccttgtt ttaataatgc ttattatatt   27720
ttggttttca ctcgaaatcc aggatctaga agaaccttgt accaaagtct aaacgaacat   27780
gaaacttctc attgttttga cttgtatttc tctatgcagt tgcatatgca ctgtagtaca   27840
gcgctgtgca tctaataaac ctcatgtgct tgaagatcct tgtaaggtac aacactaggg   27900
gtaatactta tagcactgct tggctttgtg ctctaggaaa ggttttaccct tttcatagat   27960 ggcacactat ggttcaaaca tgcacaccta atgttactat caactgtcaa gatccagctg   28020
gtggtgcgct tatagctagg tgttggtacc ttcatgaagg tcaccaaaact gctgcattta   28080 gagacgtact tgttgtttta aataaacgaa caaattaaaa tgtctgataa tggacccaa   28140 tcaaaccaac gtagtgcccc ccgcattaca tttggtggac ccacagattc aactgacaat   28200
aaccagaatg gaggacgcaa tggggcaagg ccaaaacagc gccgacccca aggtttaccc   28260
aataatactg cgtcttggtt cacagctctc actcagcatg gcaaggagga acttagattc   28320
cctcgaggcc agggcgttcc aatcaacacc aatagtggtc cagatgacca aattggctac   28380
taccgaagag ctacccgacg agttcgtggt ggtgacggca aaatgaaaga gctcagcccc   28440
agatggtact tctattacct aggaactggc ccagaagctt cacttcccta cggcgctaac   28500
aaagaaggca tcgtatgggt tgcaactgag ggagccttga atacacccaa agaccacatt   28560
ggcacccgca atcctaataa caatgctgcc accgtgctac aacttcctca aggaacaaca   28620
ttgccaaaag gcttctacgc agagggaagc agaggcggca gtcaagcctc ttctcgctcc   28680
tcatcacgta gtcgcggtaa ttcaagaaat tcaactcctg gcagcagtag gggaaattct   28740
cctgctcgaa tggctagcgg aggtggtgaa actgccctcg cgctattgct gctagacaga   28800
ttgaaccagc ttgagagcaa agtttctggt aaaggccaac aacaacaagg ccaaactgtc   28860
actaagaaat ctgctgctga ggcatctaaa aagcctcgcc aaaaacgtac tgccacaaaa   28920
cagtacaacg tcactcaagc atttgggaga cgtggtccag aacaaaccca aggaaatttc   28980
ggggaccaag acctaatcag acaaggaact gattacaaac attggccgca aattgcacaa   29040
tttgctccaa gtgcctctgc attctttgga atgtcacgca ttggcatgga agtcacacct   29100
tcgggaacat ggctgactta tcatggagcc attaaattgg atgacaaaga tccacaattc   29160
aaagacaacg tcatactgct gaacaagcac attgacgcat acaaaacatt cccaccaaca   29220
gagcctaaaa aggacaaaaa gaaaaagact gatgaagctc agcctttgcc gcagagacaa   29280
aagaagcagc ccactgtgac tcttcttcct gcggctgaca tggatgattt ctccagacaa   29340
cttcaaaatt ccatgagtgg agcttctgct gattcaactc aggcataaac actcatgatg   29400
accacacaag gcagatgggc tatgtaaacg ttttcgcaat tccgtttacg atacatagtc   29460
tactcttgtg cagaatgaat tctcgtaact aaacagcaca agtaggttta gttaactta    29520
```

```
atctcacata gcaatcttta atcaatgtgt aacattaggg aggacttgaa agagccacca    29580
cattttcatc gaggccacgc ggagtacgat cgagggtaca gtgaataatg ctagggagag    29640
ctgcctatat ggaagagccc taatgtgtaa aattaatttt agtagtgcta tccccatgtg    29700
attttaatag cttcttagga gaatgac                                        29727

<210> SEQ ID NO 14
<211> LENGTH: 240
<212> TYPE: DNA
<213> ORGANISM: Human coronavirus 229E

<400> SEQUENCE: 14
aatatgttaa agaacctgat ggccgatgtt gatgatccta aattgatggg atgggactat     60
cctaagtgtg atagagctat gccctcaatg attcgtatgt tgtcggctat gatcttaggt    120
tctaagcatg tcacatgttg tacggctagt gataaatttt atagacttag taatgagctt    180
gctcaagttt tgaccgaggt tgtttattca aatggtgggt tttatttaa acctggtggt     240

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
actatatgtt aaaccaggtg g                                               21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
atttacattg gctgtaacag c                                               21

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
agctaacgag tgtgcgcaag tattaagtga gatg                                 34

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cctctcttgt tcttgctcgc aaac                                            24

<210> SEQ ID NO 19
<211> LENGTH: 26
```

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 19
agaacaagag aggccattat cctaag                                          26

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 20
ttaacatata gtgagccgcc acac                                            24

<210> SEQ ID NO 21
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 21
agagccatgc ctaacat                                                    17

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 22
ggttgggatt atccaaaatg tgac                                            24

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 23
ggttgggatt atccaaaatg tga                                             23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 24
gtgtggcggc tcactatatg tta                                             23

<210> SEQ ID NO 25
<211> LENGTH: 240
<212> TYPE: DNA

<213> ORGANISM: Porcine epidemic diarrhea virus

<400> SEQUENCE: 25

```
aatatgctta agaaccttat tgatggtgtt gaaaatccgt gtcttatggg ttgggattac    60
ccaaagtgcg atagagcact gcccaatatg atacgcatga tttcagccat gatcttaggc   120
tctaagcaca ccacatgctg cagttctact gaccgctttt tcaggttgtg caatgaattg   180
gctcaagtcc ttactgaggt tgtttattct aatggagggt tttatttgaa gccaggtggt   240
```

<210> SEQ ID NO 26
<211> LENGTH: 240
<212> TYPE: DNA
<213> ORGANISM: Bovine coronavirus

<400> SEQUENCE: 26

```
gatatgttac gtcgccttat taaagatgtt gataatcctg tacttatggg ttgggattat    60
cctaagtgtg atcgtgctat gccaaacata ctacgtattg ttagtagtct ggttttggct   120
cgaaaacatg aggcatgttg ttcgcaaagc gataggtttt atcgacttgc gaatgaatgc   180
gcacaagttc tgagtgaaat tgttatgtgt ggtggctgtt attatgttaa gcctggtggc   240
```

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27

```
agctaacgag tgtgcgcaag tattaagtga gatg                                 34
```

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28

```
agagccatgc ctaacat                                                    17
```

<210> SEQ ID NO 29
<211> LENGTH: 240
<212> TYPE: DNA
<213> ORGANISM: SARS Coronavirus

<400> SEQUENCE: 29

```
aatatgttaa aaactgttta cagtgatgta gaaactccac accttatggg ttgggattat    60
ccaaaatgtg acagagccat gcctaacatg cttaggataa tggcctctct tgttcttgct   120
cgcaaaacata acacttgctg taacttatca caccgtttct acaggttagc taacgagtgt   180
gcgcaagtat taagtgagat ggtcatgtgt ggcggctcac tatatgttaa accaggtgga   240
```

<210> SEQ ID NO 30
<211> LENGTH: 240
<212> TYPE: DNA
<213> ORGANISM: SARS Coronavirus Sin 2500

<400> SEQUENCE: 30

```
aatatgttaa aaactgttta cagtgatgta gaaactccac accttatggg ttgggattat    60
```

-continued

```
ccaaaatgtg acagagccat gcctaacatg cttaggataa tggcctctct tgttcttgct    120
cgcaaacata acacttgctg taacttatca caccgtttct acaggttagc taacgagtgt    180
gcgcaagtat taagtgagat ggtcatgtgt ggcggctcac tatatgttaa accaggtgga    240

<210> SEQ ID NO 31
<211> LENGTH: 240
<212> TYPE: DNA
<213> ORGANISM: SARS Coronavirus GD01

<400> SEQUENCE: 31
aatatgttaa aaactgttta cagtgatgta gaaactccac accttatggg ttgggattat     60
ccaaaatgtg acagagccat gcctaacatg cttaggataa tggcctctct tgttcttgct    120
cgcaaacata acacttgctg taacttatca caccgtttct acaggttagc taacgagtgt    180
gcgcaagtat taagtgagat ggtcatgtgt ggcggctcac tatatgttaa accaggtgga    240

<210> SEQ ID NO 32
<211> LENGTH: 240
<212> TYPE: DNA
<213> ORGANISM: Murine hepatitis virus strain A59

<400> SEQUENCE: 32
gatatgttac gccgccttat taaagatgtt gatagtcctg tactcatggg ttgggactat     60
cctaaatgtg atcgtgctat gccaaacata ctgcgtattg ttagtagttt ggtgctagcc    120
cgtaaacatg attcgtgctg ttcgcatacg gatagattct atcgtcttgc gaacgagtgc    180
gcccaagttt tgagtgaaat tgttatgtgt ggtggttgtt attatgttaa accaggtggc    240

<210> SEQ ID NO 33
<211> LENGTH: 239
<212> TYPE: DNA
<213> ORGANISM: Infectious bronchitis virus

<400> SEQUENCE: 33
aacatgttga gaaacctgat tcagggtgtt gaagacccaa ttcttatggg ttgggattat     60
cctaagtgtg atagagcaat gcctaatttg ttgcgtatag cagcatcctt agtacttgct    120
cgcaaacaca ctaactgttg tagttggtct gaacgcattt ataggttgta taatgaatgc    180
gcccaggtct tatctgaaac tgtacttgct acaggtggta tttatgttaa acctggtgg     239
```

OLIGONUCLEOTIDES, REAGENTS AND AMPLIFICATION METHODS FOR DETECTING SEVERE ACUTE RESPIRATORY SYNDROME CORONAVIRUS

CROSS-REFERENCES TO RELATED APPLICATIONS

This application claims the benefit of U.S. Provisional Application Nos. 60/464,115, filed Apr. 21, 2003; 60/464,345, filed Apr. 22, 2003; 60/464,643, filed Apr. 23, 2003; 60/464,965, filed Apr. 24, 2003; and 60/496,016, filed Aug. 19, 2003, the disclosures of which are each incorporated by reference in their entirety for all purposes.

FIELD OF THE INVENTION

The present invention relates to the fields of molecular biology and nucleic acid chemistry. The invention provides methods and reagents for detecting the severe acute respiratory syndrome coronavirus (SARS CoV) and accordingly, also relates to the fields of medical diagnostics and prognostics.

BACKGROUND OF THE INVENTION

Severe acute respiratory syndrome (SARS) was first identified in late November 2002 in Guangdong Province, China. In the ensuing months, major outbreaks were reported in other parts of China, Vietnam, Canada, Singapore, Taiwan, and elsewhere in the world. The disease is unusual in its high level of infectivity, as demonstrated among the health care workers and family members that have been in close contact with infected individuals. In addition, it has also been reported that infected patients do not respond to empirical antimicrobial treatment for acute community-acquired typical or atypical pneumonia (Peiris et al. (2003) "Coronavirus as a possible cause of severe acute respiratory syndrome," *Lancet* 361:1319-1325, which is incorporated by reference).

The cause of SARS has been identified as a novel coronavirus (CoV) (Drosten et al. (2003) "Identification of a novel coronavirus in patients with severe acute respiratory syndrome," *N. Engl. J. Med.* 348:1967-1976, which is incorporated by reference), because clinical specimens from patients infected with SARS revealed the presence of crownshaped CoV particles. This new CoV has thus been referred to as SARS CoV. The full-length genome sequence of the SARS CoV has been reported from different isolates, and the genome organization of SARS CoV was found to be similar to that of other CoVs (Marra et al. (2003) "The genome sequence of the SARS-associated coronavirus," *Science* 300:1399-1404 and Ruan et al. (2003) "Comparative full-length genome sequence analysis of 14 SARS coronavirus isolates and common mutations associated with putative origins of infection," *Lancet* 361:1779-1785, which are both incorporated by reference).

CoVs are a family of positive-strand RNA-enveloped viruses called Coronaviridae, which are now categorized under the newly established order Nidovirales. This order comprises the families Coronaviridae and Arteriviridae. The name Nidovirales comes from the Latin word nidus, for nest, referring to the 3'-coterminal "nested" set of subgenomic mRNAs produced during viral infection (Cavanagh (2003) "Nidovirales: a new order comprising Coronaviridae and Arteriviridae," *Arch. Virol.* 14:629-633, which is incorporated by reference). The SARS CoV genome is very large, 29.7 kb (Marra et al. (2003), supra, and Ruan et al. (2003), supra, which are both incorporated by reference), and encodes 23 putative proteins. Major structural proteins include nucleocapsid, spike, membrane, and small envelope. Nonstructural proteins include the papainlike proteinase, 3C-like proteinase, RNA-dependent RNA polymerase (RdRp), helicase, and many other proteins involved with viral replication and transcription (Cavanagh (2003), supra, and Ng et al. (2002) "Membrane association and dimerization of a cysteine-rich, 16-kilodalton polypeptide released from the C-terminal region of the coronavirus infectious bronchitis virus 1a polyprotein," *J. Virol.* 76:6257-6267, which are both incorporated by reference). In other CoVs, many of the nonstructural proteins are only slightly conserved in the viral sequence, the exception being RdRp, which is highly conserved in many CoVs.

The use of oligonucleotide sequences as primers and/or probes for the recognition of infectious agents is one alternative to problematic immunological identification assays and other pre-existing methodologies. For example, nucleic acid probes complementary to targeted nucleic acid sequences have been used in hybridization procedures, such as Southern blots and dot blots, to detect the target nucleic acid sequence. Many of these hybridization procedures have depended on the cultivation and/or enrichment of the organism and, thus, are generally unsuitable for rapid diagnosis. The advent of techniques for the rapid amplification of specific nucleic acid sequences, such as the polymerase chain reaction among many others, has provided a mechanism to use primer and probe nucleic acids directly on clinical specimens, thereby eliminating enrichment and in vitro culturing of the pathogen prior to performing the hybridization assay. Thus, amplification-based hybridization assays can provide simple and rapid diagnostic techniques for the detection of pathogens, such as the SARS CoV in clinical samples.

SUMMARY OF THE INVENTION

The present invention provides methods and reagents for the rapid, reliable, and highly sensitive detection of the severe acute respiratory syndrome coronavirus without substantial detection of, or cross-reactivity with, other species in the coronavirus genus or species from other genera. Further, the methods and reagents of the invention can be utilized to detect the virus independent of the particular SARS CoV viral type. In addition to oligonucleotides, compositions, and reaction mixtures, the invention also relates to kits and systems for detecting these pathogenic agents, and to related computer and computer readable media.

In one aspect, the invention provides an oligonucleotide consisting of a nucleic acid with a sequence selected from the group consisting of: SEQ ID NOS: 1-12 and 15-24 or complements thereof. In another aspect, the invention provides an oligonucleotide comprising a nucleic acid with a sequence selected from the group consisting of: SEQ ID NOS: 1-12 and 15-24 and complements thereof, which oligonucleotide has 100 or fewer nucleotides. In still another aspect, the invention provides an oligonucleotide that includes a nucleic acid having at least 90% sequence identity (e.g., at least 95%, etc.) to one of SEQ ID NOS: 1-12 and 15-24 or a complement thereof, which oligonucleotide has 100 or fewer nucleotides. Typically, these oligonucleotides are primer nucleic acids, probe nucleic acids, or the like in these embodiments. In certain embodiments, the oligonucleotides described herein have sequences between about 12 and about 50 nucleotides in length. For example, these oligonucleotides have 40 or fewer nucleotides (e.g., 35 or fewer nucleotides, 30 or fewer nucleotides, etc.) in some embodiments. To further illustrate, the oligonucleotides comprise at least one modified nucleotide in some embodiments. In certain embodiments, for example, at least one nucleotide of an oligonucleotide described herein is modified to alter nucleic acid hybridization stability relative to unmodified nucleotides. In some embodiments, the oligonucleotides described herein comprise at least one label and/or at least one quencher moiety. In certain embodiments, the oligonucleotides include at least one conservatively modified variation.

In another aspect, the invention relates to a method of detecting a severe acute respiratory syndrome coronavirus in a sample. The method includes (a) contacting nucleic acids from the sample with at least one primer nucleic acid comprising at least one nucleic acid selected from the group consisting of: SEQ ID NOS: 1-12 and 15-24 and complements thereof in at least one nucleic acid amplification reaction (e.g., a nested polymerase chain reaction or the like). In addition, the method also includes (b) detecting the nucleic acids and/or one or more amplicons thereof from the nucleic acid amplification reaction during or after (a), thereby detecting the severe acute respiratory syndrome coronavirus in the sample. The sample is typically derived from a mammalian subject, such as a human subject. In certain embodiments, at least one of the amplicons is about 440 nucleotides in length. In some embodiments, at least one round of the nucleic acid amplification reaction is performed using primer nucleic acids comprising sequences selected from SEQ ID NOS: 11 or 22 and SEQ ID NOS: 12 or 20. In certain embodiments, at least one round of the nucleic acid amplification reaction is performed using primer nucleic acids comprising sequences selected from SEQ ID NOS: 15 or 18 and SEQ ID NOS: 16 or 19. Optionally, at least one of the primer nucleic acids comprises a modified primer nucleic acid and/or comprises at least one label. In some embodiments, for example, the modified primer nucleic acid comprises a nucleic acid amplification specificity altering modification and/or a restriction site linker modification. In certain embodiments, (b) comprises monitoring binding between the amplicons and at least one oligonucleotide having a sequence selected from the group consisting of: SEQ ID NOS: 1-12 and 15-24, a substantially identical variant thereof wherein the variant has at least 90% sequence identity to one of SEQ ID NOS: 1-12 and 15-24, and complements of SEQ ID NOS: 1-12 and 15-24 and the variant. Typically, the oligonucleotide comprises at least one label and/or at least one quencher moiety. In certain embodiments, for example, the oligonucleotide comprises a 5'-nuclease probe having a sequence selected from SEQ ID NO: 27 or SEQ ID NO: 28. In these embodiments, (b) optionally comprises detecting a detectable signal produced by the label, or amplifying a detectable signal produced by the label to produce an amplified signal and detecting the amplified signal.

In still another aspect, the invention provides a method of determining a presence of a severe acute respiratory syndrome coronavirus in a sample, which method comprises (a) contacting nucleic acids and/or amplicons thereof from the sample with one or more oligonucleotides that comprise at least one nucleic acid with a sequence selected from the group consisting of: SEQ ID NOS: 1-12 and 15-24, a substantially identical variant thereof wherein the variant has at least 90% sequence identity to one of SEQ ID NOS: 1-12 and 15-24, and complements of SEQ ID NOS: 1-12 and 15-24 and the variant. The method also includes (b) monitoring (e.g., at a single time point, at multiple discrete time points, continuously over a selected time period, etc.) binding between the nucleic acids and/or amplicons thereof, and the oligonucleotides; in which detectable binding between the nucleic acids and/or amplicons thereof, and the oligonucleotides, determines the presence of the severe acute respiratory syndrome coronavirus in the sample. The presence of the severe acute respiratory syndrome coronavirus in the sample is generally unknown or unsubstantiated before (a). In certain embodiments, (a) comprises contacting the nucleic acids and/or amplicons thereof with the oligonucleotides in solution at a temperature of at least 42° C. for at least 15 minutes in which a total weight of the solution comprises about 50% formalin and comprises heparin at a concentration of about 1 mg/ml. Moreover, the method typically comprises a reaction other than a sequencing reaction. The sample is generally derived from a mammalian subject, such as a human subject. In certain embodiments, the nucleic acids and/or amplicons thereof and the oligonucleotides are contacted in solution. Optionally, a solid support comprises the nucleic acids and/or amplicons (e.g., arrayed on the solid support). As an additional option, a solid support comprises the oligonucleotides.

In some embodiments, at least one segment of the nucleic acids is amplified prior to or during (a) using at least one nucleic acid amplification technique to produce the amplicons and (b) comprises monitoring the binding between the nucleic acids and/or amplicons thereof, and the oligonucleotides, during or after amplification. For example, the nucleic acid amplification technique typically comprises a polymerase chain reaction (e.g., a nest polymerase chain reaction, etc.), a ligase chain reaction, and/or the like. In these embodiments, the segment is optionally amplified using at least one primer nucleic acid comprising a sequence selected from the group consisting of: SEQ ID NOS: 1-12 and 15-24, a substantially identical variant thereof in which the variant has at least 90% sequence identity to one of SEQ ID NOS: 1-12 and 15-24, and complements of SEQ ID NOS: 1-12 and 15-24 and the variant. In some of these embodiments, the primer nucleic acid comprises at least one label, as described herein or otherwise known in the art. Optionally, the primer nucleic acid comprises a modified primer nucleic acid (e.g., a nucleic acid amplification specificity altering modification, a restriction site linker, and/or the like).

In another aspect, the invention relates to a composition comprising a sample derived from a subject and at least one oligonucleotide that comprises a nucleic acid with a sequence selected from the group consisting of: SEQ ID NOS: 1-12 and 15-24, a substantially identical variant thereof wherein the variant has at least 90% sequence identity to one of SEQ ID NOS: 1-12 and 15-24, and complements of SEQ ID NOS: 1-12 and 15-24 and the variant, which oligonucleotide consists of 100 or fewer nucleotides. A presence of a severe acute respiratory syndrome coronavirus in the sample is generally unknown or unsubstantiated. Typically, the oligonucleotides comprise at least one chemically synthesized nucleic acid. In certain embodiments, at least one nucleotide of a given oligonucleotide is modified (e.g., to alter nucleic acid hybridization stability relative to unmodified nucleotides).

Typically, at least one of the oligonucleotides comprises at least one label and/or at least one quencher moiety. To illustrate, the label optionally comprises a fluorescent dye, a weakly fluorescent label, a non-fluorescent label, a colorimetric label, a chemiluminescent label, a bioluminescent label, an antibody, an antigen, biotin, a hapten, a mass-modifying group, a radioisotope, an enzyme, or the like.

The oligonucleotides of the compositions of the invention are provided in various formats. In some embodiments, for example, at least one of the oligonucleotides is in solution. In other embodiments, a solid support comprises at least one of the oligonucleotides. In these embodiments, the oligonucleotides are non-covalently or covalently attached to the solid support. Exemplary solid supports utilized in these embodiments are optionally selected from, e.g., a plate, a microwell plate, a bead, a microbead (e.g., a magnetic microbead, etc), a tube (e.g., a microtube, etc.), a fiber, a whisker, a comb, a hybridization chip, a membrane, a single crystal, a ceramic layer, a self-assembling monolayer, and the like.

To further illustrate, the oligonucleotides are optionally conjugated with biotin or a biotin derivative and the solid support is optionally conjugated with avidin or an avidin derivative, or streptavidin or a streptavidin derivative. In some embodiments, a linker attaches the oligonucleotides to the solid support. The linker is typically selected from, e.g., an oligopeptide, an oligonucleotide, an oligopolyamide, an oligoethyleneglycerol, an oligoacrylamide, an alkyl chain, and the like. Optionally, a cleavable attachment attaches the oligonucleotides to the solid support. The cleavable attachment is generally cleavable by, e.g., heat, an enzyme, a chemical agent, electromagnetic radiation, etc.

In another aspect, the invention provides a kit that includes (a) at least one oligonucleotide that comprises a nucleic acid with a sequence selected from the group consisting of: SEQ ID NOS: 1-12 and 15-24, a substantially identical variant thereof wherein the variant has at least 90% sequence identity to one of SEQ ID NOS: 1-12 and 15-24, and complements of SEQ ID NOS: 1-12 and 15-24 and the variant, which oligonucleotide consists of 100 or fewer nucleotides; and one or more of: (b) instructions for determining a presence of a severe acute respiratory syndrome coronavirus in a sample by monitoring binding between nucleic acids and/or amplicons thereof from the sample and the oligonucleotide in which the presence of a severe acute respiratory syndrome coronavirus in the sample is unknown or unsubstantiated, or (c) at least one container for packaging at least the oligonucleotide. In some embodiments, the kit further includes at least one enzyme (e.g., a polymerase, etc.) and/or one or more nucleotides (e.g., deoxyribonucleotides, etc.).

In some embodiments, the oligonucleotide is in solution, whereas in others, a solid support comprises the oligonucleotide. The solid support is optionally selected from, e.g., a plate, a microwell plate, a bead, a microbead, a tube, a fiber, a whisker, a comb, a hybridization chip, a membrane, a single crystal, a ceramic layer, a self-assembling monolayer, or the like.

Typically, the oligonucleotide comprises at least one label and/or at least one quencher moiety. Exemplary labels include, e.g., a fluorescent dye, a weakly fluorescent label, a non-fluorescent label, a colorimetric label, a chemiluminescent label, a bioluminescent label, an antibody, an antigen, biotin, a hapten, a mass-modifying group, a radioisotope, an enzyme, or the like.

In still other aspects, the invention provides a system (e.g., an automated system) for detecting a severe acute respiratory syndrome coronavirus in a sample. The system includes (a) at least one oligonucleotide that comprises a nucleic acid with a sequence selected from the group consisting of: SEQ ID NOS: 1-12 and 15-24, a substantially identical variant thereof wherein the variant has at least 90% sequence identity to one of SEQ ID NOS: 1-12 and 15-24, and complements of SEQ ID NOS: 1-12 and 15-24 and the variant, which oligonucleotide consists of 100 or fewer nucleotides. The system also includes (b) at least one detector that detects binding between nucleic acids and/or amplicons thereof from the sample and the oligonucleotide, and (c) at least one controller operably connected to the detector, which controller comprises one or more instructions sets that correlate the binding detected by the detector with a presence of the severe acute respiratory syndrome coronavirus in the sample. In addition, the oligonucleotide typically comprises at least one label and/or at least one quencher moiety. In some embodiments, at least one container or solid support comprises the oligonucleotide. In these embodiments, the system optionally further includes (d) at least one thermal modulator operably connected to the container or solid support to modulate temperature in the container or on the solid support, and/or (e) at least one fluid transfer component that transfers fluid to and/or from the container or solid support, e.g., for performing one or more nucleic acid amplification techniques in the container or on the solid support, etc.

In yet another aspect, the invention provides a system that includes (a) computer or computer readable medium comprising a data set that comprises a plurality of character strings that correspond to a plurality of sequences that correspond to one or more of: SEQ ID NOS: 1-12 and 15-24, a substantially identical variant thereof wherein the variant has at least 90% sequence identity to one of SEQ ID NOS: 1-12 and 15-24, and complements of SEQ ID NOS: 1-12 and 15-24 and the variant. The system also includes (b) an automatic synthesizer coupled to an output of the computer or computer readable medium, which automatic synthesizer accepts instructions from the computer or computer readable medium, which instructions direct synthesis of one or more nucleic acids that correspond to one or more character strings in the data set.

Appendix

This application is being filed with a paper appendix totaling 22 pages. This appendix provides additional description of certain aspects of the invention and is incorporated by reference.

BRIEF DESCRIPTION OF THE DRAWINGS

FIG. 1 shows a nucleotide sequence of the SARS-CoV genome as determined by the Centers for Disease Control (Atlanta, Ga., USA) (SEQ ID NO: 13).

FIG. 2 shows alignments of nucleotide sequences from various SARS-CoV isolates and from certain non-target organisms relative to one another. Group 1 discloses SEQ ID NOS 29, 30, 31, 14 and 25, respectively, in order of appearance. Group 2 discloses SEQ ID NOS 30, 31, 29, 26, and 32, respectively, in order of appearance. Group 3 discloses SEQ ID NOS 30, 31, 29, and 33, respectively, in order of appearance.

DETAILED DESCRIPTION

I. Definitions

Figure 3:
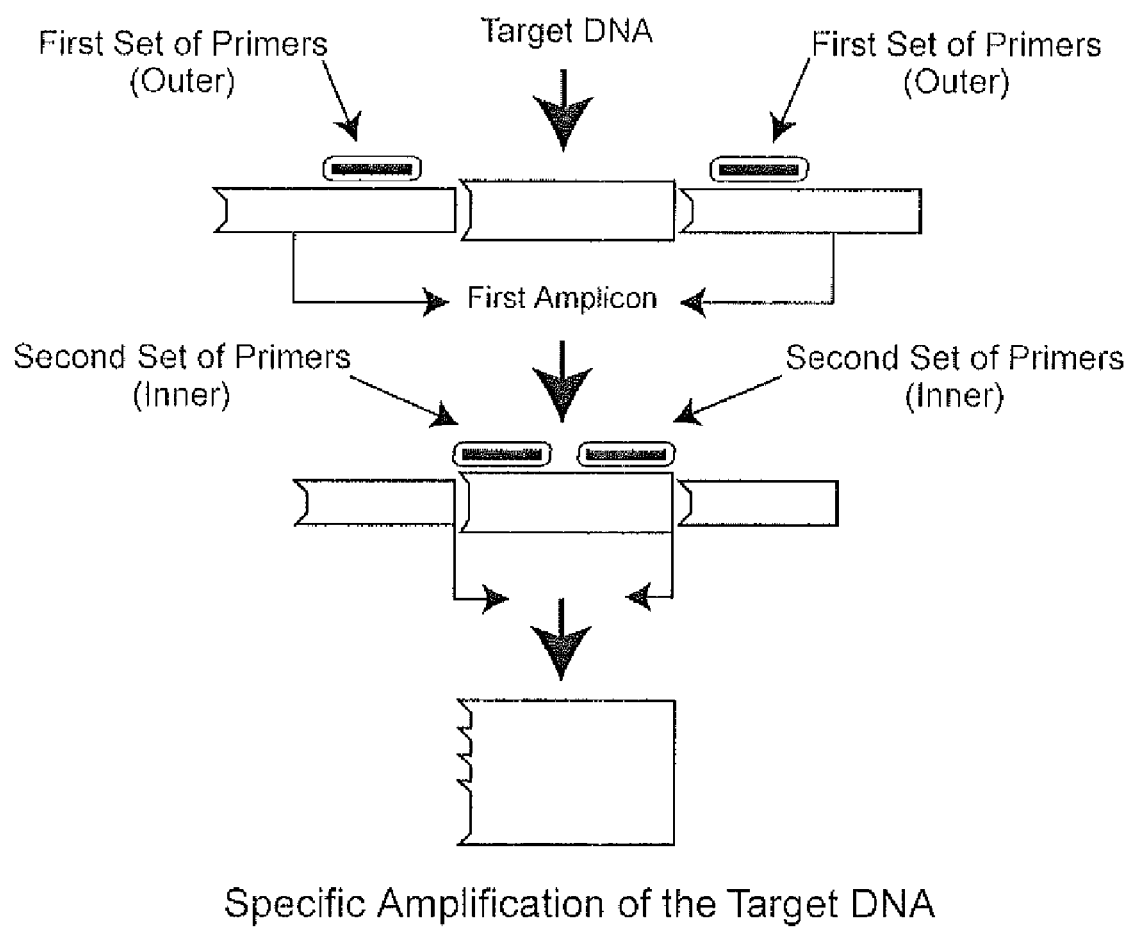
FIG. 3 schematically depicts a nested PCR procedure for detecting the SARS-CoV in a sample.

Before describing the present invention in detail, it is to be understood that this invention is not limited to particular oligonucleotides (e.g., primer nucleic acids, probe nucleic acids, etc.), methods, compositions, reaction mixtures, kits, systems, computers, or computer readable media, which can, of course, vary. It is also to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and/or claiming the present invention, the following terminology and grammatical variants will be used in accordance with the definitions set forth below.

A "5'-nuclease probe" refers to an oligonucleotide that comprises at least two labels and emits radiation of increased intensity after one of the two labels is cleaved or otherwise separated from the probe. In certain embodiments, for example, a 5'-nuclease probe is labeled with two different fluorescent dyes, e.g., a 5' terminus reporter dye and the 3' terminus quenching dye or moiety. When the probe is intact, energy transfer typically occurs between the two fluorophores such that fluorescent emission from the reporter dye is quenched. During an extension step of a polymerase chain reaction, for example, a 5'-nuclease probe bound to a template nucleic acid is cleaved by the 5' nuclease activity of, e.g., a Taq polymerase such that the fluorescent emission of the reporter dye is no longer quenched. Exemplary 5'-nuclease probes are described in, e.g., U.S. Pat. No. 5,210,015, entitled "HOMOGENEOUS ASSAY SYSTEM USING THE NUCLEASE ACTIVITY OF A NUCLEIC ACID POLYMERASE," issued May 11, 1993 to Gelfand et al., U.S. Pat. No. 5,994,056, entitled "HOMOGENEOUS METHODS FOR NUCLEIC ACID AMPLIFICATION AND DETECTION," issued Nov. 30, 1999 to Higuchi, and U.S. Pat. No. 6,171,785, entitled "METHODS AND DEVICES FOR HEMOGENEOUS NUCLEIC ACID AMPLIFICATION AND DETECTOR," issued Jan. 9, 2001 to Higuchi, which are each incorporated by reference.

The term "alteration" refers to a change in a nucleic acid sequence, including, but not limited to, a substitution, an insertion, and/or a deletion.

An "amplification reaction" refers to a primer initiated replication of one or more target nucleic acid sequences or complements thereto.

An "amplicon" refers to a molecule made by copying or transcribing another molecule, e.g., as occurs in transcription, cloning, and/or in a polymerase chain reaction ("PCR") (e.g., nested PCR, strand displacement PCR amplification (SDA), duplex PCR amplification, etc.) or another nucleic acid amplification technique. Typically, an amplicon is a copy of a selected nucleic acid (e.g., a template or target nucleic acid) or is complementary thereto.

An "amplified signal" refers to increased detectable signal that can be produced in the absence of, or in conjunction with, an amplification reaction. Exemplary signal amplification techniques are described in, e.g., Cao et al. (1995) "Clinical evaluation of branched DNA signal amplification for quantifying HIV type 1 in human plasma," *AIDS Res Hum Retroviruses* 11(3):353-361, and in U.S. Pat. No. 5,437,977 to Segev, U.S. Pat. No. 6,033,853 to Delair et al., and U.S. Pat. No. 6,180,777 to Horn, which are each incorporated by reference.

"Antibody" refers to a polypeptide substantially encoded by at least one immunoglobulin gene or fragments of at least one immunoglobulin gene, that can participate in detectable binding with a ligand. The term includes naturally-occurring forms, as well as fragments and derivatives. Fragments within the scope of the term as used herein include those produced by digestion with various peptidases, such as Fab, Fab' and F(ab)'2 fragments, those produced by chemical dissociation, by chemical cleavage, so long as the fragment remains capable of detectable binding to a target molecule, such as an antigen indicative of a disease.

An "array" refers to an assemblage of elements. The assemblage can be spatially ordered (a "patterned array") or disordered (a "randomly patterned" array). The array can form or comprise one or more functional elements (e.g., a probe region on a microarray) or it can be non-functional.

The term "attached" or "conjugated" refers to interactions and/or states in which material or compounds are connected or otherwise joined with one another. These interactions and/or states are typically produced by, e.g., covalent bonding, ionic bonding, chemisorption, physisorption, and combinations thereof. In certain embodiments, for example, oligonucleotides are attached to solid supports. In some of these embodiments, an oligonucleotide is conjugated with biotin (i.e., is biotinylated) and a solid support is conjugated with avidin such that the oligonucleotide attaches to the solid support via the binding interaction of, e.g., biotin and avidin.

Molecular species "bind" when they associate with one another via covalent and/or non-covalent interactions. For example, two complementary single-stranded nucleic acids can hybridize with one another to form a nucleic acid with at least one double-stranded region. To further illustrate, antibodies and corresponding antigens can also non-covalently associate with one another.

The term "cleavage" refers to a process of releasing a material or compound from attachment to another material or compound. In certain embodiments, for example, oligonucleotides are cleaved from, e.g., a solid support to permit analysis of the oligonucleotides by solution-phase methods. See, e.g., Wells et al. (1998) "Cleavage and Analysis of Material from Single Resin Beads," *J. Org. Chem.* 63:6430, which is incorporated by reference.

A "character" when used in reference to a character of a character string refers to a subunit of the string. In one embodiment, the character of a character string encodes one subunit of an encoded biological molecule. Thus, for example, where the encoded biological molecule is a polynucleotide or oligonucleotide, a character of the string encodes a single nucleotide.

A "character string" is any entity capable of storing sequence information (e.g., the subunit structure of a biological molecule such as the nucleotide sequence of a nucleic acid, etc.). In one embodiment, the character string can be a simple sequence of characters (letters, numbers, or other symbols) or it can be a numeric or coded representation of such information in tangible or intangible (e.g., electronic, magnetic, etc.) form. The character string need not be "linear," but can also exist in a number of other forms, e.g., a linked list or other non-linear array (e.g., used as a code to generate a linear array of characters), or the like. Character strings are typically those which encode oligonucleotide or polynucleotide strings, directly or indirectly, including any encrypted strings, or images, or arrangements of objects which can be transformed unambiguously to character strings representing sequences of monomers or multimers in polynucleotides, or the like (whether made of natural or artificial monomers).

The term "complement thereof" refers to nucleic acid that is both the same length as, and exactly complementary to, a given nucleic acid.

A "composition" refers to a combination of two or more different components. In certain embodiments, for example, a composition includes a solid support that comprises one or more oligonucleotides, e.g., covalently or non-covalently attached to a surface of the support. In other embodiments, a composition includes one or more oligonucleotides in solution.

The term "deletion" in the context of a nucleic acid sequence refers to an alteration in which at least one nucleotide is removed from the nucleic acid sequence, e.g., from a 5'-terminus, from a 3'-terminus, and/or from an internal position of the nucleic acid sequence.

The term "derivative" refers to a chemical substance related structurally to another substance, or a chemical substance that can be made from another substance (i.e., the substance it is derived from), e.g., through chemical or enzymatic modification. To illustrate, oligonucleotides are optionally conjugated with biotin or a biotin derivative. To further illustrate, one nucleic acid can be "derived" from another through processes, such as chemical synthesis based on knowledge of the sequence of the other nucleic acid, amplification of the other nucleic acid, or the like.

The term "detectably bind" refers to binding between at least two molecular species (e.g., a probe nucleic acid and a target nucleic acid, a sequence specific antibody and a target nucleic acid, etc.) that is detectable above a background signal (e.g., noise) using one or more methods of detection.

Nucleic acids are "extended" or "elongated" when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

An "extended primer nucleic acid" refers to a primer nucleic acid to which one or more additional nucleotides have been added or otherwise incorporated (e.g., covalently bonded thereto).

Nucleic acids "hybridize" or "bind" when they associate with one another, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, New York), as well as in Ausubel (Ed.) *Current Protocols in Molecular Biology*, Volumes I, II, and III, 1997, which is incorporated by reference. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides. Both Hames and Higgins 1 and 2 are incorporated by reference.

"Stringent hybridization wash conditions" in the context of nucleic acid hybridization assays or experiments, such as nucleic acid amplification reactions, Southern and northern hybridizations, or the like, are sequence dependent, and are different under different environmental parameters. An extensive guide to the hybridization of nucleic acids is found in Tijssen (1993), supra. and in Hames and Higgins, 1 and 2.

For purposes of the present invention "highly stringent" hybridization and wash conditions are selected to be at least about 5° C. lower than the thermal melting point ($T_m$) for the specific sequence at a defined ionic strength and pH. The $T_m$ is the temperature (under defined ionic strength and pH) at which 50% of the test sequence hybridizes to a perfectly matched oligonucleotide. Very stringent conditions are selected to be equal to the $T_m$ for a particular oligonucleotide.

An example of stringent hybridization conditions for hybridization of complementary nucleic acids on a filter in a Southern or northern blot is 50% formalin with 1 mg of heparin at 42° C., with the hybridization being carried out overnight. An example of stringent wash conditions is a 0.2× SSC wash at 65° C. for 15 minutes (see, Sambrook et al., *Molecular Cloning: A Laboratory Manual*, 3rd Ed., Cold Spring Harbor Laboratory Press, Cold Spring Harbor, N.Y. (2001), which is incorporated by reference, for a description of SSC buffer). Often the high stringency wash is preceded by a low stringency wash to remove background probe signal. An example low stringency wash is 2× SSC at 40° C. for 15 minutes. In general, a signal to noise ratio of 5× (or higher) than that observed for an unrelated probe in the particular hybridization assay indicates detection of a specific hybridization.

Comparative hybridization can be used to identify nucleic acids of the invention.

In particular, detection of stringent hybridization in the context of the present invention indicates strong structural similarity to, e.g., the nucleic acids provided in the sequence listing herein. For example, it is desirable to identify test nucleic acids that hybridize to the exemplar nucleic acids herein under stringent conditions. One measure of stringent hybridization is the ability to detectably hybridize to one of the listed nucleic acids (e.g., nucleic acids with sequences selected from SEQ ID NOS: 1-12 and 15-24 and complements thereof) under stringent conditions. Stringent hybridization and wash conditions can easily be determined empirically for any test nucleic acid.

For example, in determining highly stringent hybridization and wash conditions, the stringency of the hybridization and wash conditions are gradually increased (e.g., by increasing temperature, decreasing salt concentration, increasing detergent concentration and/or increasing the concentration of organic solvents such as formalin in the hybridization or wash), until a selected set of criteria is met. For example, the stringency of the hybridization and wash conditions are gradually increased until a oligonucleotide consisting of or comprising one or more nucleic acid sequences selected from SEQ ID NOS: 1-12 and 15-24 and complementary polynucleotide sequences thereof, binds to a perfectly matched complementary target (again, a nucleic acid comprising one or more nucleic acid sequences selected from SEQ ID NOS: 1-12 and 15-24 and complementary polynucleotide sequences thereof), with a signal to noise ratio that is at least 5× as high as that observed for hybridization of the oligonucleotide to non-target nucleic acids present in the sample (e.g., nucleic acids from organisms other than SARS-CoV).

The detection of target nucleic acids which hybridize to the nucleic acids represented by SEQ ID NOS: 1-12 and 15-24 under high stringency conditions are a feature of the invention. Examples of such nucleic acids include those with one or a few silent or conservative nucleic acid substitutions as compared to a given nucleic acid sequence.

The terms "identical" or percent "identity" in the context of two or more nucleic acid or polypeptide sequences, refer to two or more sequences or subsequences that are the same or have a specified percentage of amino acid residues or nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "Power-BLAST: A new network BLAST application for interactive or automated sequence analysis and annotation" *Genome Res.* 7:649-656, which are each incorporated by reference. Many other optimal alignment algorithms are also known in the art and are optionally utilized to determine percent sequence identity.

The phrase "in solution" refers to an assay or reaction condition in which the components of the assay or reaction are not attached to a solid support and are present in a liquid medium. Exemplary liquid mediums include aqueous and organic fluids. For example, certain assays of the invention include incubating oligonucleotides together with SARS-CoV nucleic acids and SARS-CoV nucleic acid amplicons in solution to allow hybridization to occur.

The term "insertion" in the context of a nucleic acid sequence refers to an alteration in which at least one nucleotide is added to the nucleic acid sequence, e.g., at a 5'-terminus, at a 3'-terminus, and/or at an internal position of the nucleic acid sequence.

A "label" refers to a moiety attached (covalently or non-covalently), or capable of being attached, to a molecule, which moiety provides or is capable of providing information about the molecule (e.g., descriptive, identifying, etc. information about the molecule) or another molecule with which the labeled molecule interacts (e.g., hybridizes, etc.). Exemplary labels include fluorescent labels (including, e.g., quenchers or absorbers), weakly fluorescent labels, non-fluorescent labels, colorimetric labels, chemiluminescent labels, bioluminescent labels, radioactive labels, mass-modifying groups, antibodies, antigens, biotin, haptens, enzymes (including, e.g., peroxidase, phosphatase, etc.), and the like.

A "linker" refers to a chemical moiety that covalently or non-covalently attaches a compound or substituent group to another moiety, e.g., a probe nucleic acid, a primer nucleic acid, an amplicon, a solid support, or the like. For example, linkers are optionally used to attach oligonucleotides to a solid support (e.g., in a linear or other logic probe array). To further illustrate, a linker optionally attaches a label (e.g., a fluorescent dye, a radioisotope, etc.) to a probe nucleic acid, a primer nucleic acid, or the like. Linkers are typically at least bifunctional chemical moieties and in certain embodiments, they comprise cleavable attachments, which can be cleaved by, e.g., heat, an enzyme, a chemical agent, electromagnetic radiation, etc. to release materials or compounds from, e.g., a solid support. A careful choice of linker allows cleavage to be performed under appropriate conditions compatible with the stability of the compound and assay method. Generally a linker has no specific biological activity other than to, e.g., join chemical species together or to preserve some minimum distance or other spatial relationship between such species. However, the constituents of a linker may be selected to influence some property of the linked chemical species such as three-dimensional conformation, net charge, hydrophobicity, etc. Exemplary linkers include, e.g., oligopeptides, oligonucleotides, oligopolyamides, oligoethyleneglycerols, oligoacrylamides, alkyl chains, or the like. Additional description of linker molecules is provided in, e.g., Hermanson, *Bioconjugate Techniques,* Elsevier Science (1996), Lyttle et al. (1996) *Nucleic Acids Res.* 24(14):2793, Shchepino et al. (2001) *Nucleosides, Nucleotides, & Nucleic Acids* 20:369, Doronina et al (2001) *Nucleosides, Nucleotides, & Nucleic Acids* 20:1007, Trawick et al. (2001) *Bioconjugate Chem.* 12:900, Olejnik et al. (1998) *Methods in Enzymology* 291:135, and Pljevaljcic et al. (2003) *J. Am. Chem. Soc.* 125(12):3486, all of which are incorporated by reference.

A "mass modifying" group modifies the mass, typically measured in terms of molecular weight as daltons, of a molecule that comprises the group. For example, mass modifying groups that increase the discrimination between at least two nucleic acids with single base differences in size or sequence can be used to facilitate sequencing using, e.g., molecular weight determinations.

A "mixture" refers to a combination of two or more different components. A "reaction mixture" refers a mixture that comprises molecules that can participate in and/or facilitate a given reaction. An "amplification reaction mixture" refers to a solution containing reagents necessary to carry out an amplification reaction, and typically contains primers, a thermostable DNA polymerase, dNTP's, and a divalent metal cation in a suitable buffer. A reaction mixture is referred to as complete if it contains all reagents necessary to carry out the reaction, and incomplete if it contains only a subset of the necessary reagents. It will be understood by one of skill in the art that reaction components are routinely stored as separate solutions, each containing a subset of the total components, for reasons of convenience, storage stability, or to allow for application-dependent adjustment of the component concentrations, and, that reaction components are combined prior to the reaction to create a complete reaction mixture. Furthermore, it will be understood by one of skill in the art that reaction components are packaged separately for commercialization and that useful commercial kits may contain any subset of the reaction components, which includes the modified primers of the invention.

A "modified primer nucleic acid" refers to a primer nucleic acid that comprises a moiety or sequence of nucleotides that provides a desired property to the primer nucleic acid. In certain embodiments, for example, modified primer nucleic acids comprise "nucleic acid amplification specificity altering modifications" that, e.g., reduce non-specific nucleic acid amplification (e.g., minimize primer dimer formation or the like), increase the yield of an intended target amplicon, and/or the like. Examples of nucleic acid amplification specificity altering modifications are described in, e.g., U.S. Pat. No. 6,001,611, entitled "MODIFIED NUCLEIC ACID AMPLIFICATION PRIMERS," issued Dec. 14, 1999 to Will, which is incorporated by reference. Other exemplary primer nucleic acid modifications include a "restriction site linker modification" in which a nucleotide sequence comprising a selected restriction site is attached, e.g., at 5'-terminus of a primer nucleic acid. Restriction site linkers are typically attached to primer nucleic acids to facilitate subsequent amplicon cloning or the like.

A "moiety" or "group" refers to one of the portions into which something, such as a molecule, is divided (e.g., a functional group, substituent group, or the like). For example, an oligonucleotide optionally comprises a quencher moiety, a labeling moiety, or the like.

The term "nucleic acid" refers to nucleotides (e.g., ribonucleotides, deoxyribonucleotides, dideoxynucleotides, etc.) and polymers that comprise such nucleotides covalently linked together, either in a linear or branched fashion. Exemplary nucleic acids include deoxyribonucleoic acids (DNAs); ribonucleic acids (RNAs), DNA-RNA hybrids, oligonucleotides, polynucleotides, genes, cDNAs, aptamers, antisense nucleic acids, interfering RNAs (RNAis), molecular beacons, nucleic acid probes, peptide nucleic acids (PNAs), locked nucleic acids (LNA™s), PNA-DNA conjugates, PNA-RNA conjugates, LNA™-DNA conjugates, LNA™-RNA conjugates, etc.

A nucleic acid is typically single-stranded or double-stranded and will generally contain phosphodiester bonds, although in some cases, as outlined herein, nucleic acid analogs are included that may have alternate backbones, including, for example and without limitation, phosphoramide (Beaucage et al. (1993) *Tetrahedron* 49(10):1925 and references therein; Letsinger (1970) *J. Org. Chem.* 35:3800; Sprinzl et al. (1977) *Eur. J. Biochem.* 81:579; Letsinger et al. (1986) *Nucl. Acids Res.* 14: 3487; Sawai et al. (1984) *Chem. Lett.* 805; Letsinger et al. (1988) *J. Am. Chem. Soc.* 110:4470; and Pauwels et al. (1986) *Chemica Scripta* 26: 1419, which are each incorporated by reference), phosphorothioate (Mag et al. (1991) *Nucleic Acids Res.* 19:1437; and U.S. Pat. No. 5,644,048, which are both incorporated by reference), phosphorodithioate (Briu et al. (1989) *J. Am. Chem. Soc.* 111: 2321, which is incorporated by reference), O-methylphophoroamidite linkages (see Eckstein, *Oligonucleotides and Analogues: A Practical Approach,* Oxford University Press (1992), which is incorporated by reference), and peptide nucleic acid backbones and linkages (see, Egholm (1992) *J. Am. Chem. Soc.* 114:1895; Meier et al. (1992) *Chem. Int. Ed. Engl.* 31:1008; Nielsen (1993) *Nature* 365:566; and Carlsson et al. (1996) *Nature* 380:207, which are each incorporated by reference). Other analog nucleic acids include those with positively charged backbones (Denpcy et al. (1995) *Proc. Natl. Acad. Sci. USA* 92:6097, which is incorporated by reference); non-ionic backbones (U.S. Pat. Nos. 5,386,023, 5,637,684, 5,602,240, 5,216,141 and 4,469,863; Angew (1991) *Chem. Intl. Ed. English* 30: 423; Letsinger et al. (1988) *J. Am. Chem. Soc.* 110:4470; Letsinger et al. (1994) *Nucleoside & Nucleotide* 13:1597; Chapters 2 and 3, ASC Symposium Series 580, "Carbohydrate Modifications in Antisense Research", Ed. Y. S. Sanghvi and P. Dan Cook; Mesmaeker et al. (1994) *Bioorganic & Medicinal Chem. Lett.* 4: 395; Jeffs et al. (1994) *J. Biomolecular NMR* 34:17; and *Tetrahedron Lett.* 37:743 (1996), which are each incorporated by reference) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which references are each incorporated by reference. Nucleic acids containing one or more carbocyclic sugars are also included within the definition of nucleic acids (see Jenkins et al. (1995) *Chem. Soc. Rev.* pp 169-176, which is incorporated by reference). Several nucleic acid analogs are also described in, e.g., Rawls, C & E News Jun. 2, 1997 page 35, which is incorporated by reference. These modifications of the ribose-phosphate backbone may be done to facilitate the addition of additional moieties such as labels, or to alter the stability and half-life of such molecules in physiological environments.

In addition to these naturally occurring heterocyclic bases that are typically found in nucleic acids (e.g., adenine, guanine, thymine, cytosine, and uracil), nucleic acid analogs also include those having non-naturally occurring heterocyclic or modified bases, many of which are described, or otherwise referred to, herein. In particular, many non-naturally occurring bases are described further in, e.g., Seela et al. (1991) *Helv. Chim. Acta* 74:1790, Grein et al. (1994) *Bioorg. Med. Chem. Lett.* 4:971-976, and Seela et al. (1999) *Helv. Chim. Acta* 82:1640, which are each incorporated by reference. To further illustrate, certain bases used in nucleotides that act as melting temperature ($T_m$) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

Examples of modified bases and nucleotides are also described in, e.g., U.S. Pat. No. 5,484,908, entitled "OLIGONUCLEOTIDES CONTAINING 5-PROPYNYL PYRIMIDINES," issued Jan. 16, 1996 to Froehler et al., U.S. Pat. No. 5,645,985, entitled "ENHANCED TRIPLE-HELIX AND DOUBLE-HELIX FORMATION WITH OLIGOMERS CONTAINING MODIFIED PYRIMIDINES," issued Jul. 8, 1997 to Froehler et al., U.S. Pat. No. 5,830,653, entitled "METHODS OF USING OLIGOMERS CONTAINING MODIFIED PYRIMIDINES," issued Nov. 3, 1998 to Froehler et al., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference.

The term "nucleic acid detection reagent" refers to a reagent that detectably binds (e.g., hydrogen bonds in nucleic acid hybridization, in antibody-antigen recognition, or the like, or other types of binding interactions) to a SARS-CoV nucleic acid. For example, nucleic acids (e.g., probe nucleic acids, primer nucleic acids, etc.) that comprise sequences selected from SEQ ID NOS: 1-12 and 15-24 or complements thereof bind to SARS-CoV nucleic acids. Other exemplary nucleic acid detection reagents include sequence specific antibodies that specifically bind to SARS-CoV nucleic acids.

A "nucleotide" refers to an ester of a nucleoside, e.g., a phosphate ester of a nucleoside. For example, a nucleotide can include 1, 2, 3, or more phosphate groups covalently linked to a 5' position of a sugar moiety of the nucleoside.

A "nucleotide incorporating biocatalyst" refers to a catalyst that catalyzes the incorporation of nucleotides into a nucleic acid. Nucleotide incorporating biocatalysts are typically enzymes. An "enzyme" is a protein- and/or nucleic acid-based catalyst that acts to reduce the activation energy of a chemical reaction involving other compounds or "substrates." A "nucleotide incorporating enzyme" refers to an enzyme that catalyzes the incorporation of nucleotides into a nucleic acid, e.g., during nucleic acid amplification or the like. Exemplary nucleotide incorporating enzymes include, e.g., polymerases, terminal transferases, reverse transcriptases, telomerases, polynucleotide phosphorylases, and the like.

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) *Meth. Enzymol.* 68:90-99; the phosphodiester method of Brown et al. (1979) *Meth. Enzymol.* 68:109-151; the diethylphosphoramidite method of Beaucage et al. (1981) *Tetrahedron Lett.* 22:1859-1862; the triester method of Matteucci et al. (1981) *J. Am. Chem. Soc.* 103:3185-3191; automated synthesis methods; or the solid support method of U.S. Pat. No. 4,458,066, or other methods known in the art. All of these references are incorporated by reference.

The term "probe nucleic acid" or "probe" refers to a labeled or unlabeled oligonucleotide capable of selectively hybridizing to a target nucleic acid under suitable conditions. Typically, a probe is sufficiently complementary to a specific target sequence contained in a SARS-CoV nucleic acid sample to form a stable hybridization duplex with the target sequence under a selected hybridization condition, such as, but not limited to, a stringent hybridization condition. A hybridization assay carried out using the probe under sufficiently stringent hybridization conditions permits the selective detection of a specific target sequence. The term "hybridizing region" refers to that region of a nucleic acid that is exactly or substantially complementary to, and therefore hybridizes to, the target sequence. For use in a hybridization assay for the discrimination of single nucleotide differences in sequence, the hybridizing region is typically from about 8 to about 100 nucleotides in length. Although the hybridizing region generally refers to the entire oligonucleotide, the probe may include additional nucleotide sequences that function, for example, as linker binding sites to provide a site. for attaching the probe sequence to a solid support or the like. In certain embodiments, a probe of the invention comprises one or more labels (e.g., a reporter dye, a quencher moiety, etc.), such as a 5'-nuclease probe, a FRET probe, a molecular beacon, or the like, which can also be utilized to detect hybridization between the probe and target nucleic acids in a sample. In some embodiments, the hybridizing region of the probe is completely complementary to the target sequence. However, in general, complete complementarity is not necessary; stable duplexes may contain mismatched bases or unmatched bases. Modification of the stringent conditions may be necessary to permit a stable hybridization duplex with one or more base pair mismatches or unmatched bases. Sambrook et al., *Molecular Cloning: A Laboratory Manual,* 3rd Ed., Cold Spring Harbor Laboratory Press, Cold Spring Harbor, N.Y. (2001), which is incorporated by reference, provides guidance for suitable modification. Stability of the target/probe duplex depends on a number of variables including length of the oligonucleotide, base composition and sequence of the oligonucleotide, temperature, and ionic conditions. One of skill in the art will recognize that, in general, the exact complement of a given probe is similarly useful as a probe. Exemplary probes of the invention that bind to SARS-CoV nucleic acids include oligonucleotides that comprise sequences selected from the group consisting of: SEQ ID NOS: 1-12 and 15-24, a substantially identical variant thereof wherein the variant has at least 90% sequence identity to one of SEQ ID NOS: 1-12 and 15-24, and complements of SEQ ID NOS: 1-12 and 15-24 and the variant. One of skill in the art will also recognize that, in certain embodiments, probe nucleic acids can also be used as primer nucleic acids.

A "primer nucleic acid" or "primer" is a nucleic acid that can hybridize to a template nucleic acid (e.g., a SARS-CoV nucleic acid) and permit chain extension or elongation using, e.g., a nucleotide incorporating biocatalyst, such as a polymerase under appropriate reaction conditions. A primer nucleic acid is typically a natural or synthetic oligonucleotide (e.g., a single-stranded oligodeoxyribonucleotide, etc.). Although other primer nucleic acid lengths are optionally utilized, they typically comprise hybridizing regions that range from about 8 to about 100 nucleotides in length. Short primer nucleic acids generally utilize cooler temperatures to form sufficiently stable hybrid complexes with template SARS-CoV nucleic acid. A primer nucleic acid that is at least partially complementary to a subsequence of a template SARS-CoV nucleic acid is typically sufficient to hybridize with the template for extension to occur. A primer nucleic acid can be labeled, if desired, by incorporating a label detectable by, e.g., spectroscopic, photochemical, biochemical, immunochemical, chemical, or other techniques. To illustrate, useful labels include radioisotopes, fluorescent dyes, electron-dense reagents, enzymes (as commonly used in ELISAs), biotin, or haptens and proteins for which antisera or monoclonal antibodies are available. Many of these and other labels are described further herein and/or are otherwise known in the art. Exemplary primer nucleic acids of the invention that bind to SARS-CoV nucleic acids include oligonucleotides that comprise sequences selected from the group consisting of: SEQ ID NOS: 1-12 and 15-24, a substantially identical variant thereof wherein the variant has at least 90% sequence identity to one of SEQ ID NOS: 1-12 and 15-24, and complements of SEQ ID NOS: 1-12 and 15-24 and the variant. One of skill in the art will recognize that, in certain embodiments, primer nucleic acids can also be used as probe nucleic acids.

A "quencher moiety" or "quencher" refers to a moiety that reduces and/or is capable of reducing the detectable emission of radiation, e.g., fluorescent or luminescent radiation, from a source that would otherwise have emitted this radiation. A quencher typically reduces the detectable radiation emitted by the source by at least 50%, typically by at least 80%, and more typically by at least 90%. Exemplary quenchers are provided in, e.g., U.S. Pat. No. 6,465,175, entitled "OLIGONUCLEOTIDE PROBES BEARING QUENCHABLE FLUORESCENT LABELS, AND METHODS OF USE THEREOF," which issued Oct. 15, 2002 to Horn et al., which is incorporated by reference.

The term "sample" refers to any substance containing or presumed to contain one or more SARS-CoV nucleic acids including, but not limited to, clinical samples (e.g., tissue or fluid isolated from one or more subjects or individuals), in vitro cell culture constituents, environmental samples, and the like. Exemplary samples include blood, plasma, serum, feces, bronchoalveolar lavage, nasal pharyngeal swabs and tissues, urine, synovial fluid, seminal fluid, seminal plasma, prostatic fluid, vaginal fluid, cervical fluid, uterine fluid, cervical scrapings, amniotic fluid, anal scrapings, mucus, sputum, tissue, and the like.

The phrase "sample derived from a subject" refers to a sample obtained from the subject, whether or not that sample undergoes one or more processing steps (e.g., cell lysis, debris removal, stabilization, etc.) prior to analysis. To illustrate, samples can be derived from subjects by scraping, venipuncture, swabbing, biopsy, or other techniques known in the art.

The term "severe acute respiratory syndrome coronavirus" or "SARS-CoV" refers to a positive-strand RNA-enveloped virus of the family Coronaviridae and the order Nidovirales, which causes the severe acute respiratory syndrome (SARS) in subjects infected with the virus. See, e.g., Kiazek et al. (2003) "A novel coronavirus associated with severe acute respiratory syndrome," *N. Engl. J. Med.* 348:1953-1966, Drosten et al. (2003) "Identification of a novel coronavirus in patients with severe acute respiratory syndrome," *N. Engl. J. Med.* 348:1967-1976, Marra et al. (2003) "The genome sequence of the SARS-associated coronavirus," *Science* 300: 1399-1404, Ruan et al. (2003) "Comparative full-length genome sequence analysis of 14 SARS coronavirus isolates and common mutations associated with putative origins of infection," *Lancet* 361:1779-1785, and Cavanagh (2003) "Nidovirales: a new order comprising Coronaviridae and Arteriviridae," *Arch. Virol.* 14:629-633, which are each incorporated by reference. Exemplary GenBank® accession numbers for complete sequences of the SARS-CoV genome are NC_004718, AY283794, AY278489, AY278741, AY559097, AY559096, AY559095, AY559094, AY559093, AY559092, AY559091, AY559090, AY559089, AY559088, AY559087, AY559086, AY559085, AY559084, AY559083, AY559082, AY559081, AY274119, AY323977, AY291315, and the like. To further illustrate, FIG. 1 provides the nucleotide sequence of the SARS-CoV genome (Urbani strain) as determined by the Centers for Disease Control.

The term "severe acute respiratory syndrome coronavirus nucleic acid" or "SARS-CoV nucleic acid" refers to a nucleic acid that is derived or isolated from a SARS-CoV and/or an amplicon thereof.

The term "selectively bind" or "selective binding" in the context of nucleic acid detection reagents refers to a nucleic acid detection reagent that binds to SARS-CoV nucleic acids to a greater extent than the nucleic acid detection reagent binds, under the same hybridization conditions, to non-target nucleic acids.

The term "selectively detect" refers to the ability to detect a SARS-CoV nucleic acid to a greater extent than nucleic acids from other organisms.

"Selectively hybridizing" or "selective hybridization" occurs when a nucleic acid sequence hybridizes to a specified nucleic acid target sequence to a detectably greater degree than its hybridization to non-target nucleic acid sequences. Selectively hybridizing sequences have at least 50%, or 60%, or 70%, or 80%, or 90% sequence identity or more, e.g., typically 95-100% sequence identity (i.e., complementarity) with each other.

A "sequence" of a nucleic acid refers to the order and identity of nucleotides in the nucleic acid. A sequence is typically read in the 5' to 3' direction.

A "sequence specific antibody" refers to an antibody that detectably binds to SARS-CoV nucleic acids.

A "sequencing reaction" refers to a reaction that includes, e.g., the use of terminator nucleotides and which is designed to elucidate the sequence of nucleotides in a given nucleic acid.

A "set" refers to a collection of at least two things. For example, a set may include 2, 3, 4, 5, 10, 20, 50, 100, 1,000 or other number of molecule or sequence types. For example, certain aspects of the invention include reaction mixtures having sets of amplicons. A "subset" refers to any portion of a set.

A "solid support" refers to a solid material that can be derivatized with, or otherwise attached to, a chemical moiety, such as an oligonucleotide or the like. Exemplary solid supports include plates, beads, microbeads, tubes, fibers, whiskers, combs, hybridization chips (including microarray substrates, such as those used in GeneChip® probe arrays (Affymetrix, Inc., Santa Clara, Calif., USA) and the like), membranes, single crystals, ceramic layers, self-assembling monolayers, and the like.

An oligonucleotide is "specific" for a target sequence if the number of mismatches present between the oligonucleotide and the target sequence is less than the number of mismatches present between the oligonucleotide and non-target sequences that might be present in a sample. Hybridization conditions can be chosen under which stable duplexes are formed only if the number of mismatches present is no more than the number of mismatches present between the oligonucleotide and the target sequence. Under such conditions, the target-specific oligonucleotide can form a stable duplex only with a target sequence. Thus, the use of target-specific primers under suitably stringent amplification conditions enables the specific amplification of those sequences, which contain the target primer binding sites. Similarly, the use of target-specific probes under suitably stringent hybridization conditions enables the detection of a specific target sequence.

A test nucleic acid is said to "specifically hybridize" to an oligonucleotide when it hybridizes at least one-half as well to the oligonucleotide as to the perfectly matched complementary target, i.e., with a signal to noise ratio at least one-half as high as hybridization of the oligonucleotide to the target under conditions in which the perfectly matched oligonucleotide binds to the perfectly matched complementary target with a signal to noise ratio that is at least about 5×-10× as high as that observed for hybridization to non-target nucleic acids present in a sample.

A "subject" refers to an organism. Typically, the organism is a mammalian organism, particularly a human organism. In certain embodiments, for example, a subject is a patient suspected of having a SARS-CoV infection.

A "subsequence" or "segment" refers to any portion of an entire nucleic acid sequence.

A "substantially identical variant" in the context of nucleic acids or polypeptides, refers to two or more sequences that have at least 85%, typically at least 90%, more typically at least 95% nucleotide or sequence identity to one another when compared and aligned for maximum correspondence, as measured using, e.g., a sequence comparison algorithm or by visual inspection. The substantial identity generally exists over a region of the sequences that is at least about 15 nucleotides or amino acids in length, more typically over a region that is at least about 20 nucleotides or amino acids in length, and even more typically the sequences are substantially identical over a region of at least about 25 nucleotides or amino acids in length. In some embodiments, for example, the sequences are substantially identical over the entire length of the nucleic acids or polypeptides being compared.

The term "substitution" in the context of a nucleic acid sequence refers to an alteration in which at least one nucleotide of the nucleic acid sequence is replaced by a different nucleotide.

The terms "target sequence," "target region," and "target nucleic acid" refer to a region of a nucleic acid, which is to be amplified, detected, or otherwise analyzed.

A "terminator nucleotide" refers to a nucleotide, which upon incorporation into a nucleic acid prevents further extension of the nucleic acid, e.g., by at least one nucleotide incorporating biocatalyst.

A "thermostable enzyme" refers to an enzyme that is stable to heat, is heat resistant and retains sufficient catalytic activity when subjected to elevated temperatures for selected periods of time. For example, a thermostable polymerase retains sufficient activity to effect subsequent primer extension reactions when subjected to elevated temperatures for the time necessary to effect denaturation of double-stranded nucleic acids. Heating conditions necessary for nucleic acid denaturation are well known in the art and are exemplified in U.S. Pat.

Nos. 4,683,202 and 4,683,195, which are both incorporated by reference. As used herein, a thermostable polymerase is typically suitable for use in a temperature cycling reaction such as the polymerase chain reaction ("PCR"). For a thermostable polymerase, enzymatic activity refers to the catalysis of the combination of the nucleotides in the proper manner to form primer extension products that are complementary to a template nucleic acid (e.g., SARS-CoV nucleic acids).

II. Overview

The Centers for Disease Control and Prevention (CDC) has sequenced the genome for a coronavirus believed to be responsible for the global epidemic of severe acute respiratory syndrome or SARS. FIG. 1 shows this nucleotide sequence of the SARS-CoV genome, which corresponds to GenBank® accession number AY278741. See also, Rota et al. (2003) "Characterization of a novel coronavirus associated with severe acute respiratory syndrome," Science 300 (5624):1394-1399, which is incorporated by reference. The sequence data confirm that the SARS coronavirus is a previously unrecognized coronavirus. All of the sequence, except for the leader sequence, was derived directly from viral RNA. The genome of the SARS coronavirus sequenced by the CDC is 29,727 nucleotides in length and the genome organization is similar to that of other coronaviruses. See, e.g., Drosten et al. (2003) "Identification of a novel coronavirus in patients with severe acute respiratory syndrome," N. Engl. J. Med. 348:1967-1976, which is incorporated by reference. Open reading frames corresponding to the polymerase protein (polymerase 1a, 1b), spike protein (S), small membrane protein (E), membrane protein (M) and nucleocapsid protein (N) have been identified.

The invention relates to the selective detection of SARS-CoV. In particular, based on new detection strategies utilizing selected target regions of the SARS-CoV genome, SARS-CoV infections can be diagnosed using the methods and reagents described herein. In certain embodiments, for example, certain nucleic acid detection reagents described herein target a region of the SARS-CoV genome that encodes an RNA-dependent RNA polymerase (RdRp), which has been shown to be stable against mutations compared to other regions of the SARS-CoV genome. The nucleic acid detection reagents described herein generally detectably bind, under selected assay conditions, to nucleotide sequences that are present in SARS-CoV, but which are not present in other species, thereby minimizing the occurrence of, e.g., false positives. The detection of SARS-CoV nucleic acids with certain nucleic acid detection reagents of the invention is illustrated in, for example, in the examples provided below. Many other features of the invention are also described herein.

To further illustrate, certain methods of the invention include contacting or incubating nucleic acid detection reagents with nucleic acids in or from samples derived from subjects (e.g., human patients suspected of having SARS-CoV infections, etc.). In certain embodiments, target regions of the nucleic acids in the samples are amplified prior to or simultaneously with being contacted with the nucleic acid detection reagents. These methods also include monitoring (e.g., at a single time point, at multiple discrete time points, continuously over a selected time period, etc.) binding between the nucleic acids and/or amplicons, and the nucleic acid detection reagents to determine whether the SARS-CoV is present in the samples, e.g., to diagnose patients from which the samples were derived, to monitor courses of treatment for patients diagnosed with SARS infections, and/or the like.

Other methods of the invention include contacting or incubating nucleic acids from samples with at least one pair of primer nucleic acids that include at least one nucleic acid having a sequence selected from the group consisting of: SEQ ID NOS: 1-12 and 15-24, a substantially identical variant thereof in which the variant has at least 90% sequence identity to one of SEQ ID NOS: 1-12 and 15-24, and complements of SEQ ID NOS: 1-12 and 15-24 and the variant, in nucleic acid amplification reactions. In addition, these methods also include detecting amplicons during or after the amplification reactions are performed to detect whether the SARS-CoV is present in the samples. These methods are also optionally repeated at selected time points.

In addition to compositions and reaction mixtures, the invention also relates to kits and systems for detecting SARS-CoV, and to related computers and computer readable media.

III. Nucleic Acid Detection Reagents

The nucleic acid detection reagents of the invention include various embodiments, including probe nucleic acids, primer nucleic acids, and sequence specific antibodies. In some embodiments, for example, certain nucleic acid detection reagents described herein target a segment of the SARS-CoV genome that encodes an RdRp. This region of the SARS-CoV genome is also referred to in, e.g., Ng et. (2004) "Detection of Severe Acute Respiratory Syndrome Coronavirus in Blood of Infected Patients" J. Clin. Microbiol. 42:347-350, which is incorporated by reference.

Exemplary nucleic acid detection reagents that target SARS-CoV nucleic acids include oligonucleotides comprising sequences selected from SEQ ID NOS: 1-12 and 15-24 or complements thereof. SEQ ID NOS: 1-12 and 15-24 are shown in Table I.

TABLE I

SEQ ID NO: 1  5'- TGATGGTTGTGTTCCACTCAACATC -3'

SEQ ID NO: 2  5'- ACACTGGTACAGGACAGGCAATTAC -3'

SEQ ID NO: 3  5'- GGTGTAAGTGCAGCCCGTCTTACAC -3'

SEQ ID NO: 4  5'- CGAATTTTGCTCACAGCATACAATG -3'

SEQ ID NO: 5  5'- ATTGGAGAGTACACCTTTGAAAAAG -3'

SEQ ID NO: 6  5'- GCTAGACTTCGTGCAAAACACTACG -3'

SEQ ID NO: 7  5'- TGTGGCTAGTTGTGATGCTATCATG -3'

SEQ ID NO: 8  5'- GCTACACATCACGATAAATTCACTG -3'

SEQ ID NO: 9  5'- CACTCAAATCTGCTACGTGTATTAC -3'

SEQ ID NO: 10 5'- CTCGCTATGGATGAATTCATACAGC -3'

SEQ ID NO: 11 5'- GGTTGGGATTATCCAAAATGTGA -3'

SEQ ID NO: 12 5'- GGCATCATCAGAAAGAATCATCAT -3'

SEQ ID NO: 15 5'- ACTATATGTTAAACCAGGTGG -3'

SEQ ID NO: 16 5'- ATTTACATTGGCTGTAACAGC -3'

SEQ ID NO: 17 5'- AGCTAACGAGTGTGCGCAAGTATTAAGTGAGA
                   TG -3'

SEQ ID NO: 18 5'- CCTCTCTTGTTCTTGCTCGCAAAC -3'

SEQ ID NO: 19 5'- AGAACAAGAGAGGCCATTATCCTAAG -3'

SEQ ID NO: 20 5'- TTAACATATAGTGAGCCGCCACAC -3'

SEQ ID NO: 21 5'- AGAGCCATGCCTAACAT -3'

TABLE I-continued

SEQ ID NO: 22 5'- GGTTGGGATTATCCAAAATGTGAC -3'

SEQ ID NO: 23 5'- GGTTGGGATTATCCAAAATGTGA -3'

SEQ ID NO: 24 5'- GTGTGGCGGCTCACTATATGTTA -3'

To further illustrate, FIG. 2 shows alignments of nucleotide sequences from various SARS-CoV isolates and from certain non-target organisms relative to one another. As shown, Group 1 shows the alignment of non-target nucleotide sequences from the Human Coronavirus (HCoV) 229E (Accession No. NC_002645) and the Porcine epidemic diarrhea virus (PEDV) (Accession No. NC_003436) with target nucleotide sequences from three different SARS-CoV isolates, namely, Toronto (Accession No. NC_004718), Singapore (Accession No. AY283794), and Guangzhou (Accession No. AY278489). As shown, the positions of oligonucleotides with sequences corresponding to SEQ ID NOS: 23 and 24 are underlined. Group 2 shows the alignment of non-target nucleotide sequences from the Bovine Coronavirus (BCoV) (Accession No. NC_003045) and the Murine hepatitis virus (MHV) (Accession No. NC_001846) with the target nucleotide sequences from the different SARS-CoV isolates shown in Group 1. The positions of oligonucleotides with sequences corresponding to SEQ ID NOS: 23 and 24 are also underlined in the alignment of Group 2. Group 3 illustrates the alignment of a non-target nucleotide sequence from the Avian Infectious Bronchitis Virus (IBV) (Accession No. NC_001451) with the target nucleotide sequences from the different SARS-CoV isolates shown in Group 1. The positions of oligonucleotides with sequences corresponding to SEQ ID NOS: 23 and 24 are also underlined in the alignment of Group 3.

As mentioned above, nucleic acid detection reagents comprise oligonucleotides (e.g., probe nucleic acids, primer nucleic acids, etc.) in certain embodiments of the invention. Although other lengths are optionally utilized, oligonucleotides generally comprise sequences that are typically between about 8 and about 100 nucleotides in length, more typically between about 10 and about 75 nucleotides in length, still more typically between about 12 and about 50 nucleotides in length, and even more typically between about 15 and about 35 nucleotides in length (e.g., about 20, about 25, or about 30 nucleotides in length). Methods of preparing oligonucleotides, such as nucleic acid synthesis, are described further below.

Various approaches can be utilized by one of skill in the art to design oligonucleotides (e.g., substantially identical variants of nucleic acids having sequences selected from SEQ ID NOS: 1-12 and 15-24 or complements thereof) that selectively bind to SARS-CoV nucleic acids. To illustrate, the DNAstar software package available from DNASTAR, Inc. (Madison, Wis., USA) can be used for sequence alignments. For example, nucleic acid sequences for the SARS-CoV genome and non-target sequences can be uploaded into DNAstar EditSeq program as individual files. To further illustrate, pairs of sequence files can be opened in the DNAstar MegAlign sequence alignment program and the Clustal W method of alignment can be applied. The parameters used for Clustal W alignments are optionally the default settings in the software. MegAlign typically does not provide a summary of the percent identity between two sequences. This is generally calculated manually. From the alignments, regions having, e.g., less than 85% identity with one another are typically identified and oligonucleotide sequences in these regions can be selected. Many other sequence alignment algorithms and software packages are also optionally utilized. Sequence alignment algorithms are also described in, e.g., Mount, *Bioinformatics: Sequence and Genome Analysis*, Cold Spring Harbor Laboratory Press (2001), and Durbin et al., *Biological Sequence Analysis: Probabilistic Models of Proteins and Nucleic Acids*, Cambridge University Press (1998), which are both incorporated by reference.

To further illustrate, optimal alignment of sequences for comparison can be conducted, e.g., by the local homology algorithm of Smith & Waterman (1981) *Adv. Appl. Math.* 2:482, by the homology alignment algorithm of Needleman & Wunsch (1970) *J. Mol. Biol.* 48:443, by the search for similarity method of Pearson & Lipman (1988) *Proc. Nat'l. Acad. Sci. USA* 85:2444, which are each incorporated by reference, and by computerized implementations of these algorithms (GAP, BESTFIT, FASTA, and TFASTA in the Wisconsin Genetics Software Package, Genetics Computer Group (Madison, Wis.), or by even by visual inspection.

Another example algorithm that is suitable for determining percent sequence identity is the BLAST algorithm, which is described in, e.g., Altschul et al. (1990) *J. Mol. Biol.* 215:403-410, which is incorporated by reference. Software for performing versions of BLAST analyses is publicly available through the National Center for Biotechnology Information on the world wide web at ncbi.nlm.nih.gov/ as of Apr. 20, 2004. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see, Henikoff & Henikoff (1989) *Proc. Natl. Acad. Sci. USA* 89:10915, which is incorporated by reference).

In addition to calculating percent sequence identity, the BLAST algorithm also performs a statistical analysis of the similarity between two sequences (see, e.g., Karlin & Altschul (1993) *Proc. Nat'l. Acad. Sci. USA* 90:5873-5787, which is incorporated by reference). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence (and, therefore, homologous) if the smallest sum probability in a comparison of the test nucleic acid to the reference nucleic acid is less than about 0.1, or less than about 0.01, and or even less than about 0.001.

An additional example of a useful sequence alignment algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle (1987) *J. Mol. Evol.* 35:351-360, which is incorporated by reference. The method used is similar to the method described by Higgins & Sharp (1989) *CABIOS* 5:151-153, which is incorporated by reference. The program can align, e.g., up to 300 sequences of a maximum length of 5,000 letters. The multiple alignment procedure begins with the pairwise alignment of the two most similar sequences, producing a cluster of two aligned sequences. This cluster can then be aligned to the next most related sequence or cluster of aligned sequences. Two clusters of sequences can be aligned by a simple extension of the pairwise alignment of two individual sequences. The final alignment is achieved by a series of progressive, pairwise alignments. The program can also be used to plot a dendogram or tree representation of clustering relationships. The program is run by designating specific sequences and their amino acid or nucleotide coordinates for regions of sequence comparison.

The probes and primers of the invention optionally include one or more labels, which are described further below. In addition, probes and primers optionally include various other modifications, such as modified nucleotides that alter hybridization melting temperatures, restriction site linkers to facilitate amplicon cloning, modifier groups that increase the specificity of nucleic acid amplification reactions, and/or the like. For example, certain modified nucleotides that increase nucleic acid hybridization melting temperatures are optionally included to permit the use of smaller probes and primers, such as those including between about 8 and about 14 nucleotides. Examples of these modified oligonucleotides include those having one or more LNA™ monomers. Nucleotide analogs such as these are described further in, e.g., U.S. Pat. No. 6,639,059, entitled "SYNTHESIS OF [2.2.1]BICYCLO NUCLEOSIDES," issued Oct. 28, 2003 to Kochkine et al., U.S. Pat. No. 6,303,315, entitled "ONE STEP SAMPLE PREPARATION AND DETECTION OF NUCLEIC ACIDS IN COMPLEX BIOLOGICAL SAMPLES," issued Oct. 16, 2001 to Skouv, and U.S. Pat. Application Pub. No. 2003/0092905, entitled "SYNTHESIS OF [2.2.1]BICYCLO NUCLEOSIDES," by Kochkine et al. that published May 15, 2003, which are each incorporated by reference. Oligonucleotides comprising LNA™ monomers are commercially available through, e.g., Exiqon A/S (Vedbaek, DK). Additional probe and primer modifications are referred to herein, including in the definitions provided above.

In certain embodiments, the nucleic acid detection reagents utilized as described herein are sequence specific antibodies that target SARS-CoV nucleic acids. Antibodies suitable for use in these embodiments of invention may be prepared by conventional methodology and/or by genetic engineering. Antibody fragments may be genetically engineered, e.g., from the variable regions of the light and/or heavy chains ($V_H$ and $V_L$), including the hypervariable regions, or from both the $V_H$ and $V_L$ regions. For example, the term "antibodies" as used herein includes polyclonal and monoclonal antibodies and biologically active fragments thereof including among other possibilities "univalent" antibodies (Glennie et al. (1982) *Nature* 295:712); Fab proteins including Fab' and F(ab')$_2$ fragments whether covalently or non-covalently aggregated; light or heavy chains alone, typically variable heavy and light chain regions ($V_H$ and $V_L$ regions), and more typically including the hypervariable regions (otherwise known as the complementarity determining regions (CDRs) of the $V_H$ and $V_L$ regions); $F_c$ proteins; "hybrid" antibodies capable of binding more than one antigen; constant-variable region chimeras; "composite" immunoglobulins with heavy and light chains of different origins; "altered" antibodies with improved specificity and other characteristics as prepared by standard recombinant techniques, by mutagenic techniques, or other directed evolutionary techniques known in the art.

The sequence specific antibodies utilized as described herein may be labeled or unlabeled. Suitable labels include, e.g., radionuclides, enzymes, coenzymes, fluorescent dyes, chemiluminescent dyes, chromogens, enzyme substrates or co-factors, enzyme inhibitors, free radicals, and the like. Such labeled reagents may be used in a variety of well known assays, such as radioimmunoassays, enzyme immunoassays, e.g., ELISA, fluorescent immunoassays, and the like. See, e.g., U.S. Pat. Nos. 3,766,162; 3,791,932; 3,817,837; and 4,233,402, which are each incorporated by reference. Additional labels are described further herein.

In some embodiments, polypeptides, such the RdRp referred to above are targeted for detection. Many techniques for detecting proteins are known in the art. For example, various electrophoretic assays (e.g., SDS-PAGE or the like), immunoassays, mass spectrometric assays (e.g., matrix assisted laser desorption/ionization (MALDI)-based analyses, surface enhanced laser desorption/ionization (SELDI)-based assays, etc.), and/or other approaches can be used to detect proteins encoded by SARS-CoV nucleic acids. Many of these and other suitable protein detection methods are described in the references cited herein.

In practicing the present invention, many conventional techniques in molecular biology and recombinant DNA are optionally used. These techniques are well known and are explained in, for example, *Current Protocols in Molecular Biology*, Volumes I, II, and III, 1997 (F. M. Ausubel ed.); Sambrook et al., *Molecular Cloning: A Laboratory Manual*, 3rd Ed., Cold Spring Harbor Laboratory Press, Cold Spring Harbor, N.Y., 2001; Berger and Kimmel, *Guide to Molecular Cloning Techniques, Methods in Enzymology* volume 152 Academic Press, Inc., San Diego, Calif. (Berger), *DNA Cloning: A Practical Approach*, Volumes I and II, 1985 (D. N. Glover ed.); *Oligonucleotide Synthesis*, 1984 (M. L. Gait ed.); *Nucleic Acid Hybridization*, 1985, (Hames and Higgins); *Transcription and Translation*, 1984 (Hames and Higgins eds.); *Animal Cell Culture*, 1986 (Freshney ed.); *Immobilized Cells and Enzymes*, 1986 (IRL Press); Perbal, 1984, *A Practical Guide to Molecular Cloning;* the series, *Methods in Enzymology* (Academic Press, Inc.); *Gene Transfer Vectors for Mammalian Cells*, 1987 (J. H. Miller and M. P. Calos eds., Cold Spring Harbor Laboratory); *Methods in Enzymology* Vol. 154 and Vol. 155 (Wu and Grossman, and Wu, eds., respectively), all of which are incorporated by reference.

IV. Sequence Variations

Numerous nucleic acid and polypeptide sequences are within the scope of the present invention, whether as target sequences or the agents used to detect those target sequences.

Silent Variations

It will be appreciated by those skilled in the art that due to the degeneracy of the genetic code, a multitude of SARS-CoV nucleic acids sequences encoding polypeptides may be produced, some of which may bear minimal sequence homology to the nucleic acid sequences explicitly disclosed herein. For instance, inspection of the codon table (Table II) shows that codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

TABLE II

Codon Table

| Amino acids | | | Codon | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

Such "silent variations" are one species of "conservatively modified variations", discussed below. One of skill will recognize that each codon in a nucleic acid (except AUG, which is ordinarily the only codon for methionine) can be modified by standard techniques to encode a functionally identical polypeptide. Accordingly, each silent variation of a nucleic acid, which encodes a polypeptide is implicit in any described sequence. For example, the invention provides each and every possible variation of nucleic acid sequence encoding an RdRp of a SARS-CoV that could be made by selecting combinations based on possible codon choices. These combinations are made in accordance with the standard triplet genetic code (e.g., as set forth in Table II) as applied to the nucleic acid sequences encoding, e.g., an RdRp of a SARS-CoV. All such variations of every nucleic acid herein are specifically provided and described by consideration of the sequence in combination with the genetic code.

Conservative Variations

"Conservatively modified variations" or, simply, "conservative variations" of a particular nucleic acid sequence refers to those nucleic acids, which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

Conservative substitution tables providing functionally similar amino acids are well known in the art. Table III sets forth six groups, which contain amino acids that are "conservative substitutions" for one another.

TABLE III

Conservative Substitution Groups

| | | | |
|---|---|---|---|
| 1 | Alanine (A) | Serine (S) | Threonine (T) |
| 2 | Aspartic acid (D) | Glutamic acid (E) | |
| 3 | Asparagine (N) | Glutamine (Q) | |
| 4 | Arginine (R) | Lysine (K) | |
| 5 | Isoleucine (I) | Leucine (L) | Methionine (M) | Valine (V) |
| 6 | Phenylalanine (F) | Tyrosine (Y) | Tryptophan (W) |

Thus, "conservatively substituted variations" of, e.g., an RdRp of a SARS-CoV include substitutions of a small percentage, typically less than 5%, more typically less than 2% or 1%, of the amino acids of the polypeptide sequence, with a conservatively selected amino acid of the same conservative substitution group.

The addition of sequences that do not alter the encoded activity of a nucleic acid molecule, such as the addition of a non-functional sequence, is a conservative variation of the basic nucleic acid.

One of skill will appreciate that many conservative variations of the nucleic acids described herein yield a functionally identical nucleic acid. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence, which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

V. Oligonucleotide Synthesis

The oligonucleotides of the invention are optionally prepared using essentially any technique known in the art. In certain embodiments, for example, the oligonucleotides described herein are synthesized chemically using essentially any nucleic acid synthesis method, including, e.g., according to the solid phase phosphoramidite triester method described by Beaucage and Caruthers (1981), *Tetrahedron Letts.* 22(20):1859-1862, which is incorporated by reference, or another synthesis technique known in the art, e.g., using an automated synthesizer, as described in Needham-VanDevanter et al. (1984) *Nucleic Acids Res.* 12:6159-6168, which is incorporated by reference. A wide variety of equipment is commercially available for automated oligonucleotide synthesis. Multi-nucleotide synthesis approaches (e.g., tri-nucleotide synthesis, etc.) are also optionally utilized. Moreover, the primer nucleic acids described herein optionally include various modifications. In certain embodiments, for example, primers include restriction site linkers, e.g., to facilitate subsequent amplicon cloning or the like. To further illustrate, primers are also optionally modified to improve the specificity of amplification reactions as described in, e.g., U.S. Pat. No. 6,001,611, entitled "MODIFIED NUCLEIC ACID AMPLIFICATION PRIMERS," issued Dec. 14, 1999 to Will, which is incorporated by reference. Primers and probes can also be synthesized with various other modifications as described herein or as otherwise known in the art.

Essentially any label is optionally utilized to label the nucleic acid detection reagents of the invention. In some embodiments, for example, the label comprises a fluorescent dye (e.g., a rhodamine dye (e.g., R6G, R110, TAMRA, ROX, etc.), a fluorescein dye (e.g., JOE, VIC, TET, HEX, FAM, etc.), a halofluorescein dye, a cyanine dye (e.g., CY3, CY3.5, CY5, CY5.5, etc.), a BODIPY® dye (e.g., FL, 530/550, TR, TMR, etc.), an ALEXA FLUOR® dye (e.g., 488, 532, 546, 568, 594, 555, 653, 647, 660, 680, etc.), a dichlororhodamine dye, an energy transfer dye (e.g., BIGDYE™ v 1 dyes, BIGDYE™ v 2 dyes, BIGDYE™ v 3 dyes, etc.), Lucifer dyes (e.g., Lucifer yellow, etc.), CASCADE BLUE®, Oregon Green, and the like. Additional examples of fluorescent dyes are provided in, e.g., Haugland, *Molecular Probes Handbook of Fluorescent Probes and Research Products*, Ninth Ed. (2003) and the updates thereto, which are each incorporated by reference. Fluorescent dyes are generally readily available from various commercial suppliers including, e.g., Molecular Probes, Inc. (Eugene, Oreg.), Amersham Biosciences Corp. (Piscataway, N.J.), Applied Biosystems (Foster City, Calif.), etc. Other labels include, e.g., biotin, weakly fluorescent labels (Yin et al. (2003) *Appl Environ Microbiol.* 69(7):3938, Babendure et al. (2003) *Anal. Biochem.* 317(1):1, and Jankowiak et al. (2003) *Chem Res Toxicol.* 16(3):304), non-fluorescent labels, colorimetric labels, chemiluminescent labels (Wilson et al. (2003) *Analyst.* 128(5):480 and Roda et al. (2003) *Luminescence* 18(2):72), Raman labels, electrochemical labels, bioluminescent labels (Kitayama et al. (2003) *Photochem Photobiol.* 77(3):333, Arakawa et al. (2003) *Anal. Biochem.* 314(2):206, and Maeda (2003) *J. Pharm. Biomed. Anal.* 30(6):1725), and an alpha-methyl-PEG labeling reagent as described in, e.g., U.S. Provisional Patent Application No. 60/428,484, filed on Nov. 22, 2002, which references are each incorporated by reference. Nucleic acid labeling is also described further below.

In addition, essentially any nucleic acid (and virtually any labeled nucleic acid, whether standard or non-standard) can be custom or standard ordered from any of a variety of commercial sources, such as The Midland Certified Reagent Company, The Great American Gene Company, ExpressGen Inc., Operon Technologies Inc., Proligo LLC, and many others.

VI. Sample Preparation and Nucleic Acid Amplification

Samples are generally derived or isolated from subjects, typically mammalian subjects, more typically human subjects, suspected of having a SARS-CoV infection. Exemplary samples or specimens include blood, plasma, serum, feces, bronchoalveolar lavage, nasal pharyngeal swabs and tissues, urine, synovial fluid, seminal fluid, seminal plasma, prostatic fluid, vaginal fluid, cervical fluid, uterine fluid, cervical scrapings, amniotic fluid, anal scrapings, mucus, sputum, tissue, and the like. Essentially any technique for acquiring these samples is optionally utilized including, e.g., scraping, venipuncture, swabbing, biopsy, or other techniques known in the art. Methods of storing specimens, culturing cells, isolating and preparing nucleic acids from these sources are generally known in the art and many of these are described further in the references and/or examples provided herein. A detailed description of recommended facilities, practices, and protective equipment for the various laboratory biosafety levels (BSLs) may also be found in the CDC/NIH Biosafety in Microbiological and Biomedical Laboratories manual (BMBL), which is available on the world wide web at cdc.gov/od/ohs/biosfty/bmbl4/bmbl4toc.htm as of Apr. 20, 2004.

To illustrate, blood and urine specimens may be handled using Standard Precautions (previously Universal Precautions) in BSL-2 laboratories. Laboratory workers should wear protective equipment, including disposable gloves, laboratory coats, eye protection and a surgical mask, or face shield to provide a barrier to mucosal surface exposure. Careful attention should be given to hand hygiene after removal of gloves and especially before touching the eyes or mucosal surfaces.

Any procedure with the potential to generate fine particulate aerosols (e.g. vortexing or sonication of specimens in an open tube) should be performed in a biological safety cabinet (BSC). The use of sealed centrifuge rotors or sample cups, if available, should be employed for centrifugation. Ideally, these rotors or cups should be unloaded in a BSC.

Procedures performed outside of a BSC should be performed in a manner that minimizes the risk of exposure to an inadvertent sample release.

Work surfaces and equipment should be decontaminated after specimens are processed. Standard decontamination agents that are effective against lipid-enveloped viruses should be sufficient.

If the safety equipment described above is not available, administrative measures and/or additional personal protective equipment may be employed to reduce risk. This should be done in the context of a careful risk assessment by the laboratory safety officer. For example, the workflow of the laboratory may be adjusted so that a minimum number of workers are present during centrifugation.

Consideration may be given to implementing respiratory protection for workers for use during centrifugation or other procedures with increased potential for inadvertent sample release. Acceptable methods of respiratory protection include a properly fit tested NIOSH approved filter respirator (N-95 or higher); or powered air-purifying respirators (PAPRs) equipped with high efficiency particulate air (HEPA) filters. Accurate fit testing is a key component of effective respirator use. Personnel who cannot wear fitted respirators because of facial hair or other fit-limitations should wear loose fitting hooded or helmeted PAPRs.

Consideration may also be given to referral of specimens to a suitably equipped reference laboratory.

To further illustrate, prior to analyzing the target nucleic acids described herein, those nucleic acids may be purified or isolated from samples that typically include complex mixtures of different components. Cells in collected samples are typically lysed to release the cell contents. For example, cells suspected of being infected with SARS-CoV in the particular sample can be lysed by contacting them with various enzymes, chemicals, and/or lysed by other approaches known in the art. In some embodiments, nucleic acids are analyzed directly in the cell lysate. In other embodiments, nucleic acids are further purified or extracted from cell lysates prior to detection. Essentially any nucleic acid extraction methods can be used to purify nucleic acids in the samples utilized in the methods of the present invention. Exemplary techniques that can be used to purifying nucleic acids include, e.g., affinity chromatography, hybridization to probes immobilized on solid supports, liquid-liquid extraction (e.g., phenol-chloroform extraction, etc.), precipitation (e.g., using ethanol, etc.), extraction with filter paper, extraction with micelle-forming reagents (e.g., cetyl-trimethyl-ammonium-bromide, etc.), binding to immobilized intercalating dyes (e.g., ethidium bromide, acridine, etc.), adsorption to silica gel or diatomic earths, adsorption to magnetic glass particles or organo silane particles under chaotropic conditions, and/or the like. Sample processing is also described in, e.g., U.S. Pat. Nos. 5,155,018, 6,383,393, and 5,234,809, which are each incorporated by reference.

To further exemplify, unmodified nucleic acids can bind to a material with a silica surface. Many of these processes that are optionally adapted for use in the performing the methods of the present invention are described in the art. To illustrate, Vogelstein et al. (1979) *Proc. Natl. Acad. Sci. USA* 76:615-619, which is incorporated by reference, describes the purification of nucleic acids from agarose gels in the presence of sodium iodide using ground flint glass. Marko et al. (1982) *Anal. Biochem.* 121:382-387, which is incorporated by reference, describes the purification of nucleic acids from bacteria on glass dust in the presence of sodium perchlorate. In DE-A 3734442, which is incorporated by reference, nucleic acids are isolated on glass fiber filters. The nucleic acids bound to these glass fiber filters are washed and then eluted with a methanol-containing Tris/EDTA buffer. A similar procedure is described in Jakobi et al. (1988) *Anal. Biochem.* 175:196-201, which is incorporated by reference. In particular, Jakobi et al. describes the selective binding of nucleic acids to glass surfaces in chaotropic salt solutions and separating the nucleic acids from contaminants, such as agarose, proteins, and cell residue. To separate the glass particles from the contaminants, the particles can be centrifuged or fluids can be drawn through the glass fiber filters. In addition, the use of magnetic particles to immobilize nucleic acids after precipitation by adding salt and ethanol is described in, e.g., Alderton et al. (1992) *Anal. Biochem.* 201:166-169 and PCT/GB91/00212, which are both incorporated by reference. In this procedure, the nucleic acids are agglutinated along with the magnetic particles. The agglutinate is separated from the original solvent by applying a magnetic field and performing one or more washing steps. After at least one wash step, the nucleic acids are typically dissolved in a Tris buffer.

Magnetic particles in a porous glass matrix that is covered with a layer that includes, e.g., streptavidin can also be utilized in certain embodiments of the invention. These particles can be used, e.g., to isolate biotin-conjugated nucleic acids and proteins. Ferrimagnetic, ferromagnetic, and superparamagnetic particles are also optionally utilized. Magnetic glass particles and related methods that can be adapted for using in performing the methods described herein are also described in, e.g., WO 01/37291, which is incorporated by reference.

One of the most powerful and basic technologies for deriving and detecting nucleic acids is nucleic acid amplification. In the present invention, amplification of nucleic acids of interest typically precedes or is concurrent with the detection of that DNA. In addition, the oligonucleotides described herein are also optionally amplified, e.g., following chemical synthesis or the like. In some embodiments, detectable signals are amplified, e.g., using branched nucleic acid or other signal amplification formats known in the art.

Amplification methods that are optionally utilized or adapted for use with the oligonucleotides and methods described herein include, e.g., various polymerase or ligase mediated amplification methods, such as the polymerase chain reaction (PCR), reverse transcription PCR (RT-PCR), the ligase chain reaction (LCR), strand displacement amplification (SDA), nucleic acid sequence-based amplification (NASBA), rolling circle amplification (RCA), and/or the like. Details regarding the use of these and other amplification methods can be found in various articles and/or any of a variety of standard texts, including, e.g., Berger, Sambrook, Ausubel, and *PCR Protocols A Guide to Methods and Applications* (Innis et al. eds) Academic Press, Inc., San Diego, Calif. (1990) (Innis), Schweitzer et al. (2001) "Combining nucleic acid amplification and detection," *Curr Opin Biotechnol.* 12(1):21-27, all of which are incorporated by reference. Many available biology texts also have extended discussions regarding PCR and related amplification methods. Nucleic acid amplification is also described in, e.g., Mullis et al., (1987) U.S. Pat. No. 4,683,202 and Sooknanan and Malek (1995) *Biotechnology* 13:563, which are both incorporated by reference. Improved methods of amplifying large nucleic acids by PCR are summarized in Cheng et al. (1994) *Nature* 369:684, which is incorporated by reference. In certain embodiments, duplex PCR is utilized to amplify target nucleic acids. Duplex PCR amplification is described further in, e.g., Gabriel et al. (2003) "Identification of human remains by immobilized sequence-specific oligonucleotide analysis of mtDNA hypervariable regions I and II," *Croat. Med. J.* 44(3)293 and La et al. (2003) "Development of a duplex PCR assay for detection of Brachyspira hyodysenteriae and Brachyspira pilosicoli in pig feces," *J. Clin. Microbiol.* 41(7):3372, which are both incorporated by reference. Optionally, labeled primers (e.g., biotinylated primers, Scorpion primers, etc.) are utilized to amplify nucleic acids in a sample, e.g., to facilitate the detection of amplicons and the like. Scorpion primers are also described in, e.g., Whitcombe et al. (1999) "Detection of PCR products using self-probing amplicons and fluorescence" *Nat Biotechnol.* 17(8):804-807, which is incorporated by reference. Labeling is described further herein.

Amplicons are optionally recovered and purified from other reaction components by any of a number of methods well known in the art, including electrophoresis, chromatography, precipitation, dialysis, filtration, and/or centrifugation. Aspects of nucleic acid purification are described in, e.g., Douglas et al., *DNA Chromatography*, Wiley, John & Sons, Inc. (2002), and Schott, *Affinity Chromatography: Template Chromatography of Nucleic Acids and Proteins*, Chromatographic Science Series, #27, Marcel Dekker (1984), all of which are incorporated by reference. In certain embodiments, amplicons are not purified prior to detection. The detection of amplicons is described further below.

Nested PCR

The present invention provides methods for detecting SARS-CoV in samples and typing the coronavirus. An exemplary method is as follows:

(a) Nested PCR using two sets of amplification primers. The target DNA sequence of one set of primer (termed "inner" primers) is located within the target sequence of the second set of primers (termed "outer" primers). In practice, a standard PCR reaction is first run with the patient sample using the "outer primers". Then a second PCR reaction is run with the "inner primers" using the product of the first reaction as the amplification target. This procedure increases the sensitivity of the assay by reamplifying the product of the first reaction in a second reaction. The specificity of the assay is increased because the inner primers amplify only if the first PCR reaction yielded a specific product. A schematic depiction of a nested PCR procedure is shown in FIG. 3.

(b) Treating the sample with consensus SARS virus primer nucleic acids, an agent for polymerization, and deoxynucleoside 5'-triphosphates under hybridizing conditions, in which consensus SARS virus primers are mixtures of oligonucleotides that comprise at least one pair of primers sufficiently complementary to the target region of the SARS-CoV genome to hybridize therewith such that extension products or amplicons are synthesized from at least one member of the pair. When separated from complementary strands, the amplicons can serve as templates for synthesis of extension products or amplicons of the other member of the pair of primer nucleic acids;

(c) Treating the sample under denaturing conditions to separate the primer extension products or amplicons from their templates to provide single-stranded molecules;

(d) Treating the products of step (b) with the consensus primers of the step (a) under conditions such that additional primer extension products are synthesized using the single-stranded molecules produced in step (c) as a template;

(e) Repeating steps (b)-(d) to synthesize detectable amounts of target SARS-CoV amplicons to providing amplified SARS-CoV sequences;

(f) Determining if amplification has occurred by treating the reaction mixture prepared in step (d) under hybridizing conditions with a generic probe and determining if hybridization and amplification has occurred; and, (g) Hybridizing a type-specific DNA probe to the amplified DNA and determining if hybridization has occurred.

Amplification of nucleic acids by the polymerase chain reaction is also described in U.S. Pat. Nos. 4,683,202 and 4,683,195, which are both incorporated by reference. In general, PCR amplification of nucleic acids involves repeated cycles of heat-denaturing the nucleic acids, annealing oligonucleotide primers to sequences that flank the nucleic acid segment to be amplified, and extending the annealed primers with a polymerase. The primers hybridize to opposite strands of the target sequence and are oriented such that nucleic acid synthesis by the polymerase proceeds across the region between the primers, effectively doubling the amount of the target nucleic acid synthesized in the previous cycle. This results in the exponential accumulation of the target nucleic acids.

The choice of primers for use in PCR typically determines the specificity of the amplification reaction. In the amplification steps of the method of the present invention, "consensus" primers are used that will amplify SARS-CoV sequences present in a sample, regardless of type. The consensus primers of the invention can include degenerate primers, mixtures of the oligonucleotides synthesized so that any one several nucleotides can be incorporated into a primer are sufficiently complementary to all types of SARS-CoV to amplify a nucleic acid sequence of any SARS-CoV present in the sample.

The present invention may also lead to the discovery of previously unknown strains or types of SARS-CoVs.

5'-Nuclease Reactions

The oligonucleotides of the invention can also be utilized as 5'-nuclease probes for the real-time detection of SARS-CoV in 5'-nuclease PCR reactions.

5'-nuclease reactions typically use 5'-nuclease probes to detect specific PCR products by employing the 5'-->3' exonuclease activity of, e.g., Taq DNA polymerase. In certain embodiments, 5'-nuclease probes are blocked to prohibit extension at their 3' ends. 5'-nuclease probes typically include site-specific sequences and are labeled with a fluorescent reporter dye and a fluorescent quencher dye. Typically, 5'-nuclease probes hybridize to target sequences downstream from the 3' ends of primer sequences used for the PCR reactions. During PCR the 5'-nuclease probes hybridizes to its complementary single strand nucleic sequence within the target region. When amplification occurs 5'-nuclease probes are degraded due to the 5'-->3' exonuclease activity of, e.g., Taq DNA polymerase, thereby separating the quencher from the reporter during extension. Due to the release of the quenching effect on the reporter, the detectable fluorescence intensity of the reporter dye increases. During the amplification process this light emission generally increases exponentially. Light emission from the reporter dye is typically monitored spectrophotometrically. Because increase of the fluorescence intensity of the reporter dye is only achieved when probe hybridization and amplification of the target sequence has occurred, 5'-nuclease assays offer sensitive methods (viral nucleic acids at a concentration of only a few cfu/ml can be detected) to determine the presence or absence of specific sequences. Therefore, this technique is particularly useful in diagnostic applications, such as the screening of samples for the detection of SARS-CoV in clinical samples.

Exemplary probes useful for detection of the SARS-COV in samples in 5'-nuclease reactions include, e.g., oligonucleotides having sequences corresponding to SEQ ID NOS: 17 and 21. To illustrate, a 5'-nuclease probe can incorporate a FAM fluorophore at the 5' end and the TAMRA quencher at the 3' end. To further illustrate, a 5'-nuclease probe with a sequence corresponding to SEQ ID NO: 21 is optionally used in real-time PCR reactions with primer nucleic acids having sequences corresponding to SEQ ID NO: 11 and SEQ ID NO: 20 in certain embodiments of the invention.

Example conditions optionally used in 5'-nuclease nuclease reactions to detect SARS-CoV in samples are shown below. Reaction Conditions II are generally more useful if the target nucleic acid is expected to be present in a relatively high proportion. Optimization of reaction conditions is considered within the skill of the ordinary practitioner of the art.

| REACTION CONDITIONS I | |
|---|---|
| 2.5 μl 10X TaqMan ® A Buffer | 1X |
| 3.0 μl 25 mM $MgCl_2$ | 3 mM |
| .75 μl 10 mM dATP | 300 μM |
| .75 μl 10 mM dCTP | 300 μM |
| .75 μl 10 mM dGTP | 300 μM |
| .75 μl 20 mM dUTP | 600 μM |
| .075 μl 100 μM forward primer | 300 nM |
| .225 μl 100 μM reverse primer | 900 nM |
| .25 μl 10 μM probe (SEQ ID NO: 17 or 21) | 100 nM |
| .125 μl Amplitaq Gold ® (5 U/μl) | .025 U/μl |
| .25 μl AmpErase ® UNG (1 U/μl) | .01 U/μl |
| 13.575 μl Nuclease-free water | |
| 2.0 μl DNA standard/sample | |
| total volume = 25 μl | |

| CYCLING CONDITIONS |
|---|
| 50° C. for 2 min |
| 60° C. for 30 min |
| 95° C. for 5 min |
| 40 cycles of 95° C. 15 and 60° C. for 1 min |
| 25° C. for 2 min |

| REACTION CONDITIONS II | |
|---|---|
| 5 μl 10X TaqMan ® Buffer A | 1X |
| 11 μl 25 mM $MgCl_2$ | 5.5 mM |
| 11 μl 25 mM $MgCl_2$ | 5.5 mM |
| 1 μl 10 mM dATP | 200 μM |
| 1 μl 10 mM dCTP | 200 μM |
| 1 μl 10 mM dGTP | 200 μM |

-continued

| | |
|---|---|
| 1 µl 20 mM dUTP | 400 µM |
| 1 µl 10 µM forward primer | 200 nM |
| 1 µl 10 µM reverse primer | 200 nM |
| 1 µl 10 µM probe (SEQ ID NO: 17 or 21) | 100 nM |
| .5 AmpliTaq Gold ® (5 U/µl) | .05 U/µl |
| .5 µl AmpErase ® UNG (1 U/µl) | .01 U/µl |
| 1.25 µl 2% glycerin | 0.05% |
| 23.08 µl RNase-free water | |
| 1.67 µl DNA standard/sample | | total volume = 50 µl

CYCLING CONDITIONS

50° C. for 2 min
95° C. for 5 min
40 cycles of 95° C. for 15 sec
and 60° C. for 1 min
25° C. for 2 min An exhaustive manual for conducting RT-PCR using 5'-nuclease reactions is available from Applied Biosystems, "TaqMan® One-Step RT-PCR Master Mix Reagents Kit Protocol", printed April 2002, as part no. 4310299 Rev. C., hereby incorporated in its entirety by reference. The publication was available on the world wide web at ucl.ac.uk/wibr/2/services/reldocs/1steppcr.pdf as of Apr. 20, 2004.

VII. Oligonucleotide Arrays

In certain embodiments of the invention, the oligonucleotides described herein are covalently or noncovalently attached to solid supports which are then contacted with samples comprising amplified and labeled nucleic acid from a subject. In other embodiments, the oligonucleotides of the invention are provided free in solution. Essentially any substrate material is optionally adapted for use in these aspects of the invention. In certain embodiments, for example, substrates are fabricated from silicon, glass, or polymeric materials (e.g., glass or polymeric microscope slides, silicon wafers, etc.). Suitable glass or polymeric substrates, including microscope slides, are available from various commercial suppliers, such as Fisher Scientific (Pittsburgh, Pa.) or the like. In some embodiments, solid supports utilized in the invention are membranes. Suitable membrane materials are optionally selected from, e.g. polyaramide membranes, polycarbonate membranes, porous plastic matrix membranes (e.g., POREX® Porous Plastic, etc.), porous metal matrix membranes, polyethylene membranes, poly(vinylidene difluoride) membranes, polyamide membranes, nylon membranes, ceramic membranes, polyester membranes, polytetrafluoroethylene (TEFLON®) membranes, woven mesh membranes, microfiltration membranes, nanofiltration membranes, ultrafiltration membranes, dialysis membranes, composite membranes, hydrophilic membranes, hydrophobic membranes, polymer-based membranes, a non-polymer-based membranes, powdered activated carbon membranes, polypropylene membranes, glass fiber membranes, glass membranes, nitrocellulose membranes, cellulose membranes, cellulose nitrate membranes, cellulose acetate membranes, polysulfone membranes, polyethersulfone membranes, polyolefin membranes, or the like. Many of these membranous materials are widely available from various commercial suppliers, such as, P. J. Cobert Associates, Inc. (St. Louis, Mo.), Millipore Corporation (Bedford, Mass.), or the like. Other exemplary solid supports that-are optionally utilized include, e.g., ceramics, metals, resins, gels, plates, beads, microbeads (e.g., magnetic microbeads, etc.), tubes (e.g., microtubes, etc.), whiskers, fibers, combs, single crystals, and self-assembling monolayers.

The oligonucleotides of the invention are directly or indirectly (e.g., via linkers, such as bovine serum albumin (BSA) or the like) attached to the supports, e.g., by any available chemical or physical method. A wide variety of linking chemistries are available for linking molecules to a wide variety of solid supports. More specifically, nucleic acids may be attached to the solid support by covalent binding such as by conjugation with a coupling agent or by non-covalent binding such as electrostatic interactions, hydrogen bonds or antibody-antigen coupling, or by combinations thereof. Typical coupling agents include biotin/avidin, biotin/streptavidin, *Staphylococcus aureus* protein A/IgG antibody $F_c$ fragment, and streptavidin/protein A chimeras (Sano et al. (1991) *Bio/Technology* 9:1378, which is incorporated by reference), or derivatives or combinations of these agents. Nucleic acids may be attached to the solid support by a photocleavable bond, an electrostatic bond, a disulfide bond, a peptide bond, a diester bond or a combination of these bonds. Nucleic acids are also optionally attached to solid supports by a selectively releasable bond such as 4,4'-dimethoxytrityl or its derivative. Derivatives which have been found to be useful include 3 or 4 [bis-(4-methoxyphenyl)]-methyl-benzoic acid, N-succinimidyl-3 or 4 [bis-(4-methoxyphenyl)]-methyl-benzoic acid, N-succinimidyl-3 or 4 [bis-(4-methoxyphenyl)]-hydroxymethyl-benzoic acid, N-succinimidyl-3 or 4 [bis-(4-methoxyphenyl)]-chloromethyl-benzoic acid, and salts of these acids.

As referred to above, oligonucleotides are optionally attached to solid supports via linkers between the nucleic acids and the solid support. Useful linkers include a coupling agent, as described above for binding to other or additional coupling partners, or to render the attachment to the solid support cleavable.

Cleavable attachments can be created by attaching cleavable chemical moieties between the oligonucleotides and the solid support including, e.g., an oligopeptide, oligonucleotide, oligopolyamide, oligoacrylamide, oligoethylene glycerol, alkyl chains of between about 6 to 20 carbon atoms, and combinations thereof. These moieties may be cleaved with, e.g., added chemical agents, electromagnetic radiation, or enzymes. Exemplary attachments cleavable by enzymes include peptide bonds which can be cleaved by proteases, and phosphodiester bonds which can be cleaved by nucleases.

Chemical agents such as β-mercaptoethanol, dithiothreitol (DTT) and other reducing agents cleave disulfide bonds. Other agents which may be useful include oxidizing agents, hydrating agents and other selectively active compounds. Electromagnetic radiation such as ultraviolet, infrared and visible light cleave photocleavable bonds. Attachments may also be reversible, e.g., using heat or enzymatic treatment, or reversible chemical or magnetic attachments. Release and reattachment can be performed using, e.g., magnetic or electrical fields.

Array based hybridization is particularly suitable for detecting SARS-CoV nucleic acids, as it can be used to detect the presence of many amplicons simultaneously. A number of array systems have been described and can be adapted for use with the present invention, including those available from commercial suppliers such as Affymetrix, Inc. (Santa Clara, Calif., USA) and the like. Aspects of array construction and use are also described in, e.g., Sapolsky et al. (1999) "High-throughput polymorphism screening and genotyping with high-density oligonucleotide arrays." *Genetic Analysis: Biomolecular Engineering* 14:187-192; Lockhart (1998) "Mutant yeast on drugs" *Nature Medicine* 4:1235-1236;

Fodor (1997) "Genes, Chips and the Human Genome." *FASEB Journal* 11:A879; Fodor (1997) "Massively Parallel Genomics" *Science* 277: 393-395; and Chee et al. (1996) "Accessing Genetic Information with High-Density DNA Arrays" *Science* 274:610-614, all of which are incorporated by reference.

VIII. Nucleic Acid Hybridization

Hybridization of oligonucleotides to their target SARS-CoV nucleic acids can be accomplished by choosing the appropriate hybridization conditions. The stability of the probe target nucleic acid hybrid is typically selected to be compatible with the assay and washing conditions so that stable, detectable hybrids form only between the probes and target SARS-CoV nucleic acids. Manipulation of one or more of the different assay parameters determines the exact sensitivity and specificity of a particular hybridization assay.

More specifically, hybridization between complementary bases of DNA, RNA, PNA, or combinations of DNA, RNA and PNA, occurs under a wide variety of conditions that vary in temperature, salt concentration, electrostatic strength, buffer composition, and the like. Examples of these conditions and methods for applying them are described in, e.g., Tijssen (1993), supra, and Hames and Higgins, supra. Hybridization generally takes place between about 0° C. and about 70° C., for periods of from about one minute to about one hour, depending on the nature of the sequence to be hybridized and its length. However, it is recognized that hybridizations can occur in seconds or hours, depending on the conditions of the reaction. To illustrate, typical hybridization conditions for a mixture of two 20-mers is to bring the mixture to 68° C., followed by cooling to room temperature (22° C.) for five minutes or at very low temperatures such as 2° C. in 2 microliters. Hybridization between nucleic acids may be facilitated using buffers such as Tris-EDTA (TE), Tris-HCl and HEPES, salt solutions (e.g. NaCl, KCl, $CaCl_2$), or other aqueous solutions, reagents and chemicals. Examples of these reagents include single-stranded binding proteins such as Rec A protein, T4 gene 32 protein, *E. coli* single-stranded binding protein and major or minor nucleic acid groove binding proteins. Other examples of such reagents and chemicals include divalent ions, polyvalent ions and intercalating substances such as ethidium bromide, actinomycin D, psoralen, and angelicin.

IX. Detection and Oligonucleotide Variations

As referred to above, amplified target SARS-CoV nucleic acid in the samples utilized in the methods of the invention is optionally labeled to permit detection of oligonucleotide-target hybridization duplexes. In general, a label can be any moiety that can be attached, e.g., to a primer utilized for amplification and provide a detectable signal (e.g., a quantifiable signal). Labels may be attached to a primer directly or indirectly by a variety of techniques known in the art. Depending on the type of label used, the label can be attached to a terminal (5' or 3' end of the primer) or a non-terminal nucleotide, and can be attached indirectly through linkers or spacer arms of various sizes and compositions. Using commercially available phosphoramidite reagents, one can produce oligomers containing functional groups (e.g., thiols or primary amines) at either the 5' or 3' terminus via an appropriately protected phosphoramidite, and can label such oligonucleotides using protocols described in, for example, *PCR Protocols: A Guide to Methods and Applications* (Innis et al, eds. Academic Press, Inc. (1990)). In one embodiment, the label consists of a biotin molecule covalently bound to the primer at the 5' end. The term "biotinylated primer" refers to a primer with one or more biotin molecules bound either directly to the primer or indirectly through intervening linker molecules.

To further illustrate, detection of oligonucleotide-target hybridization duplexes is optionally by a chemiluminescent assay using a luminol-based reagent as described in, e.g., Whitehead, et al. (1983) *Nature* 30(5):158, which is incorporated by reference, and available commercially. Following hybridization of the oligonucleotide with the labeled target DNA, the biotin molecule attached to the target DNA is conjugated, e.g., to streptavidin-horseradish peroxidase (SA-HRP). Alternatively, the target DNA can be labeled with horseradish peroxidase directly, thereby eliminating the separate conjugation step. In either case, subsequent oxidation of luminol by the horseradish peroxidase enzyme results in the emission of photons, which is then detected, e.g., on standard autoradiography film. The intensity of the signal is a function of DNA quantity. A series of DNA standards containing known amounts of DNA are typically assayed along with one or more unknown samples. The signal intensities of the known DNA standards allow an empirical determination of the functional relationship between signal intensity and DNA quantity, which enables the quantitation of the unknown samples. Many other methods of detection are also optionally utilized to perform the methods of the invention and are referred to in the references cited herein and/or generally known in the art.

Any available method for detecting SARS-CoV amplicons can be used in the present invention. Common approaches include real time amplification detection with molecular beacons or 5'-nuclease probes, detection of intercalating dyes, detection of labels incorporated into the amplification probes or the amplified nucleic acids themselves, e.g., following electrophoretic separation of the amplification products from unincorporated label), hybridization based assays (e.g., array based assays) and/or detection of secondary reagents that bind to the nucleic acids.

To further illustrate, a molecular beacon or a 5'-nuclease probe is optionally designed to include a oligonucleotide of the invention (i.e., is selected from SEQ ID NOS: 1-12 and 15-24) or complements thereto), which molecular beacon or 5'-nuclease probe can be used to detect SARS-CoV amplicons. Molecular beacons or 5'-nuclease probes are described further below. Details on these general approaches are found in the references cited herein, e.g., Sambrook and Ausubel. Additional labeling strategies for labeling nucleic acids and corresponding detection strategies can be found, e.g., in Haugland (2003) *Handbook of Fluorescent Probes and Research Chemicals Ninth Edition* by Molecular Probes, Inc. (Eugene, Oreg.), which is incorporated by reference.

Molecular beacons (MBs) are oligonucleotides designed for real time detection and quantification of target nucleic acids (e.g., target SARS-CoV amplicons). The 5' and 3' termini of MBs collectively comprise a pair of moieties which confers the detectable properties of the MB. One of the termini is attached to a fluorophore and the other is attached to a quencher molecule capable of quenching a fluorescent emission of the fluorophore. For example, one example fluorophore-quencher pair can use a fluorophore such as EDANS or fluorescein, e.g., on the 5'-end and a quencher such as Dabcyl, e.g., on the 3'-end. When the MB is present free in solution, i.e., not hybridized to a second nucleic acid, the stem of the MB is stabilized by complementary base pairing. This self-complementary pairing results in a "hairpin loop" structure for the MB in which the fluorophore and the quenching moieties are proximal to one another. In this confirmation, the fluorescent moiety is quenched by the fluorophore. The loop of the molecular beacon typically comprises an oligonucleotide described herein (i.e., is selected from SEQ ID NOS: 1-12 and 15-24 or complements thereto) and is accordingly complementary to a sequence to be detected in the target SARS-CoV nucleic acid, such that hybridization of the loop to its complementary sequence in the target forces disassociation of the stem, thereby distancing the fluorophore and quencher from each other. This results in unquenching of the fluorophore, causing an increase in fluorescence of the MB.

Details regarding standard methods of making and using MBs are well established in the literature and MBs are available from a number of commercial reagent sources. Further details regarding methods of MB manufacture and use are found, e.g., in Leone et al. (1995) "Molecular beacon probes combined with amplification by NASBA enable homogenous real-time detection of RNA," *Nucleic Acids Res.* 26:2150-2155; Hsuih et al. (1997) "Novel, ligation-dependent PCR assay for detection of hepatitis C in serum" *J. Clin Microbiol* 34:501-507; Kostrikis et al. (1998) "Molecular beacons: spectral genotyping of human alleles" *Science* 279:1228-1229; Sokol et al. (1998) "Real time detection of DNA:RNA hybridization in living cells" *Proc. Natl. Acad. Sci. U.S.A.* 95:11538-11543; Tyagi et al. (1998) "Multicolor molecular beacons for allele discrimination" *Nature Biotechnology* 16:49-53; Fang et al. (1999) "Designing a novel molecular beacon for surface-immobilized DNA hybridization studies" *J. Am. Chem. Soc.* 121:2921-2922; and Marras et al. (1999) "Multiplex detection of single-nucleotide variation using molecular beacons" *Genet. Anal. Biomol. Eng.* 14:151-156, all of which are incorporated by reference. Aspects of MB construction and use are also found in patent literature, such as U.S. Pat. No. 5,925,517 (Jul. 20, 1999) to Tyagi et al. entitled "Detectably labeled dual conformation oligonucleotide probes, assays and kits;" U.S. Pat. No. 6,150,097 to Tyagi et al (Nov. 21, 2000) entitled "Nucleic acid detection probes having non-FRET fluorescence quenching and kits and assays including such probes" and U.S. Pat. No. 6,037,130 to Tyagi et al (Mar. 14, 2000), entitled "Wavelength-shifting probes and primers and their use in assays and kits," all of which are incorporated by reference.

MB components (e.g., oligos, including those labeled with fluorophores or quenchers) can be synthesized using conventional methods. Some of these methods are described further above. For example, oligonucleotides or peptide nucleic acids (PNAs) can be synthesized on commercially available automated oligonucleotide/PNA synthesis machines using standard methods. Labels can be attached to the oligonucleotides or PNAs either during automated synthesis or by post-synthetic reactions which have been described before see, e.g., Tyagi and Kramer (1996), supra. Aspects relating to the synthesis of functionalized oligonucleotides can also be found in Nelson, et al. (1989) "Bifunctional Oligonucleotide Probes Synthesized Using A Novel CPG Support Are Able To Detect Single Base Pair Mutations" *Nucleic Acids Res.* 17:7187-7194, which is incorporated by reference. Labels/quenchers can be introduced to the oligonucleotides or PNAs, e.g., by using a controlled-pore glass column to introduce, e.g., the quencher (e.g., a 4-dimethylaminoazobenzene-4'-sulfonyl moiety (DABSYL). For example, the quencher can be added at the 3' end of oligonucleotides during automated synthesis; a succinimidyl ester of 4-(4'-dimethylaminophenylazo)benzoic acid (DABCYL) can be used when the site of attachment is a primary amino group; and 4-dimethylaminophenylazophenyl-4'-maleimide (DABMI) can be used when the site of attachment is a sulphydryl group. Similarly, fluorescein can be introduced in the oligonucleotides, either using a fluorescein phosphoramadite that replaces a nucleoside with fluorescein, or by using a fluorescein dT phosphoramadite that introduces a fluorescein moiety at a thymidine ring via a linker. To link a fluorescein moiety to a terminal location, iodoacetoamidofluorescein can be coupled to a sulphydryl group. Tetrachlorofluorescein (TET) can be introduced during automated synthesis using a 5'-tetrachloro-fluorescein phosphoramadite. Other reactive fluorophore derivatives and their respective sites of attachment include the succinimidyl ester of 5-carboxyrhodamine-6G (RHD) coupled to an amino group; an iodoacetamide of tetramethylrhodamine coupled to a sulphydryl group; an isothiocyanate of tetramethylrhodamine coupled to an amino group; or a sulfonylchloride of Texas red coupled to a sulphydryl group. During the synthesis of these labeled components, conjugated oligonucleotides or PNAs can be purified, if desired, e.g., by high pressure liquid chromatography or other methods.

A variety of commercial suppliers produce standard and custom molecular beacons, including Cruachem (cruachem.com), Oswel Research Products Ltd. (UK; oswel.com), Research Genetics (a division of Invitrogen, Huntsville Ala. (resgen.com)), the Midland Certified Reagent Company (Midland, Tex. mcrc.com) and Gorilla Genomics, LLC (Alameda, Calif.). A variety of kits, which utilize molecular beacons are also commercially available, such as the Sentinel™ Molecular Beacon Allelic Discrimination Kits from Stratagene (La Jolla, Calif.) and various kits from Eurogentec SA (Belgium, eurogentec.com) and Isogen Bioscience BV (The Netherlands, isogen.com).

In certain embodiments, as also referred to above, a real time PCR assay system that includes one or more 5'-nuclease probes is used for detecting amplified SARS-CoV nucleic acids. These systems operate by using the endogenous nuclease activity of certain polymerases to cleave a quencher or label free from an oligonucleotide of the invention that comprises the quencher and label, resulting in unquenching of the label. The polymerase only cleaves the quencher or label upon initiation of replication, i.e., when the oligonucleotide is bound to the template and the polymerase extends the primer. Thus, an appropriately labeled oligonucleotide and polymerase comprising the appropriate nuclease activity can be used to detect a SARS-CoV nucleic acid of interest. Real time PCR product analysis by, e.g., FRET or the like (and related real time reverse-transcription PCR) provides a well-known technique for real time PCR monitoring that has been used in a variety of contexts, which can be adapted for use with the probes and methods described herein (see, Laurendeau et al. (1999) "TaqMan PCR-based gene dosage assay for predictive testing in individuals from a cancer family with INK4 locus haploinsufficiency" *Clin Chem* 45(7):982-6; Laurendeau et al. (1999) "Quantitation of MYC gene expression in sporadic breast tumors with a real-time reverse transcription-PCR assay" *Clin Chem* 59(12):2759-65; and Kreuzer et al. (1999) "LightCycler technology for the quantitation of bcr/ab1 fusion transcripts" *Cancer Research* 59(13):3171-4, all of which are incorporated by reference). To further illustrate, exemplary 5'-nuclease probes of the invention include (SEQ ID NO: 27)
5'-(6-FAM)-AGCTAACGAGTGTGCGCAAGTATTAAGTGAGATG-(TAMRA)(Phosphate)-3' and (SEQ ID NO: 28)
5'-(6-FAM)-AGAGCCATGCCTAACAT(NFQ)-3'.

X. Systems

The invention also provides a system for detecting SARS-CoV in a sample. The system includes one or more nucleic acid detection reagents as described herein (e.g., probe nucleic acids, sequence specific antibodies, etc.). In certain embodiments, the nucleic acid detection reagents are arrayed on a solid support, whereas in others, they are provided in one or more containers, e.g., for assays performed in solution. The system also includes at least one detector (e.g., a spectrometer, etc.) that detects binding between nucleic acids and/or amplicons thereof from the sample and the nucleic acid detection reagent. Other detectors are described further below. In addition, the system also includes at least one controller operably connected to the detector. The controller includes one or more instructions sets that correlate the binding detected by the detector with a presence of SARS-CoV in the sample.

In some embodiments, at least one container includes the nucleic acid detection reagent. In these embodiments, the system optionally further includes at least one thermal modulator operably connected to the container to modulate temperature in the container, and/or at least one fluid transfer component (e.g., an automated pipettor, etc.) that transfers fluid to and/or from the container, e.g., for performing one or more nucleic acid amplification techniques in the container, etc.

Exemplary commercially available systems that are optionally utilized to detect SARS-CoV nucleic acids using the nucleic acid detection reagents described herein (e.g., oligonucleotides comprising sequences selected from the group consisting of: SEQ ID NOS: 1-12 and 15-24 or complements thereto, sequence specific antibodies, etc.) include, e.g., a LightCycler™ system (e.g., LightCycler™ RNA Master SYBR Green Detection) or a COBAS AMPLICOR® Analyzer, which are available from Roche Diagnostics Corporation (Indianapolis, Ind.), a LUMINEX 100™ system, which is available from the Luminex Corporation (Austin, Tex.), an ABI PRISM® Sequence Detection System, which is available from Applied Biosystems (Foster City, Calif.), and the like.

The invention further provides a computer or computer readable medium that includes a data set that comprises a plurality of character strings that correspond to a plurality of sequences that correspond to one or more of: SEQ ID NOS: 1-12 and 15-24, a substantially identical variant thereof wherein the variant has at least 90% sequence identity to one of SEQ ID NOS: 1-12 and 15-24, and complements of SEQ ID NOS: 1-12 and 15-24 and the variant. Typically, the computer or computer readable medium further includes an automatic synthesizer coupled to an output of the computer or computer readable medium. The automatic synthesizer accepts instructions from the computer or computer readable medium, which instructions direct synthesis of, e.g., one or more probe nucleic acids that correspond to one or more character strings in the data set. Exemplary systems and system components are described further below.

Detectors are structured to detect detectable signals produced, e.g., in or proximal to another component of the system (e.g., in container, on a solid support, etc.). Suitable signal detectors that are optionally utilized, or adapted for use, in these systems detect, e.g., fluorescence, phosphorescence, radioactivity, absorbance, refractive index, luminescence, or the like. Detectors optionally monitor one or a plurality of signals from upstream and/or downstream of the performance of, e.g., a given assay step. For example, the detector optionally monitors a plurality of optical signals, which correspond in position to "real time" results. Example detectors or sensors include photomultiplier tubes, CCD arrays, optical sensors, temperature sensors, pressure sensors, pH sensors, conductivity sensors, scanning detectors, or the like. Each of these as well as other types of sensors is optionally readily incorporated into the systems described herein. Optionally, the systems of the present invention include multiple detectors.

More specific exemplary detectors that are optionally utilized in these systems include, e.g., a resonance light scattering detector, an emission spectroscope, a fluorescence spectroscope, a phosphorescence spectroscope, a luminescence spectroscope, a spectrophotometer, a photometer, and the like. Various synthetic components are also utilized, or adapted for, use in the systems of the invention including, e.g., automated nucleic acid synthesizers, e.g., for synthesizing the oligonucleotides described herein. Detectors and synthetic components that are optionally included in the systems of the invention are described further in, e.g., Skoog et al., *Principles of Instrumental Analysis*, $5^{th}$ Ed., Harcourt Brace College Publishers (1998) and Currell, *Analytical Instrumentation: Performance Characteristics and Quality*, John Wiley & Sons, Inc. (2000), both of which are incorporated by reference.

The systems of the invention also typically include controllers that are operably connected to one or more components (e.g., detectors, synthetic components, thermal modulator, fluid transfer components, etc.) of the system to control operation of the components. More specifically, controllers are generally included either as separate or integral system components that are utilized, e.g., to receive data from detectors, to effect and/or regulate temperature in the containers, to effect and/or regulate fluid flow to or from selected containers, or the like. Controllers and/or other system components is/are optionally coupled to an appropriately programmed processor, computer, digital device, or other information appliance (e.g., including an analog to digital or digital to analog converter as needed), which functions to instruct the operation of these instruments in accordance with preprogrammed or user input instructions, receive data and information from these instruments, and interpret, manipulate and report this information to the user. Suitable controllers are generally known in the art and are available from various commercial sources.

Any controller or computer optionally includes a monitor, which is often a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user. These components are illustrated further below.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation. The computer then receives the data from, e.g., sensors/detectors included within the system, and interprets the data, either provides it in a user understood format, or uses that data to initiate further controller instructions, in accordance with the programming, e.g., such as controlling fluid flow regulators in response to fluid weight data received from weight scales or the like.

The computer can be, e.g., a PC (Intel x86 or Pentium chip-compatible DOS™, OS2™, WINDOWS™, WINDOWS NT™, WINDOWS95™, WINDOWS98™, WINDOWS2000™, WINDOWS XP™, LINUX-based machine, a MACINTOSH™, Power PC, or a UNIX-based (e.g., SUN™ work station) machine) or other common commercially available computer, which is known to one of skill in the art. Standard desktop applications such as word processing software (e.g., Microsoft Word™ or Corel WordPerfect™) and database software (e.g., spreadsheet software such as Microsoft Excel™, Corel Quattro Pro™, or database programs such as Microsoft Access™ or Paradox™) can be adapted to the present invention. Software for performing, e.g., controlling temperature modulators and fluid flow regulators is optionally constructed by one of skill using a standard programming language such as Visual basic, Fortran, Basic, Java, or the like.

Figure 4:
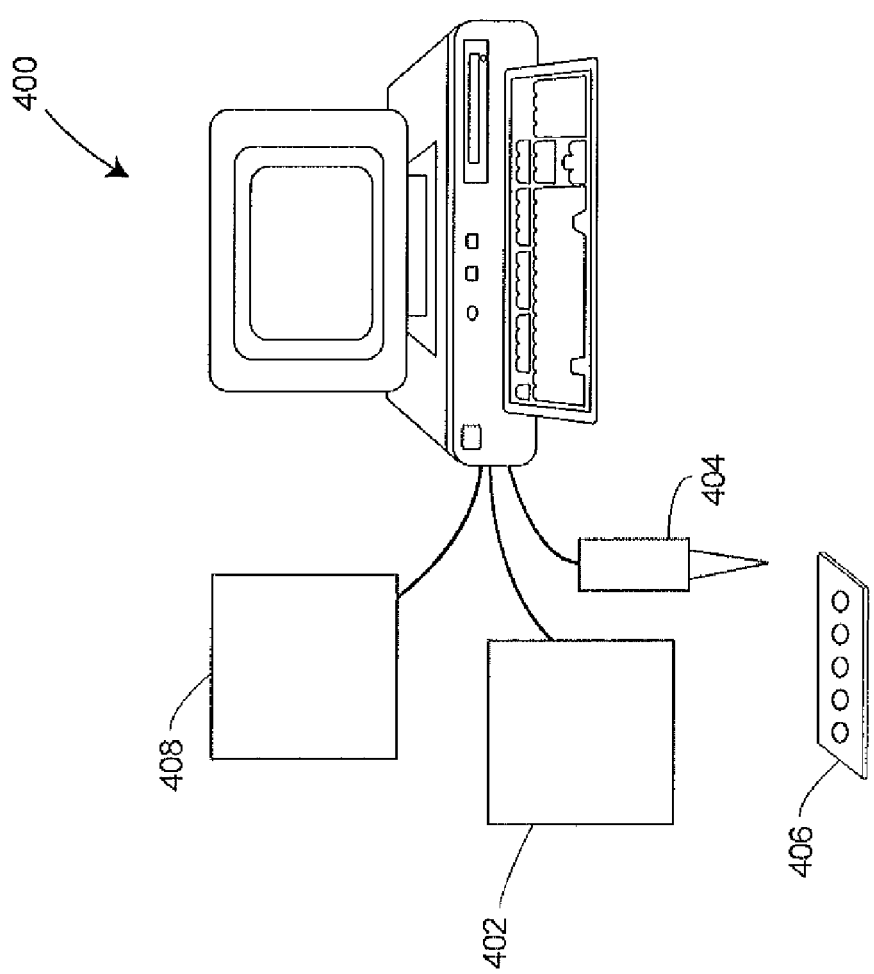
FIG. 4 is a block diagram showing a representative example system for detecting the SARS-CoV in a sample.
Figure 5:
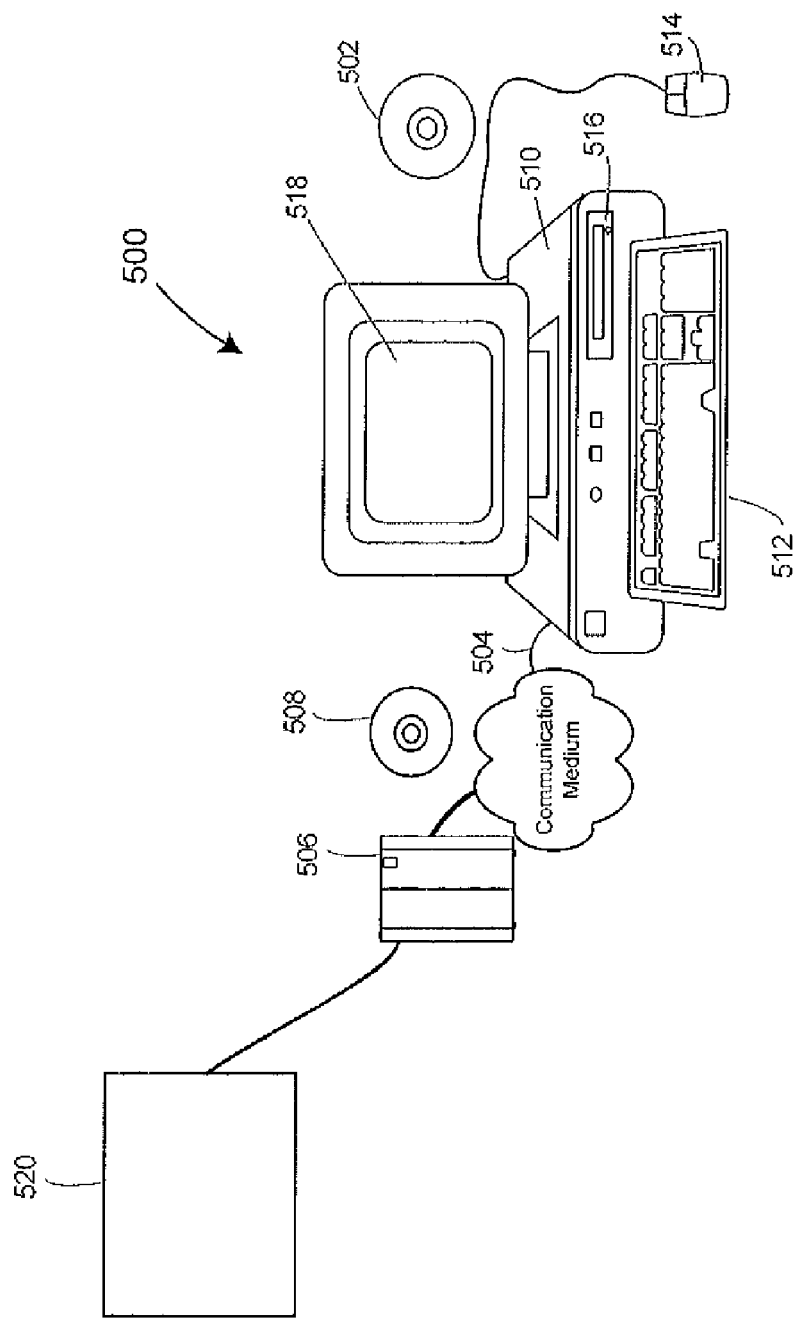
FIG. 5 is a block diagram showing a representative example system including a computer and a computer readable medium in which various aspects of the present invention may be embodied.

FIGS. 4 and 5 are schematics showing representative example systems that include logic devices in which various aspects of the present invention may be embodied. As will be understood by practitioners in the art from the teachings provided herein, the invention is optionally implemented in hardware and/or software. In some embodiments, different aspects of the invention are implemented in either client-side logic or server-side logic. As will be understood in the art, the invention or components thereof may be embodied in a media program component (e.g., a fixed media component) containing logic instructions and/or data that, when loaded into an appropriately configured computing device, cause that device to perform according to. the invention. As will also be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

In particular, FIG. 4 schematically illustrate computer 400 to which detector 402 and fluid transfer component 404 are operably connected. Optionally, detector 402 and/or fluid transfer component 404 is operably connected to computer 400 via a server (not shown in FIG. 4). During operation, fluid transfer component 404 typically transfers fluids, such as sample aliquots comprising labeled SARS-CoV amplicons to nucleic acid detection reagent array 406, e.g., comprising oligonucleotides, sequence specific antibodies, etc., as described herein, arrayed thereon. Thereafter, detector 402 typically detects detectable signals (e.g., fluorescent emissions, etc.) produced by labeled amplicons that hybridize with oligonucleotides attached to nucleic acid detection reagent array 406 after one or more washing steps are performed to wash away non-hybridized nucleic acids from nucleic acid detection reagent array 406 using fluid transfer component 404. As additionally shown, thermal modulator 408 is also operably connected to computer 400. Prior to performing a hybridization assay, target SARS-CoV nucleic acids can be amplified using labeled primer nucleic acids (e.g. primers comprising sequences selected from SEQ ID NOS: 1-12 and 15-24 or complements thereof). The amplicons of these amplification reactions are then typically transferred to nucleic acid detection reagent array 406 using fluid transfer component 404, as described above, to perform the binding assay. In some embodiments, binding assays are performed concurrently with SARS-CoV nucleic acid amplification in thermal modulator 408 using, e.g., molecular beacons, 5'-nuclease probes, or the like that comprise sequences selected from the group consisting of: SEQ ID NOS: 1-12 and 15-24, a substantially identical variant thereof wherein the variant has at least 90% sequence identity to one of SEQ ID NOS: 1-12 and 15-24, and complements of SEQ ID NOS: 1-12 and 15-24 and the variant. In these embodiments, detector 402 detects detectable signals produced as the amplification reactions are performed using thermal modulator 408.

FIG. 5 schematically shows information appliance or digital device 500 that may be understood as a logical apparatus that can read instructions from media 502 and/or network port 504, which can optionally be connected to server 506 having fixed media 508. Digital device 500 can thereafter use those instructions to direct server or client logic, as understood in the art, to embody aspects of the invention. One type of logical apparatus that may embody the invention is a computer system as illustrated in 500, containing CPU 510, optional input devices 512 and 514, disk drives 516 and optional monitor 518. Fixed media 502, or fixed media 508 over port 504, may be used to program such a system and may represent a disk-type optical or magnetic media, magnetic tape, solid state dynamic or static memory, or the like. In specific embodiments, the invention may be embodied in whole or in part as software recorded on this fixed media. Communication port 504 may also be used to initially receive instructions that are used to program such a system and may represent any type of communication connection. Optionally, the invention is embodied in whole or in part within the circuitry of an application specific integrated circuit (ACIS) or a programmable logic device (PLD). In such a case, the invention may be embodied in a computer understandable descriptor language, which may be used to create an ASIC, or PLD.

FIG. 5 also includes automatic synthesizer 350, which is operably connected to digital device 500 via server 506. Optionally, automatic synthesizer 520 As directly connected to digital device 506. Optionally, operation, automatic synthesizer 520 typically receives instructions to synthesize one or more primers or probes that comprise a sequence selected from the group consisting of: SEQ ID NOS: 1-12 and 15-24, a substantially identical variant thereof wherein the variant has at least 90% sequence identity to one of SEQ ID NOS: 1-12 and 15-24, and complements of SEQ ID NOS: 1-12 and 15-24 and the variant, which are included in a data set comprised by, e.g., digital device 500 and/or a computer readable medium, such as fixed media 502 and/or 508.

XI. Kits

The nucleic acid detection reagents (e.g., primer nucleic acids, probe nucleic acids, etc.) employed in the methods of the present invention are optionally packaged into kits. As described herein, the nucleic acid detection reagents of the invention detectably bind to target SARS-CoV nucleic acids. In addition, the kits may also include suitably packaged reagents and materials needed for nucleic acid immobilization, hybridization, and/or detection, such solid supports, buffers, enzymes, and nucleic acid standards, as well as instructions for conducting the assay. Optionally, the nucleic acid detection reagents (e.g., oligonucleotides, sequence specific antibodies, etc.) of the invention are provided already attached or otherwise immobilized on solid supports. As another option, nucleic acid detection reagents are provided free in solution in containers, e.g., for performing the detection methods of the invention in the solution phase. In some of these embodiments, nucleic acid detection reagents of the kits comprise labels and/or quencher moieties, such as when molecular beacons, 5'-nuclease probes, or the like comprise sequences selected from the group consisting of: SEQ ID NOS: 1-12 and 15-24, a substantially identical variant thereof wherein the variant has at least 90% sequence identity to one of SEQ ID NOS: 1-12 and 15-24, and complements of SEQ ID NOS: 1-12 and 15-24 and the variant. In certain embodiments, kits further include labeled primers for amplifying target SARS-CoV sequences in a sample.

The kit also includes one or more of: a set of instructions for contacting the nucleic acid detection reagents with nucleic acids from a sample or amplicons thereof and detecting binding between the nucleic acid detection reagents and SARS-CoV nucleic acids, or at least one container for packaging the nucleic acid detection reagents and the set of instructions. Exemplary solid supports include in the kits of the invention are optionally selected from, e.g., a plate, a microwell plate, a bead, a microbead, a tube (e.g., a microtube, etc.), a fiber, a whisker, a comb, a hybridization chip, a membrane, a single crystal, a ceramic layer, a self-assembling monolayer, or the like.

In some embodiments, the kit further includes at least one primer nucleic acid that is at least partially complementary to at least one segment of a SARS-CoV nucleic acid, e.g., for amplifying a segment of the SARS-CoV nucleic acid. In these embodiments, the kit typically further includes a set of instructions for amplifying one or more subsequences of that nucleic acid with the primer nucleic acids, at least one nucleotide incorporating biocatalyst (e.g., a polymerase), and one or more deoxyribonucleotides. In certain embodiments, the primer nucleic acids comprise at least one label (e.g., a fluorescent dye, a radioisotope, etc.). Suitable labels are described further herein. For example, the primer nucleic acid is optionally conjugated with biotin or a biotin derivative. In these embodiments, the kit typically further includes an enzyme conjugated with avidin or an avidin derivative, or streptavidin or a streptavidin derivative, e.g., for effecting the detection of binding between the nucleic acid detection reagents of the invention and target nucleic acids. In these embodiments, the kit generally further includes at least one nucleotide incorporating biocatalyst (e.g., a polymerase, a ligase, or the like). In these embodiments, the kit typically also further comprising one or more nucleotides, e.g., for use in amplifying the target nucleic acids. Optionally, at least one of the nucleotides comprises a label. In some of these embodiments, the kits further include at least one pyrophosphatase (e.g., a thermostable pyrophosphatase), e.g., for use in minimizing pyrophosphorolysis, uracil N-glycosylase (UNG) (e.g., a thermostable UNG), e.g., for use in applications where protection against carry-over contamination is desirable.

XII. EXAMPLES

It is understood that the examples and embodiments described herein are for illustrative purposes only and are not intended to limit the scope of the claimed invention. It is also understood that various modifications or changes in light the examples and embodiments described herein will be suggested to persons skilled in the art and are to be included within the spirit and purview of this application and scope of the appended claims.

Example 1

Nested PCR Detection of SARS Coronavirus

The SARS Coronavirus Detection RT-PCT Diagnostic is specifically designed for detecting patients suspected of having SARS. Reagents are used for end-point PCR and the products analyzed by agarose gel electrophoresis. Reagents are designed to allow flexibility in the choice of reverse transcriptase and Taq polymerases.

Reagents provided (10 items):

1. Positive control (2.5 kb DNA fragment comprising the primer sequences) Neat
2. Positive control 1/10 dilution
3. Positive control 1/100 dilution
4. Negative control A (water or buffer solution alone)
5. Negative control B (cloning vector of the positive control fragment)
6. GISSARSOUT_F (10 μM) (SEQ ID NO: 11)
7. GISSARSOUT_R (10 μM )* (SEQ ID NO: 12 or 20)
8. GISSARSIN_F (10 μM) (SEQ ID NO: 13 (=SAR1S; see, Drosten et al. (2003) "Identification of a novel coronavirus in patients with severe acute respiratory syndrome," *N. Engl. J. Med.* 348:1967-1976), SEQ ID NO: 15 or 18)
9. GISSARSIN_R (10 μM) (SEQ ID NO: 14 (=SAR1As, see, Drosten et al. (2003), supra), SEQ ID NO: 16 or 19)
10. Sterile water for PCR

*GISSARSOUT_R is used both as the 3'-primer for first-strand cDNA synthesis and the first round PCR.

Reagents required but not provided:

| | |
|---|---|
| 1. RNA extraction | |
| Recommended suppliers: | Rneasy ® kit (Qiagen)<br>or<br>TRIZOL ® (Invitrogen) |
| 2. First-strand cDNA synthesis | |
| Recommended suppliers: | Expand reverse transcriptase (Roche) or Superscript II reverse transcriptase (Invitrogen) |
| 3. dNTPs Mix | |
| Recommended suppliers: | dNTPs Mix (New England Biolabs)<br>or<br>dNTPs Mix (Invitrogen) |
| 4. Taq Polymerase | |
| Recommended suppliers: | Platinum Taq Polymerase<br>or<br>High Fidelity PCR system (Roche) |

Protocol:

Samples from patients suspected of having SARS infections, such as blood and tissue need to be handled according to WHO (on the world wide web at who.int/en/as of Apr. 20, 2004) or CDC (on the world wide web at cdc.gov/ as of Apr. 20, 2004) recommendations.

1. RNA is extracted by manufacturers' instructions (TRIZOL® or Qiagen kits).
2. First-stand cDNA synthesis is performed on extracted RNA using GISSARSOUT_R (2 μl) in a 20 μl reaction volume.
3. First round PCR: The cDNA product (2.5 μl) is used as template using GISSARSOUT_F (1.25 μl) and GISSARSOUT_R (1.25 μl) in a 25 μl reaction volume. A 440 bp fragment can be detected at this step if the viral titre of the sample is very high. Note: The control templates (1 μl) can be run along side with every PCR reaction.

PCR conditions:

| | |
|---|---|
| 94° C. for 2 min | 35 × cycles |
| 94° C. for 10 sec | |
| 50° C. for 30 sec | |

-continued

72° C. for 1 min
72° C. for 7 min

Figure 6:
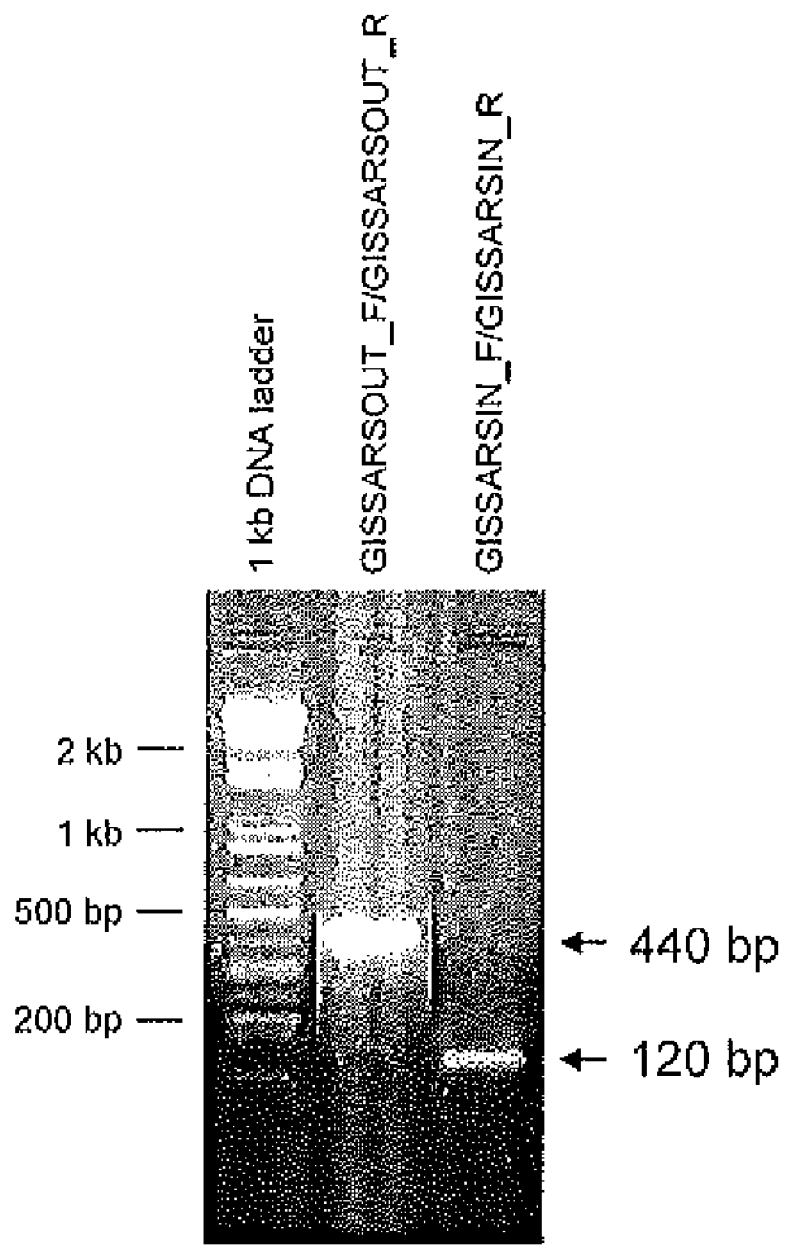
FIG. 6 is a photograph of an agarose gel that shows the results of a nested polymerase chain reaction in a positive clinical sample according to the procedure of Example 2 using primers of SEQ ID NO: 11 and SEQ ID NO: 12 as reagents 6 and 7 and using primers of SEQ ID NO: 13 and SEQ ID NO: 14 as reagents 8 and 9, respectively.

4. Second round PCR: Products from the first round PCR (2.5 µl) is used as template for the second PCR using GISSARSIN_F (1.25 µl) and GISSARSIN_R (1.25 µl) in a 25 µl reaction volume with the same PCR conditions as the first round PCR. Note: The control templates (1 µl) can be run along side with every PCR reaction.
5. Products are analyzed on a 1.2-1.5% agarose gel. A 120 bp fragment can be detected for positive SARS confirmation. See FIG. 6.

Example 2

Detection of SARS Coronavirus by Real Time PCR

SARS-CoV can be detected in a clinical sample using real time PCR rather than the standard RT-PCR method described in Example 1.

The following are mixed in a 20 µL reaction:
10 µL 2× Universal PCR Mix (Applied Biosystems)
1.8 µL 10 µM Primer 1 (e.g. SEQ ID NO: 11)
1.8 µL 10 µM Primer 2 (e.g. SEQ ID NO: 20)
0.5 µL 10 µM 5'-nuclease probe (e.g. SEQ ID NO: 21)
4.9 µL Water
1.0 µL template Final concentrations of PCR primers are 900 nM; final concentration of 5'-nuclease probe is 250 nM.

Reactions are preferably run in duplicate.

PCR cycling is 95° C. for 10 minutes, followed by 40 cycles of denaturation at 95° C., 15 seconds and annealing and extension at 60° C., 1 minute.

Fluorescence is monitored as described by the system manufacturer during annealing and extension cycles.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of detecting a severe acute respiratory syndrome coronavirus in a sample, the method comprising:

(a) contacting nucleic acids from the sample in at least one nucleic acid amplification reaction with at least one primer nucleic acid selected from the group consisting of: SEQ ID NOS: 11 and 22 and full complements thereof, further comprising at least one additional primer nucleic acid selected from the group consisting of: SEQ ID NOS: 12 and 20 and full complements thereof; and, (b) detecting the nucleic acids and/or one or more amplicons thereof from the nucleic acid amplification reaction during or after (a), thereby detecting the severe acute respiratory syndrome coronavirus in the sample.

2. The method of claim 1, wherein at least one of the primer nucleic acids comprises a modified primer nucleic acid.

3. The method of claim 1, wherein at least one of the amplicons is about 440 nucleotides in length.

4. The method of claim 1, wherein the nucleic acid amplification reaction comprises a nested polymerase chain reaction.

5. The method of claim 1, wherein at least one of the primer nucleic acids comprises at least one label.

6. The method of claim 5, wherein (b) comprises detecting a detectable signal produced by the label, or amplifying a detectable signal produced by the label to produce an amplified signal and detecting the amplified signal.

7. The method of claim 1, wherein (b) comprises monitoring binding between the amplicons and at least one oligonucleotide selected from the group consisting of: SEQ ID NO: 27 and SEQ ID NO: 28, a substantially identical variant thereof wherein the variant has at least 90% sequence identity to one of SEQ ID NO: 27 and SEQ ID NO: 28 and full complements of SEQ ID NO: 27 and SEQ ID NO: 28 and the variant.

8. The method of claim 7, wherein the oligonucleotide comprises at least one label and/or at least one quencher moiety.

9. A method of determining a presence of a severe acute respiratory syndrome coronavirus in a sample, the method comprising:
   (a) contacting nucleic acids and/or amplicons thereof from the sample with one or more oligonucleotides selected from the group consisting of: SEQ ID NOS: 11 and 22 and full complements thereof, and a substantially identical variant thereof wherein the variant has at least 90% sequence identity to one of SEQ ID NOS: 11 and 22 and full complements thereof,
   further comprising one or more oligonucleotides selected from the group consisting of: SEQ ID NOS: 12 and 20 and full complements thereof, and a substantially identical variant thereof wherein the variant has at least 90% sequence identity to one of SEQ ID NOS: 12 and 20 and full complements thereof,
   further comprising at least one oh oligonucleotide selected from the group consisting of: SEQ ID NO: 27 and SEQ ID NO: 28, a substantially identical variant thereof wherein the variant has at least 90% sequence identity to one of SEQ ID NO: 27 and SEQ ID NO: 28, and full complements of SEQ ID NO: 27 and SEQ ID NO: 28 and the variant, and
   (b) monitoring binding between the nucleic acids and/or amplicons thereof, and the oligonucleotides, wherein detectable binding between the nucleic acids and/or amplicons thereof, and the oligonucleotides, determines the presence of the severe acute respiratory syndrome coronavirus in the sample.

10. The method of claim 9, wherein (a) comprises contacting the nucleic acids and/or amplicons thereof with the oligonucleotides in solution at a temperature of at least 42° C. for at least 15 minutes, wherein a total weight of the solution comprises about 50% formalin and comprises heparin at a concentration of about 1 mg/ml.

11. The method of claim 9, comprising repeating (a) and (b) at least once using at least one additional sample and comparing the binding between the nucleic acids and/or amplicons thereof, and the oligonucleotides, of (b) with at least one repeated (b).

12. The method of claim 9, wherein at least one segment of the nucleic acids is amplified prior to or during (a) using at least one nucleic acid amplification technique to produce the amplicons and (b) comprises monitoring the binding between the nucleic acids and/or amplicons thereof, and the oligonucleotides, during or after amplification.

13. A composition comprising a sample derived from a subject and at least one oligonucleotide selected from the group consisting of: SEQ ID NOS: 11 and 22, a substantially identical variant thereof wherein the variant has at least 90% sequence identity to one of SEQ ID NOS: 11 and 22, and full complements of SEQ ID NOS: 11 and 22 and the variant,
   further comprising at least one oligonucleotide selected from the group consisting of: SEQ ID NOS: 12 and 20, a substantially identical variant thereof wherein the variant has at least 90% sequence identity to one of SEQ ID NOS: 12 and 20, and full complements of SEQ ID NOS: 12 and 20 and the variant.

14. A kit, comprising:
   (a) at least one oligonucleotide selected from the group consisting of: SEQ ID NOS: 11 and 22, a substantially identical variant thereof wherein the variant has at least 90% sequence identity to one of SEQ ID NOS: 11 and 22, and full complements of SEQ ID NO: 11 and the variant,
   further comprising at least one oligonucleotide selected from the group consisting of: SEQ ID NOS: 12 and 20, a substantially identical variant thereof wherein the variant has at least 90% sequence identity to one of SEQ ID NOS: 12 and 20, and full complements of SEQ ID NOS: 12 and 20 and the variant; and one or more of:
   (b) instructions for determining a presence of a severe acute respiratory syndrome coronavirus in a sample by monitoring binding between nucleic acids and/or amplicons thereof from the sample and the oligonucleotide, wherein the presence of the severe acute respiratory syndrome coronavirus in the sample is unknown or unsubstantiated; or,
   (c) at least one container for packaging at least the oligonucleotide.

15. The kit of claim 14, further comprising at least one enzyme.

16. A system for detecting a severe acute respiratory syndrome coronavirus in a sample, comprising:
   (a) at least one oligonucleotide selected from the group consisting of: SEQ ID NOS: 11 and 22, substantially identical variant thereof wherein the variant has at least 90% sequence identity to one of SEQ ID NOS: 11 and 22, and full complements of SEQ ID NOS: 11 and 22 and the variant,
   further comprising at least one oligonucleotide selected from the group consisting of: SEQ ID NOS: 12 and 20, a substantially identical variant thereof wherein the variant has at least 90% sequence identity to one of SEQ ID NOS: 12 and 20, and full complements of SEQ ID NOS: 12 and 20 and the variant;
   (b) at least one detector that detects binding between nucleic acids and/or amplicons thereof from the sample and the oligonucleotide; and,
   (c) at least one controller operably connected to the detector, which controller comprises one or more instructions sets that correlate the binding detected by the detector with a presence of the severe acute respiratory syndrome coronavirus in the sample.

* * * * *